United States Patent
Orr et al.

(10) Patent No.: US 11,904,113 B2
(45) Date of Patent: *Feb. 20, 2024

(54) URETERAL AND BLADDER CATHETERS AND METHODS OF INDUCING NEGATIVE PRESSURE TO INCREASE RENAL PERFUSION

(71) Applicant: Roivios Limited, Nassau (BS)

(72) Inventors: David E. Orr, Piedmont, SC (US);
Jacob L. Upperco, Atlanta, GA (US);
John R. Erbey, II, Milton, GA (US)

(73) Assignee: Roivios Limited, Nassau (BS)

( * ) Notice: Subject to any disclaimer, the term of this patent is extended or adjusted under 35 U.S.C. 154(b) by 259 days.

This patent is subject to a terminal disclaimer.

(21) Appl. No.: 17/077,793

(22) Filed: Oct. 22, 2020

(65) Prior Publication Data
US 2021/0077785 A1   Mar. 18, 2021

Related U.S. Application Data

(63) Continuation of application No. 15/687,083, filed on Aug. 25, 2017, now Pat. No. 10,926,062, which is a
(Continued)

(51) Int. Cl.
*A61M 25/04*    (2006.01)
*A61M 25/01*    (2006.01)
(Continued)

(52) U.S. Cl.
CPC .............. *A61M 25/04* (2013.01); *A61M 1/73* (2021.05); *A61M 1/74* (2021.05); *A61M 1/743* (2021.05);
(Continued)

(58) Field of Classification Search
CPC .............. A61M 27/008; A61M 25/007; A61M 25/0017; A61M 2210/1082;
(Continued)

(56) References Cited

U.S. PATENT DOCUMENTS

| 1,870,942 A | 8/1932 | Beatty |
| 2,285,980 A | 6/1942 | Jeckel |

(Continued)

FOREIGN PATENT DOCUMENTS

| AU | 2013332448 A1 | 4/2015 |
| CA | 1243581 A | 10/1988 |

(Continued)

OTHER PUBLICATIONS

Bart et al.; "Ultrafiltration in Decompensated Heart Failure with Cardiorenal Syndrome"; N Engl J Med; 2012; p. 2296-2304; vol. 367.

(Continued)

*Primary Examiner* — Adam Marcetich
(74) *Attorney, Agent, or Firm* — THE WEBB LAW FIRM

(57) ABSTRACT

A ureteral catheter is provided, including a drainage lumen including a proximal portion and a distal portion configured to be positioned in a patient's kidney, renal pelvis, and/or in the ureter adjacent to the renal pelvis, the distal portion including a retention portion for maintaining positioning of the distal portion of the drainage lumen, the retention portion including at least two openings on a sidewall of the retention portion for permitting fluid flow into the drainage lumen wherein a total area of a proximal most opening of the at least two openings is less than a total area of more distal opening(s) nearer to the distal end of the drainage lumen, and wherein when negative pressure is applied through the ureteral catheter, fluid is drawn into the ureteral catheter through the at least two openings.

38 Claims, 44 Drawing Sheets

Related U.S. Application Data continuation-in-part of application No. 15/411,884, filed on Jan. 20, 2017, now Pat. No. 10,512,713, which is a continuation-in-part of application No. 15/214,955, filed on Jul. 20, 2016, now Pat. No. 10,307,564.

(60) Provisional application No. 62/300,025, filed on Feb. 25, 2016, provisional application No. 62/278,721, filed on Jan. 14, 2016, provisional application No. 62/260,966, filed on Nov. 30, 2015, provisional application No. 62/194,585, filed on Jul. 20, 2015.

(51) Int. Cl.
  *A61M 25/00* (2006.01)
  *A61M 25/10* (2013.01)
  *A61M 1/00* (2006.01)
  *A61M 39/12* (2006.01)
  *A61M 25/02* (2006.01)

(52) U.S. Cl.
  CPC ............... *A61M 1/75* (2021.05); *A61M 1/80* (2021.05); *A61M 1/84* (2021.05); *A61M 25/007* (2013.01); *A61M 25/0017* (2013.01); *A61M 25/0023* (2013.01); *A61M 25/0026* (2013.01); *A61M 25/0041* (2013.01); *A61M 25/0108* (2013.01); *A61M 25/1025* (2013.01); *A61M 25/10* (2013.01); *A61M 39/12* (2013.01); *A61M 2025/0213* (2013.01); *A61M 2202/0496* (2013.01); *A61M 2205/3303* (2013.01); *A61M 2205/3317* (2013.01); *A61M 2205/3334* (2013.01); *A61M 2205/3368* (2013.01); *A61M 2205/52* (2013.01); *A61M 2205/583* (2013.01); *A61M 2210/1082* (2013.01); *A61M 2210/1085* (2013.01); *A61M 2210/1089* (2013.01); *A61M 2230/00* (2013.01); *A61M 2230/207* (2013.01); *A61M 2230/50* (2013.01); *A61M 2230/65* (2013.01)

(58) Field of Classification Search
  CPC .. A61M 2210/1085; A61M 2210/1078; A61M 25/003; A61M 27/002; A61M 2202/0496; A61M 2210/1089; A61F 2/04; A61F 2002/048; A61F 2/042; A61F 2002/047
  See application file for complete search history.

(56) References Cited

U.S. PATENT DOCUMENTS

| | | |
|---|---|---|
| 2,649,092 A | 8/1953 | Wallace |
| 3,108,595 A | 10/1963 | Overment |
| 3,397,699 A | 8/1968 | Kohl |
| 3,561,431 A | 2/1971 | Karl |
| 3,707,967 A | 1/1973 | Kitrilakis |
| 3,875,941 A | 4/1975 | Adair |
| 3,938,529 A | 2/1976 | Gibbons |
| 3,938,530 A | 2/1976 | Santomieri |
| 3,943,929 A | 3/1976 | Patel |
| 4,265,243 A | 5/1981 | Taylor |
| 4,306,557 A | 12/1981 | North |
| 4,324,663 A | 4/1982 | Hirel et al. |
| 4,349,029 A | 9/1982 | Mott |
| 4,425,124 A | 1/1984 | Womack |
| 4,437,856 A | 3/1984 | Valli |
| 4,531,933 A | 7/1985 | Norton et al. |
| 4,568,338 A | 2/1986 | Todd |
| 4,571,241 A | 2/1986 | Christopher |
| 4,575,371 A | 3/1986 | Nordqvist et al. |
| 4,629,015 A | 12/1986 | Fried et al. |
| 4,681,564 A | 7/1987 | Landreneau |
| 4,710,169 A | 12/1987 | Christopher |
| 4,738,667 A | 4/1988 | Galloway |
| 4,813,935 A | 3/1989 | Haber et al. |
| 4,834,724 A | 5/1989 | Geiss et al. |
| 4,932,938 A | 6/1990 | Goldberg et al. |
| 4,935,004 A | 6/1990 | Cruz |
| 4,945,895 A | 8/1990 | Takai et al. |
| 4,950,228 A | 8/1990 | Knapp, Jr. et al. |
| 4,957,479 A | 9/1990 | Roemer |
| 5,009,639 A | 4/1991 | Keymling |
| 5,011,488 A | 4/1991 | Ginsburg |
| 5,041,093 A | 8/1991 | Chu |
| 5,044,902 A | 9/1991 | Malbec |
| 5,059,169 A | 10/1991 | Zilber |
| 5,078,684 A | 1/1992 | Yasuda |
| 5,098,440 A | 3/1992 | Hillstead |
| 5,116,309 A | 5/1992 | Coll |
| 5,141,502 A | 8/1992 | Macaluso, Jr. |
| 5,193,533 A | 3/1993 | Body et al. |
| 5,256,146 A | 10/1993 | Ensminger et al. |
| 5,370,690 A | 12/1994 | Barrett |
| 5,401,257 A | 3/1995 | Chevalier, Jr. et al. |
| 5,451,215 A | 9/1995 | Wolter |
| 5,451,218 A | 9/1995 | Moore |
| 5,505,717 A | 4/1996 | Moore |
| 5,514,112 A | 5/1996 | Chu et al. |
| 5,523,092 A | 6/1996 | Hanson et al. |
| 5,536,274 A | 7/1996 | Neuss |
| 5,540,701 A | 7/1996 | Sharkey et al. |
| 5,554,144 A | 9/1996 | Wallace et al. |
| 5,562,622 A | 10/1996 | Tihon |
| 5,599,291 A | 2/1997 | Balbierz et al. |
| 5,647,843 A | 7/1997 | Mesrobian et al. |
| 5,662,713 A | 9/1997 | Andersen et al. |
| 5,709,874 A | 1/1998 | Hanson et al. |
| 5,727,555 A | 3/1998 | Chait |
| 5,762,599 A | 6/1998 | Sohn |
| 5,769,821 A | 6/1998 | Abrahamson et al. |
| 5,785,641 A | 7/1998 | Davis |
| 5,795,319 A | 8/1998 | Ali |
| 5,865,764 A | 2/1999 | Moorhead |
| 5,873,865 A | 2/1999 | Horzewski et al. |
| 5,895,398 A | 4/1999 | Wensel et al. |
| 5,902,336 A | 5/1999 | Mishkin |
| 5,915,386 A | 6/1999 | Lloyd et al. |
| 5,957,867 A | 9/1999 | Lloyd et al. |
| 5,972,019 A | 10/1999 | Engelson et al. |
| 5,989,207 A | 11/1999 | Hughes |
| 6,066,113 A | 5/2000 | Overtoom |
| 6,090,069 A | 7/2000 | Walker |
| 6,111,520 A | 8/2000 | Allen et al. |
| 6,200,485 B1 | 3/2001 | Kitaevich et al. |
| 6,214,037 B1 | 4/2001 | Mitchell et al. |
| 6,283,940 B1 | 9/2001 | Mulholland |
| 6,332,892 B1 | 12/2001 | Desmond, III et al. |
| 6,364,868 B1 | 4/2002 | Ikeguchi |
| 6,402,736 B1 | 6/2002 | Brown et al. |
| 6,442,415 B1 | 8/2002 | Bis et al. |
| 6,461,346 B1 | 10/2002 | Buelna |
| 6,478,778 B1 | 11/2002 | Jacobsen et al. |
| 6,482,222 B1 | 11/2002 | Bruckheimer et al. |
| 6,500,158 B1 | 12/2002 | Ikeguchi |
| 6,558,350 B1 | 5/2003 | Hart et al. |
| 6,569,150 B2 | 5/2003 | Teague et al. |
| 6,620,202 B2 | 9/2003 | Bottcher et al. |
| 6,648,863 B2 | 11/2003 | Reever |
| 6,676,623 B2 | 1/2004 | Whitmore, III |
| 6,685,744 B2 | 2/2004 | Gellman et al. |
| 6,702,834 B1 | 3/2004 | Boylan et al. |
| 6,764,519 B2 | 7/2004 | Whitmore, III |
| 6,780,322 B1 | 8/2004 | Bissler et al. |
| 6,837,868 B1 | 1/2005 | Fajnsztajn |
| 7,025,753 B2 | 4/2006 | Reever |
| 7,037,345 B2 | 5/2006 | Bottcher et al. |
| 7,044,981 B2 | 5/2006 | Liu et al. |
| 7,316,663 B2 | 1/2008 | Whitmore, III |
| 7,329,226 B1 | 2/2008 | Ni et al. |
| 7,396,366 B2 | 7/2008 | Ward |
| 7,507,218 B2 | 3/2009 | Aliski et al. |
| 7,550,978 B2 | 6/2009 | Joy et al. |

(56) References Cited

U.S. PATENT DOCUMENTS

| | | |
|---|---|---|
| 7,603,170 B2 | 10/2009 | Hatlestad et al. |
| 7,682,401 B2 | 3/2010 | Deal |
| 7,722,677 B2 | 5/2010 | Ward |
| 7,727,222 B2 | 6/2010 | Da Silva et al. |
| 7,736,354 B2 | 6/2010 | Gelfand et al. |
| 7,758,562 B2 | 7/2010 | Gelfand et al. |
| 7,758,563 B2 | 7/2010 | Gelfand et al. |
| 7,766,961 B2 | 8/2010 | Patel et al. |
| 7,837,667 B2 | 11/2010 | Gelfand et al. |
| 7,850,704 B2 | 12/2010 | Burnett et al. |
| 7,857,803 B1 | 12/2010 | Salinas et al. |
| 7,879,020 B1 | 2/2011 | Salinas et al. |
| 7,938,817 B2 | 5/2011 | Gelfand et al. |
| 7,972,292 B2 | 7/2011 | Behl et al. |
| 8,007,460 B2 | 8/2011 | Gelfand et al. |
| 8,021,307 B2 | 9/2011 | White et al. |
| 8,075,513 B2 | 12/2011 | Rudko et al. |
| 8,088,170 B2 | 1/2012 | Whitmore, III |
| 8,105,317 B2 | 1/2012 | Reever et al. |
| 8,157,785 B2 | 4/2012 | Salinas et al. |
| 8,177,741 B2 | 5/2012 | Hammack et al. |
| 8,252,065 B2 | 8/2012 | Ward |
| 8,328,877 B2 | 12/2012 | Gellman |
| 8,444,623 B2 | 5/2013 | Gelfand et al. |
| 8,486,010 B2 | 7/2013 | Nomura |
| 8,512,795 B2 | 8/2013 | Dias et al. |
| 8,568,387 B2 | 10/2013 | Paz |
| 8,585,675 B2 | 11/2013 | Salinas et al. |
| 8,597,260 B2 | 12/2013 | Tucker |
| 8,597,273 B2 | 12/2013 | Salinas et al. |
| 8,747,388 B2 | 6/2014 | Pandey et al. |
| 8,795,305 B2 | 8/2014 | Martin et al. |
| 8,827,924 B2 | 9/2014 | Paz et al. |
| 8,852,289 B2 | 10/2014 | Whitmore, III |
| 8,865,063 B2 | 10/2014 | Burnett |
| 8,932,320 B1 | 1/2015 | Janardhan et al. |
| 9,014,815 B2 | 4/2015 | Yang et al. |
| 9,060,888 B2 | 6/2015 | Gellman |
| 9,308,348 B2 | 4/2016 | Mulvihill et al. |
| 9,339,636 B1 | 5/2016 | Khan et al. |
| 9,682,220 B2 | 6/2017 | Schertiger et al. |
| 9,744,331 B2 | 8/2017 | Erbey, II et al. |
| 9,750,634 B2 | 9/2017 | Bar-Am |
| 9,788,928 B2 | 10/2017 | Forsell |
| 9,849,224 B2 | 12/2017 | Angwin et al. |
| 9,980,663 B2 | 5/2018 | Wabel et al. |
| 10,182,747 B2 | 1/2019 | Charlez et al. |
| 10,226,606 B2 | 3/2019 | Wan et al. |
| 10,307,566 B2 | 6/2019 | Bishawi |
| 10,449,329 B2 | 10/2019 | Foley et al. |
| 11,040,180 B2 | 6/2021 | Erbey, II et al. |
| 2001/0053936 A1 | 12/2001 | Whitmore, III |
| 2001/0056273 A1 | 12/2001 | Ewers |
| 2002/0052576 A1 | 5/2002 | Massengale |
| 2002/0062148 A1 | 5/2002 | Hart |
| 2002/0068093 A1 | 6/2002 | Trogolo et al. |
| 2002/0082547 A1 | 6/2002 | Deniega et al. |
| 2002/0085951 A1 | 7/2002 | Gelfand et al. |
| 2002/0143292 A1 | 10/2002 | Flinchbaugh |
| 2002/0143389 A1 | 10/2002 | St. Pierre |
| 2002/0177902 A1 | 11/2002 | Rioux et al. |
| 2002/0183852 A1 | 12/2002 | McWeeney |
| 2002/0183853 A1 | 12/2002 | Mitchell et al. |
| 2002/0188246 A1 | 12/2002 | Hayner et al. |
| 2002/0193667 A1 | 12/2002 | McNair |
| 2003/0009132 A1 | 1/2003 | Schwartz et al. |
| 2003/0018291 A1 | 1/2003 | Hill et al. |
| 2003/0060806 A1 | 3/2003 | Ikeguchi |
| 2003/0069534 A1 | 4/2003 | Work et al. |
| 2003/0074082 A1 | 4/2003 | Bottcher et al. |
| 2003/0109930 A1 | 6/2003 | Bluni et al. |
| 2003/0120261 A1 | 6/2003 | Gellman |
| 2003/0135147 A1 | 7/2003 | Rosenberg et al. |
| 2003/0135195 A1 | 7/2003 | Jimenez et al. |
| 2003/0144623 A1 | 7/2003 | Heath et al. |
| 2003/0153970 A1 | 8/2003 | Rao et al. |
| 2003/0171708 A1 | 9/2003 | Segura et al. |
| 2003/0176831 A1 | 9/2003 | Gellman et al. |
| 2003/0181842 A1 | 9/2003 | Gellman |
| 2003/0181887 A1 | 9/2003 | Castillo Deniega et al. |
| 2003/0191452 A1 | 10/2003 | Meglin et al. |
| 2003/0195456 A1 | 10/2003 | Robertson |
| 2003/0195537 A1 | 10/2003 | Dubrul et al. |
| 2003/0199805 A1 | 10/2003 | McWeeney |
| 2003/0216710 A1 | 11/2003 | Hurt |
| 2003/0224033 A1 | 12/2003 | Li et al. |
| 2004/0019358 A1 | 1/2004 | Kear |
| 2004/0054315 A1 | 3/2004 | Levin et al. |
| 2004/0054351 A1 | 3/2004 | Deniega et al. |
| 2004/0057037 A1 | 3/2004 | Ohishi et al. |
| 2004/0073194 A1 | 4/2004 | Olsen et al. |
| 2004/0097891 A1 | 5/2004 | Bolmsjo |
| 2004/0129616 A1 | 7/2004 | Mori et al. |
| 2004/0143209 A1 | 7/2004 | Liu et al. |
| 2004/0147871 A1 | 7/2004 | Burnett |
| 2004/0167415 A1 | 8/2004 | Gelfand et al. |
| 2004/0167634 A1 | 8/2004 | Atala et al. |
| 2004/0193098 A1 | 9/2004 | Wentling et al. |
| 2005/0042240 A1 | 2/2005 | Utterberg et al. |
| 2005/0049575 A1 | 3/2005 | Snell et al. |
| 2005/0049577 A1 | 3/2005 | Snell et al. |
| 2005/0101941 A1 | 5/2005 | Hakky et al. |
| 2005/0107736 A1 | 5/2005 | Landman et al. |
| 2005/0124969 A1 | 6/2005 | Fitzgerald et al. |
| 2005/0124978 A1 | 6/2005 | Kim |
| 2005/0177102 A1 | 8/2005 | Hart et al. |
| 2005/0187564 A1 | 8/2005 | Jayaraman |
| 2005/0240141 A1 | 10/2005 | Aliski et al. |
| 2005/0240280 A1 | 10/2005 | Aliski et al. |
| 2005/0256441 A1 | 11/2005 | Lotan et al. |
| 2005/0256447 A1 | 11/2005 | Richardson et al. |
| 2005/0288722 A1 | 12/2005 | Eigler et al. |
| 2006/0015015 A1 | 1/2006 | Kawamoto et al. |
| 2006/0052879 A1 | 3/2006 | Kolb |
| 2006/0074388 A1 | 4/2006 | Dextradeur et al. |
| 2006/0074409 A1 | 10/2006 | Schuermann |
| 2006/0229553 A1 | 10/2006 | Hammack et al. |
| 2006/0229573 A1 | 10/2006 | Lamborne |
| 2006/0259151 A1 | 11/2006 | Ward |
| 2006/0271019 A1 | 11/2006 | Stoller et al. |
| 2007/0010797 A1 | 1/2007 | Nishtala et al. |
| 2007/0010798 A1 | 1/2007 | Stoller et al. |
| 2007/0055198 A1 | 3/2007 | O'Mahony et al. |
| 2007/0073271 A1 | 3/2007 | Brucker et al. |
| 2007/0088333 A1 | 4/2007 | Levin et al. |
| 2007/0112302 A1 | 5/2007 | Yu |
| 2007/0197957 A1 | 8/2007 | Hunter et al. |
| 2007/0208291 A1 | 9/2007 | Patel |
| 2007/0213665 A1 | 9/2007 | Curtin et al. |
| 2007/0219488 A1 | 9/2007 | Francescatti |
| 2007/0255230 A1 | 11/2007 | Gross et al. |
| 2008/0051678 A1 | 2/2008 | Lindahl |
| 2008/0051691 A1 | 2/2008 | Dragoon et al. |
| 2008/0058650 A1 | 3/2008 | Saadat et al. |
| 2008/0097463 A1 | 4/2008 | House |
| 2008/0119907 A1 | 5/2008 | Stahmann |
| 2008/0142023 A1 | 6/2008 | Schmid et al. |
| 2008/0183299 A1 | 7/2008 | Monga et al. |
| 2008/0215247 A1 | 9/2008 | Tonelli et al. |
| 2008/0243091 A1 | 10/2008 | Humphreys et al. |
| 2008/0255550 A1 | 10/2008 | Bell |
| 2008/0281291 A1 | 11/2008 | Tihon et al. |
| 2008/0288082 A1 | 11/2008 | Deal |
| 2008/0312550 A1 | 12/2008 | Nishtala et al. |
| 2009/0024091 A1 | 1/2009 | Li et al. |
| 2009/0030370 A1 | 1/2009 | Nishtala et al. |
| 2009/0030435 A1 | 1/2009 | Burnett et al. |
| 2009/0043229 A1 | 2/2009 | Dunn et al. |
| 2009/0088677 A1 | 4/2009 | Cohen |
| 2009/0093748 A1 | 4/2009 | Patterson et al. |
| 2009/0105719 A1 | 4/2009 | Honey et al. |
| 2009/0143713 A1 | 6/2009 | Van Dam et al. |
| 2009/0162530 A1 | 6/2009 | Nesbitt |
| 2009/0171137 A1 | 7/2009 | Farnan et al. |

(56) References Cited

U.S. PATENT DOCUMENTS

| | | |
|---|---|---|
| 2009/0171241 A1 | 7/2009 | Garcia et al. |
| 2009/0281507 A1 | 11/2009 | Humphreys |
| 2009/0318844 A1 | 12/2009 | Burnett |
| 2010/0057000 A1 | 3/2010 | Melsheimer et al. |
| 2010/0081148 A1 | 4/2010 | Singbartl et al. |
| 2010/0086580 A1 | 4/2010 | Nyman et al. |
| 2010/0121159 A1 | 5/2010 | Burnett et al. |
| 2010/0204682 A1 | 8/2010 | Tanghoj et al. |
| 2010/0241240 A1 | 9/2010 | Willard et al. |
| 2010/0261985 A1 | 10/2010 | Cohen-Solal et al. |
| 2010/0298857 A1 | 11/2010 | Zook et al. |
| 2010/0312163 A1 | 12/2010 | Forsell |
| 2011/0009799 A1 | 1/2011 | Mullick et al. |
| 2011/0009831 A1 | 1/2011 | Burkholz et al. |
| 2011/0015558 A1 | 1/2011 | Kaye et al. |
| 2011/0077605 A1 | 3/2011 | Karpowicz et al. |
| 2011/0089111 A1 | 4/2011 | Mori et al. |
| 2011/0098683 A1 | 4/2011 | Mita et al. |
| 2011/0118537 A1 | 5/2011 | Wampler |
| 2011/0132838 A1 | 6/2011 | Curtis et al. |
| 2011/0208319 A1 | 8/2011 | Laster |
| 2011/0230950 A1 | 9/2011 | Knapp |
| 2011/0238163 A1 | 9/2011 | Andrews et al. |
| 2011/0269167 A1 | 11/2011 | Bene |
| 2011/0276024 A1 | 11/2011 | Randolph et al. |
| 2011/0282264 A1 | 11/2011 | Hurt |
| 2011/0301553 A1 | 12/2011 | Goral et al. |
| 2011/0301662 A1 | 12/2011 | Bar-Yoseph et al. |
| 2011/0320008 A1 | 12/2011 | Teague et al. |
| 2012/0029937 A1 | 2/2012 | Neftel et al. |
| 2012/0042427 A1 | 2/2012 | Messier |
| 2012/0053700 A1 | 3/2012 | Rickner |
| 2012/0078226 A1 | 3/2012 | Latere Dwan'isa et al. |
| 2012/0083899 A1 | 4/2012 | Whitmore, III |
| 2012/0107420 A1 | 5/2012 | Breit et al. |
| 2012/0136343 A1 | 5/2012 | Burnett |
| 2012/0154264 A1 | 6/2012 | Wang et al. |
| 2012/0165641 A1 | 6/2012 | Burnett et al. |
| 2012/0179144 A1 | 7/2012 | Carleo |
| 2012/0179145 A1 | 7/2012 | Nishtala et al. |
| 2012/0220926 A1 | 8/2012 | Soykan et al. |
| 2012/0238802 A1 | 9/2012 | Knight et al. |
| 2012/0265020 A1 | 10/2012 | Pandey et al. |
| 2012/0277155 A1 | 11/2012 | VanAntwerp et al. |
| 2012/0316656 A1 | 12/2012 | Deal et al. |
| 2013/0030262 A1 | 1/2013 | Burnett et al. |
| 2013/0066166 A1 | 3/2013 | Burnett et al. |
| 2013/0085468 A1 | 4/2013 | Buydenok |
| 2013/0090648 A1 | 4/2013 | Nagale et al. |
| 2013/0131621 A1 | 5/2013 | Van Holten et al. |
| 2013/0138077 A1 | 5/2013 | O'Day |
| 2013/0150828 A1 | 6/2013 | Conway |
| 2013/0172807 A1 | 7/2013 | Cruz |
| 2013/0172881 A1 | 7/2013 | Hill et al. |
| 2013/0184545 A1 | 7/2013 | Blomqvist et al. |
| 2013/0187563 A1 | 7/2013 | Sasai et al. |
| 2013/0197471 A1 | 8/2013 | Williams et al. |
| 2013/0199998 A1 | 8/2013 | Kelly et al. |
| 2013/0218135 A1 | 8/2013 | Dein |
| 2013/0231640 A1 | 9/2013 | Terry et al. |
| 2013/0231752 A1 | 9/2013 | Rosenbaum et al. |
| 2013/0253409 A1 | 9/2013 | Burnett |
| 2013/0267845 A1 | 10/2013 | Howle et al. |
| 2013/0274644 A1 | 10/2013 | Hertz |
| 2013/0274783 A1 | 10/2013 | Wynberg |
| 2013/0303865 A1 | 11/2013 | Rebec et al. |
| 2013/0303961 A1 | 11/2013 | Wolff et al. |
| 2013/0304082 A1 | 11/2013 | Aklog et al. |
| 2013/0317322 A1 | 11/2013 | Andrijauskas |
| 2013/0331824 A1 | 12/2013 | Kim |
| 2013/0345670 A1 | 12/2013 | Rajagopalan et al. |
| 2014/0031773 A1 | 1/2014 | Mikkaichi |
| 2014/0031787 A1 | 1/2014 | Burnes et al. |
| 2014/0039375 A1 | 2/2014 | Jimenez et al. |
| 2014/0058316 A1 | 2/2014 | Gupta et al. |
| 2014/0073926 A1 | 3/2014 | Rajendran et al. |
| 2014/0074144 A1 | 3/2014 | Shrivastava et al. |
| 2014/0135941 A1 | 5/2014 | Smouse et al. |
| 2014/0142539 A1 | 5/2014 | Salinas et al. |
| 2014/0148648 A1 | 5/2014 | Tycast et al. |
| 2014/0148754 A1 | 5/2014 | Soykan et al. |
| 2014/0155818 A1 | 6/2014 | Salinas et al. |
| 2014/0188248 A1 | 7/2014 | Gandhi |
| 2014/0188249 A1 | 7/2014 | Pendleton et al. |
| 2014/0228801 A1 | 8/2014 | Keeling |
| 2014/0275984 A1 | 9/2014 | Hermann et al. |
| 2014/0276341 A1 | 9/2014 | Ludin et al. |
| 2014/0276628 A1 | 9/2014 | Gandras et al. |
| 2014/0343515 A1 | 11/2014 | Sylvester et al. |
| 2014/0364820 A1 | 12/2014 | Solazzo et al. |
| 2015/0011855 A1 | 1/2015 | Burnett et al. |
| 2015/0011928 A1 | 1/2015 | Burnett |
| 2015/0017682 A1 | 1/2015 | Adam |
| 2015/0065783 A1 | 3/2015 | Buelna |
| 2015/0080844 A1 | 3/2015 | Donovan et al. |
| 2015/0094548 A1 | 4/2015 | Sabatini et al. |
| 2015/0094644 A1 | 4/2015 | Lenihan et al. |
| 2015/0094696 A1 | 4/2015 | Adams, Jr. et al. |
| 2015/0100009 A1 | 4/2015 | Bearss |
| 2015/0134073 A1 | 5/2015 | Tang et al. |
| 2015/0164370 A1 | 6/2015 | Wabel et al. |
| 2015/0194052 A1 | 7/2015 | Sagan et al. |
| 2015/0223953 A1 | 8/2015 | Pendleton et al. |
| 2015/0224241 A1 | 8/2015 | Fontanazzi et al. |
| 2015/0273120 A1 | 10/2015 | Zamarripa et al. |
| 2015/0283362 A1 | 10/2015 | Shelton et al. |
| 2015/0290411 A1 | 10/2015 | Warrington et al. |
| 2015/0306364 A1 | 10/2015 | Shevgoor |
| 2015/0352339 A1 | 12/2015 | Wang |
| 2016/0045302 A1 | 2/2016 | Nishio et al. |
| 2016/0051176 A1 | 2/2016 | Ramos et al. |
| 2016/0058489 A1 | 3/2016 | Fischell et al. |
| 2016/0183819 A1 | 6/2016 | Burnett et al. |
| 2016/0213881 A9 | 7/2016 | Adams, Jr. et al. |
| 2016/0303303 A1 | 10/2016 | Rovatti et al. |
| 2016/0310711 A1 | 10/2016 | Luxon et al. |
| 2016/0367747 A1 | 12/2016 | Loske |
| 2017/0020724 A1 | 1/2017 | Burnett et al. |
| 2017/0021128 A1 | 1/2017 | Erbey, II et al. |
| 2017/0095641 A1 | 4/2017 | Scarpine et al. |
| 2017/0113000 A1 | 4/2017 | Tobescu et al. |
| 2017/0119519 A1 | 5/2017 | Sambusseti et al. |
| 2017/0128639 A1 | 5/2017 | Erbey, II et al. |
| 2017/0128654 A1 | 5/2017 | Feld |
| 2017/0136222 A1 | 5/2017 | Hakim et al. |
| 2017/0196576 A1 | 7/2017 | Long et al. |
| 2017/0197028 A1 | 7/2017 | Goldsmith |
| 2017/0232153 A1 | 8/2017 | Babu et al. |
| 2017/0251977 A1 | 9/2017 | Fang |
| 2017/0266414 A1 | 9/2017 | Rocha-Singh et al. |
| 2017/0325927 A1 | 11/2017 | Gobel |
| 2017/0348507 A1 | 12/2017 | Erbey, II et al. |
| 2017/0348512 A1 | 12/2017 | Orr et al. |
| 2017/0367636 A1 | 12/2017 | Mantinband et al. |
| 2018/0001055 A1 | 1/2018 | Utas et al. |
| 2018/0116751 A1 | 5/2018 | Schwartz et al. |
| 2018/0117288 A1 | 5/2018 | Lindsay et al. |
| 2018/0147330 A1 | 5/2018 | Peng et al. |
| 2018/0169313 A1 | 6/2018 | Schwammenthal et al. |
| 2018/0177458 A1 | 6/2018 | Burnett |
| 2018/0193618 A1 | 7/2018 | Erbey, II et al. |
| 2018/0207412 A1 | 7/2018 | Malek et al. |
| 2019/0030303 A1 | 1/2019 | Holman et al. |
| 2019/0091442 A1 | 3/2019 | Erbey, II et al. |
| 2019/0105465 A1 | 4/2019 | Erbey, II et al. |
| 2019/0167958 A1* | 6/2019 | Walish ............... A61M 27/008 |
| 2019/0201662 A1 | 7/2019 | Lad et al. |
| 2019/0247615 A1 | 8/2019 | Bishawi |
| 2020/0001045 A1 | 1/2020 | McIntyre |

(56) References Cited

U.S. PATENT DOCUMENTS

| | | |
|---|---|---|
| 2020/0094017 A1 | 3/2020 | Erbey, II et al. |
| 2021/0178133 A1 | 6/2021 | Walish et al. |

FOREIGN PATENT DOCUMENTS

| | | |
|---|---|---|
| CA | 2205473 C | 6/2006 |
| CN | 2175619 Y | 8/1994 |
| CN | 2562776 Y | 7/2003 |
| CN | 2588940 Y | 12/2003 |
| CN | 1479596 A | 3/2004 |
| CN | 2753382 Y | 1/2006 |
| CN | 2928043 Y | 8/2007 |
| CN | 101224148 A | 7/2008 |
| CN | 101426540 A | 5/2009 |
| CN | 201814968 U | 5/2011 |
| CN | 102176928 A | 9/2011 |
| CN | 202459720 U | 10/2012 |
| CN | 202526754 U | 11/2012 |
| CN | 202802478 U | 3/2013 |
| CN | 103096964 A | 5/2013 |
| CN | 103203062 A | 7/2013 |
| CN | 103841905 A | 6/2014 |
| CN | 203777060 U | 8/2014 |
| CN | 203842151 U | 9/2014 |
| CN | 204158867 U | 2/2015 |
| CN | 204246651 U | 4/2015 |
| CN | 204446944 U | 7/2015 |
| CN | 205126495 U | 4/2016 |
| CN | 106237417 A | 12/2016 |
| CN | 106473847 A | 3/2017 |
| CN | 106693092 A | 5/2017 |
| CN | 107261294 A | 10/2017 |
| DE | 102012016049 A1 | 2/2014 |
| EP | 873760 A1 | 10/1998 |
| EP | 1011803 B1 | 9/2004 |
| EP | 1980292 A2 | 10/2008 |
| EP | 3488897 A1 | 5/2019 |
| EP | 3970775 A1 | 3/2022 |
| FR | 3052671 A1 | 12/2017 |
| JP | 59111748 A | 6/1984 |
| JP | H42361 A | 1/1992 |
| JP | 10504469 A | 5/1998 |
| JP | 2002510536 A | 4/2002 |
| JP | 2002291879 A | 10/2002 |
| JP | 2002537893 A | 11/2002 |
| JP | 2002538888 A | 11/2002 |
| JP | 2003530165 A | 10/2003 |
| JP | 2004215787 A | 8/2004 |
| JP | 2006516214 A | 6/2006 |
| JP | 2006526464 A | 11/2006 |
| JP | 2009505802 A | 2/2009 |
| JP | 2009238520 A | 10/2009 |
| JP | 2009537256 A | 10/2009 |
| JP | 2010005282 A | 1/2010 |
| JP | 2010119737 A | 6/2010 |
| JP | 2010230618 A | 10/2010 |
| JP | 2013149498 A | 1/2012 |
| JP | 2012505022 A | 3/2012 |
| JP | 2012530575 A | 12/2012 |
| JP | 2014176689 A | 9/2014 |
| RU | 2113245 C1 | 6/1998 |
| RU | 2300399 C1 | 6/2007 |
| RU | 149161 U1 | 12/2014 |
| TW | M540625 U | 5/2017 |
| WO | 9529716 A1 | 11/1995 |
| WO | 9716218 A1 | 5/1997 |
| WO | 9816171 A1 | 4/1998 |
| WO | 9850088 A1 | 11/1998 |
| WO | 9054701 A1 | 9/2000 |
| WO | 0160260 A1 | 8/2001 |
| WO | 6558350 A1 | 12/2001 |
| WO | 03017870 A1 | 3/2003 |
| WO | 2004064681 A1 | 8/2004 |
| WO | 2006017439 A2 | 2/2006 |
| WO | 2006023589 A2 | 3/2006 |
| WO | 2006044621 A2 | 4/2006 |
| WO | 2007001978 A2 | 1/2007 |
| WO | 2007027830 A1 | 3/2007 |
| WO | 2008066625 A1 | 6/2008 |
| WO | 2010082197 A2 | 7/2010 |
| WO | 2011109570 A2 | 9/2011 |
| WO | 2011139498 A1 | 11/2011 |
| WO | 2013029622 A1 | 3/2013 |
| WO | 2014025367 A1 | 2/2014 |
| WO | 2014043650 A2 | 3/2014 |
| WO | 2014062225 A1 | 4/2014 |
| WO | 2015105916 A1 | 7/2015 |
| WO | 2015157467 A1 | 10/2015 |
| WO | 2015198333 A1 | 12/2015 |
| WO | 2016049654 A1 | 3/2016 |
| WO | 2016103256 A1 | 6/2016 |
| WO | 2017015345 A2 | 1/2017 |
| WO | 2017015351 A2 | 1/2017 |
| WO | 2017019974 A1 | 2/2017 |
| WO | 2017087182 A1 | 5/2017 |
| WO | 2018186781 A1 | 10/2018 |
| WO | 2018200050 A1 | 11/2018 |
| WO | 2019038730 A1 | 2/2019 |
| WO | 2020236748 A1 | 11/2020 |

OTHER PUBLICATIONS

Burr et al.; "Urinary catheter blockage depends on urine pH, calcium and rate of flow"; Spinal Cord; 1997; p. 521-525; vol. 35.

Clinical Practice Guidelines for Chronic Kidney Disease: Evaluation, Classification and Stratification; National Kidney Foundation; Am. J. Kidney Dis.; 2002; p. S1-S266; Suppl. 1.

"The Criteria Committee of the New York Heart Association", (1994), Nomenclature and Criteria for Diagnosis of Diseases of the Heart and Great Vessels, (9th ed.), Boston: Little, Brown & Co. p. 253-256 (Abstract).

Harris et al., "Relationship between patients' outcomes and the changes in serum creatinine and urine output and RIFLE classification in a large critical care cohort database", Kidney International, 2015, p. 369-377, vol. 88.

Jessup et al.; "The Cardiorenal Syndrome—Do We Need a Change of Strategy or a Change of Tactics?"; Journal of the American College of Cardiology; 2009; p. 597-599; vol. 53:7.

Mardis et al., "Comparative Evaluation of Materials Used for Internal Ureteral Stents", Journal of Endourology, 1993, pp. 105-115, vol. 7:2.

Mullens et al.; "Importance of Venous Congestion for Worsening of Renal Function in Advanced Decompensated Heart Failure"; Journal of the American College of Cardiology; 2009; p. 589-596; vol. 53:7.

Peters et al.; "Short and Long-Term Effects of the Angiotensin II Receptor Blocker Irbesartan on Intradialytic Central Hemodynamics: A Randomized Double-Blind Placebo-Controlled One-Year Intervention Trial (the SAFIR Study)"; PLoS One; Jun. 1, 2015; p. 1-22.

"Standard Specification for Ureteral Stents", ASTM International, 2014, Designation F1828-97, p. 1-6.

Verbrugge et al.; "The kidney in congestive heart failure: are natriuresis, sodium, and diuretics really the good, the bad and the ugly?"; European Journal of Heart Failure; 2014; p. 133-142; vol. 16.

Wolf, Jr. et al.; "Comparative Ureteral Microanatomy"; Journal of Endourology; 1996; p. 527-531; vol. 10:6.

Zelenko et al.; "Normal Ureter Size on Unenhanced Helical CT"; American Journal of Roentgenology; 2004; p. 1039-1041; vol. 182.

Johnson et al., "Clinical Practice Guidelines for Chronic Kidney Disease in Adults: Part I. Definition, Disease Stages, Evaluation, Treatment, and Risk Factors", American Family Physician, Sep. 1, 2004, p. 869-876, vol. 70 Issue 5.

U.S. Pat. No. 10,307,564 / U.S. Appl. No. 15/214,955, "Ureteral and Bladder Catheters and Methods of Inducing Negative Pressure to Increase Renal Perfusion", Jun. 4, 20019 / filed Jul. 20, 2016.

(56) References Cited

OTHER PUBLICATIONS

U.S. Pat. No. 9,744,331 / U.S. Appl. No. 15/215,081, "Ureteral and Bladder Catheters and Methods of Inducing Negative Pressure to Increase Renal Perfusion", Aug. 29, 2017 / filed Jul. 20, 2016.
U.S. Pat. No. 10,512,713 / U.S. Appl. No. 15/411,884, "Method of Removing Excess Fluid from a Patient with Hemodilution", Dec. 24, 2019 / filed Jan. 20, 2017.
U.S. Pat. No. 10/601,664 / U.S. Appl. No. 15/673,706, "Ureteral and Bladder Catheters and Methods of Inducing Negative Pressure to Increase Renal Perfusion", Apr. 7, 2020 / filed Aug. 10, 2017.
U.S. Pat. No. 10,765,834 / U.S. Appl. No. 15/687,064, "Ureteral and Bladder Catheters and Methods of Inducing Negative Pressure to Increase Renal Perfusion", Sep. 8, 2020 / filed Aug. 25, 2017.
U.S. Appl. No. 15/687,083 "Ureteral and Bladder Catheters and Methods of Inducing Negative Pressure to Increase Renal Perfusion", filed Aug. 25, 2017.
U.S. Appl. No. 15/879,976, "Ureteral and Bladder Catheters and Methods of Inducing Negative Pressure to Increase Renal Perfusion", filed Jan. 25, 2018.
U.S. Appl. No. 15/879,869, "Catheter Device and Method for Inducing Negative Pressure in a Patient's Bladder", filed Jan. 25, 2018.
U.S. Appl. No. 15/745,823, "Catheter Device and Method for Inducing Negative Pressure in a Patient's Bladder", filed Jul. 20, 20106.
U.S. Appl. No. 15/879,770, "Systems, Kits and Methods for Inducing Negative Pressure to Increase Renal Function", filed Jan. 25, 2018.
U.S. Appl. No. 16/012,233, "Ureteral and Bladder Catheters and Methods of Inducing Negative Pressure to Increase Renal Perfusion", filed Jun. 19, 2018.
U.S. Appl. No. 16/036,971, "Ureteral and Bladder Catheters and Methods of Inducing Negative Pressure to Increase Renal Perfusion", filed Jul. 17, 2018.
U.S. Appl. No. 16/206,207, "Percutaneous Ureteral Catheter", filed Nov. 30, 2018.
U.S. Appl. No. 16/206,389, "Coated Ureteral Catheter or Ureteral Stent and Method", filed Nov. 30, 2018.
U.S. Pat. No. 10,493,232 / U.S. Appl. No. 16/205,987, "Ureteral Catheters, Bladder Catheters, Systems, Kits and Methods for Inducing Negative Pressure to Increase Renal Function", Dec. 3, 2019 / filed Nov. 30, 2018.
U.S. Pat. No. 10,426,919 / U.S. Appl. No. 16/257,791, "Systems and Methods for Inducing Negative Pressure in a Portion of a Urinary Tract of a Patient", Oct. 1, 2019 filed Jan. 25, 2019.
U.S. Appl. No. 16/390,154, "Ureteral and Bladder Catheters and Methods of Inducing Negative Pressure to Increase Renal Perfusion", filed Apr. 22, 2019.
U.S. Appl. No. 16/542,680, "Systems and Methods for Inducing Negative Pressure in a Portion of a Urinary Tract of a Patient", filed Aug. 16, 2019.
U.S. Appl. No. 16/670,249, "Method of Removing Excess Fluids from a Patient with Hemodilution", filed Oct. 31, 2019.
U.S. Appl. No. 16/662,536, "Ureteral Catheters, Bladder Catheters, Systems, Kits and Methods for Inducing Negative Pressure to Increase Renal Function", filed Oct. 24, 2019.
U.S. Appl. No. 16/662,212, "Catheter and Method for Inducing Negative Pressure in a Patient's Bladder", filed Oct. 24, 2019.
U.S. Appl. No. 16/696,026, "Coated and/or Impregnated Ureteral Catheter or Stent and Method", filed Nov. 26, 2019.
U.S. Appl. No. 16/850,052, "Method of Removing Excess Fluid from a Patient with Venous Congestion", filed Apr. 16, 2020.
U.S. Appl. No. 16/820,781, "Ureteral and Bladder Catheters and Methods of Inducing Negative Pressure to Increase Renal Perfusion", filed Mar. 17, 2020.
U.S. Appl. No. 16/640,210, "Indwelling Pump for Facilitating Removal of Urine from the Urinary Tract", filed Aug. 24, 2018.
U.S. Appl. No. 16/817,773, "Ureteral and Bladder Catheters and Methods of Inducing Negative Pressure to Increase Renal Perfusion", filed Mar. 13, 2020.
U.S. Appl. No. 16/826,347, "Ureteral Catheters, Bladder Catheters, Systems, Kits and Methods for Inducing Negative Pressure to Increase Renal Function", filed Mar. 23, 2020.
U.S. Appl. No. 16/835,973, "Catheter Device and Method for Inducing Negative Pressure in a Patient's Bladder", filed Mar. 31, 2020.
U.S. Appl. No. 16/856,339, "Pump Assembly and System for Inducing Negative Pressure in a Portion of a Urinary Tract of a Patient", filed Apr. 23, 2020.
U.S. Appl. No. 16/872,965, "Ureteral and Bladder Catheters and Methods of Inducing Negative Pressure to Increase Renal Perfusion", filed May 12, 2020.
U.S. Appl. No. 17/089,757, "Catheter Device and Method for Inducing Negative Pressure in a Patient's Bladder", filed Nov. 5, 2020.
Quadra-Coil | Olympus America | Medical, Ureteral Stents, https://www.medical.olympusamerica.com/products/quadra-coil (downloaded from the Internet Aug. 31, 2022) 2 pages.
Stents—Urology | Olympus America | Medical. Ureteral Stents, https://www.medical.olympusamerica.com/products/stents-Urology (downloaded from the Internet Aug. 31, 2022) 2 pages.
Ureteral stent—Quadra-Coil—Olympus Medical Europa, https://www.medicalexpo.com/prod/olympus-medical-europa/product-69587-661607.html (downloaded from the Internet Aug. 31, 2022) 5 pages.
Mordi et al.,"Renal and Cardiovascular Effects of Sodium-glucose contransporter 2 (SGLT2) inhibition in combination with loop Diuretics in diabetic patients with Chronic Heart Failure (RECEDE-CHF): protocol for a randomised controlled double-blind cross-over trial", BMJ Open, 2017, pp. 1-9.
Damman et al., "Increased Central Venous Pressure Is Associated With Impaired Renal Function and Mortality in a Broad Spectrum of Patients with Cardiovascular Disease", 2009, Journal of the American College of Cardiology, vol. 53:7, pp. 582-588.
Dixon et al., "The musculature of the human renal calices, pelvis and upper ureter", J, Anat., 1982, vol. 135, pp. 129-137.
Gregersen et al., "Regional Differences Exist in Elastic Wall Properties in the Ureter", SJUN, 1996, vol. 30, pp. 343-348.
Kiil, "Urinary Flow and Ureteral Peristalsis" in: Lutzeyer W., Melchior H. (Eds.) Urodynamics, 1973, Springer, Berlin, Heidelberg (pp. 57-70).
Lala et al.,"Relief and Recurrence of Congestion During and After Hospitalization for Acute Heart Failure: Insights from Dose-AHF and Carress-HF", Circ Heart Fail, 2015, vol. 8:4, pp. 741-748.
Legrand et al. "Association between systemic hemodynamics and septic acute kidney injury in critically ill patients: a retrospective observation study", Critical Care, 2013, vol. 17:R278, pp. 1-8.
Nohria et al., "Cardiorenal Interactions Insights from the Escape Trial", Heart Failure, 2008, vol. 51:13, pp. 1268-1274.
Uthoff et al., "Central venous pressure and impaired renal function in patients with acute heart failure", European Journal of Heart Failure, 2011. vol. 13, pp. 432-439.
Walker, "Annals of Surgery" 1913, Lippincott Williams & Wilkins, p. 58, Figures 3 and 9.
Webb, "Percutaneous Renal Surgery: A Practical Clinical Handbook", 2016, Springer International Publishing, Switzerland, p. 92.
Woodburne et al., "The Uretal Lumen during Peristalsis", Am. J. Anat., 1972. vol. 133, pp. 255-258.

* cited by examiner

URETERAL AND BLADDER CATHETERS AND METHODS OF INDUCING NEGATIVE PRESSURE TO INCREASE RENAL PERFUSION

CROSS REFERENCE TO RELATED APPLICATIONS

This application is a continuation of U.S. patent application Ser. No. 15/687,083, filed Aug. 25, 2017, which is a continuation-in-part of U.S. patent application Ser. No. 15/411,884 filed Jan. 20, 2017, now issued as U.S. Pat. No. 10,512,713, which is a continuation-in-part of U.S. patent application Ser. No. 15/214,955 filed Jul. 20, 2016, now issued as U.S. Pat. No. 10,307,564, which claims the benefit of U.S. Provisional Application No. 62/300,025 filed Feb. 25, 2016, U.S. Provisional Application No. 62/278,721, filed Jan. 14, 2016, U.S. Provisional Application No. 62/260,966 filed Nov. 30, 2015, and U.S. Provisional Application No. 62/194,585, filed Jul. 20, 2015, each of which is incorporated herein by reference in its entirety.

BACKGROUND

Technical Field

The present disclosure relates to methods and devices for treating impaired renal function across a variety of disease states and, in particular, to catheter devices, assemblies, and methods for collection of urine and/or inducement of negative pressure in the ureters and/or kidneys.

Background

The renal or urinary system includes a pair of kidneys, each kidney being connected by a ureter to the bladder, and a urethra for draining urine produced by the kidneys from the bladder. The kidneys perform several vital functions for the human body including, for example, filtering the blood to eliminate waste in the form of urine. The kidneys also regulate electrolytes (e.g., sodium, potassium and calcium) and metabolites, blood volume, blood pressure, blood pH, fluid volume, production of red blood cells, and bone metabolism. Adequate understanding of the anatomy and physiology of the kidneys is useful for understanding the impact that altered hemodynamics other fluid overload conditions have on their function.

In normal anatomy, the two kidneys are located retroperitoneally in the abdominal cavity. The kidneys are bean-shaped encapsulated organs. Urine is formed by nephrons, the functional unit of the kidney, and then flows through a system of converging tubules called collecting ducts. The collecting ducts join together to form minor calyces, then major calyces, which ultimately join near the concave portion of the kidney (renal pelvis). A major function of the renal pelvis is to direct urine flow to the ureter. Urine flows from the renal pelvis into the ureter, a tube-like structure that carries the urine from the kidneys into the bladder. The outer layer of the kidney is called the cortex, and is a rigid fibrous encapsulation. The interior of the kidney is called the medulla. The medulla structures are arranged in pyramids.

Each kidney is made up of approximately one million nephrons. A schematic drawing of a nephron 1102 is shown in FIG. 39. Each nephron includes the glomerulus 1110, Bowman's capsule 1112, and tubules 1114. The tubules 1114 include the proximal convoluted tubule 1116, the loop of Henle 1118, the distal convoluted tubule 1120, and the collecting duct 1122. The nephrons 1102 contained in the cortex layer of the kidney are distinct from the anatomy of those contained in the medulla. The principal difference is the length of the loop of Henle 1118. Medullary nephrons contain a longer loop of Henle, which, under normal circumstances, allows greater regulation of water and sodium reabsorption than in the cortex nephrons.

The glomerulus is the beginning of the nephron, and is responsible for the initial filtration of blood. Afferent arterioles pass blood into the glomerular capillaries, where hydrostatic pressure pushes water and solutes into Bowman's capsule. Net filtration pressure is expressed as the hydrostatic pressure in the afferent arteriole minus the hydrostatic pressure in Bowman's space minus the osmotic pressure in the efferent arteriole.

Net Filtration Pressure=Hydrostatic Pressure (Afferent Arteriole)−Hydrostatic Pressure (Bowman's Space)−Osmotic Pressure (Efferent Arteriole)  (Equation 1)

The magnitude of this net filtration pressure defined by Equation 1 determines how much ultra-filtrate is formed in Bowman's space and delivered to the tubules. The remaining blood exits the glomerulus via the efferent arteriole. Normal glomerular filtration, or delivery of ultra-filtrate into the tubules, is about 90 ml/min/1.73 m$^2$.

The glomerulus has a three-layer filtration structure, which includes the vascular endothelium, a glomerular basement membrane, and podocytes. Normally, large proteins such as albumin and red blood cells, are not filtered into Bowman's space. However, elevated glomerular pressures and mesangial expansion create surface area changes on the basement membrane and larger fenestrations between the podocytes allowing larger proteins to pass into Bowman's space.

Ultra-filtrate collected in Bowman's space is delivered first to the proximal convoluted tubule. Re-absorption and secretion of water and solutes in the tubules is performed by a mix of active transport channels and passive pressure gradients. The proximal convoluted tubules normally reabsorb a majority of the sodium chloride and water, and nearly all glucose and amino acids that were filtered by the glomerulus. The loop of Henle has two components that are designed to concentrate wastes in the urine. The descending limb is highly water permeable and reabsorbs most of the remaining water. The ascending limb reabsorbs 25% of the remaining sodium chloride, creating a concentrated urine, for example, in terms of urea and creatinine. The distal convoluted tubule normally reabsorbs a small proportion of sodium chloride, and the osmotic gradient creates conditions for the water to follow.

Under normal conditions, there is a net filtration of approximately 14 mmHg. The impact of venous congestion can be a significant decrease in net filtration, down to approximately 4 mmHg. See Jessup M., *The cardiorenal syndrome: Do we need a change of strategy or a change of tactics?*, JACC 53(7):597-600, 2009 (hereinafter "Jessup"). The second filtration stage occurs at the proximal tubules. Most of the secretion and absorption from urine occurs in tubules in the medullary nephrons. Active transport of sodium from the tubule into the interstitial space initiates this process. However, the hydrostatic forces dominate the net exchange of solutes and water. Under normal circumstances, it is believed that 75% of the sodium is reabsorbed back into lymphatic or venous circulation. However, because the kidney is encapsulated, it is sensitive to changes in hydrostatic pressures from both venous and lymphatic congestion. During venous congestion the retention of sodium and water can exceed 85%, further perpetuating the renal congestion. See Verbrugge et al., *The kidney in congestive heart failure: Are natriuresis, sodium, and diruetucs really the good, the bad and the ugly? European Journal of Heart Failure* 2014:16, 133-42 (hereinafter "Verbrugge").

Venous congestion can lead to a prerenal form of acute kidney injury (AKI). Prerenal AKI is due to a loss of perfusion (or loss of blood flow) through the kidney. Many clinicians focus on the lack of flow into the kidney due to shock. However, there is also evidence that a lack of blood flow out of the organ due to venous congestion can be a clinically important sustaining injury. See Damman K, *Importance of venous congestion for worsening renal function in advanced decompensated heart failure*, JACC 17:589-96, 2009 (hereinafter "Damman").

Prerenal AKI occurs across a wide variety of diagnoses requiring critical care admissions. The most prominent admissions are for sepsis and Acute Decompensated Heart Failure (ADHF). Additional admissions include cardiovascular surgery, general surgery, cirrhosis, trauma, burns, and pancreatitis. While there is wide clinical variability in the presentation of these disease states, a common denominator is an elevated central venous pressure. In the case of ADHF, the elevated central venous pressure caused by heart failure leads to pulmonary edema, and, subsequently, dyspnea in turn precipitating the admission. In the case of sepsis, the elevated central venous pressure is largely a result of aggressive fluid resuscitation. Whether the primary insult was low perfusion due to hypovolemia or sodium and fluid retention, the sustaining injury is the venous congestion resulting in inadequate perfusion.

Hypertension is another widely recognized state that creates perturbations within the active and passive transport systems of the kidney(s). Hypertension directly impacts afferent arteriole pressure and results in a proportional increase in net filtration pressure within the glomerulus. The increased filtration fraction also elevates the peritubular capillary pressure, which stimulates sodium and water re-absorption. See Verbrugge.

Because the kidney is an encapsulated organ, it is sensitive to pressure changes in the medullary pyramids. The elevated renal venous pressure creates congestion that leads to a rise in the interstitial pressures. The elevated interstitial pressures exert forces upon both the glomerulus and tubules. See Verburgge. In the glomerulus, the elevated interstitial pressures directly oppose filtration. The increased pressures increase the interstitial fluid, thereby increasing the hydrostatic pressures in the interstitial fluid and peritubular capillaries in the medulla of the kidney. In both instances, hypoxia can ensue leading to cellular injury and further loss of perfusion. The net result is a further exacerbation of the sodium and water re-absorption creating a negative feedback. See Verbrugge, 133-42. Fluid overload, particularly in the abdominal cavity is associated with many diseases and conditions, including elevated intra-abdominal pressure, abdominal compartment syndrome, and acute renal failure. Fluid overload can be addressed through renal replacement therapy. See Peters, C. D., *Short and Long-Term Effects of the Angiotensin II Receptor Blocker Irbesartanon Intradialytic Central Hemodynamics: A Randomized Double-Blind Placebo-Controlled One-Year Intervention Trial* (*the SAFIR Study*), PLoS ONE (2015) 10(6): e0126882. doi:10.1371/journal.pone.0126882 (hereinafter "Peters"). However, such a clinical strategy provides no improvement in renal function for patients with the cardiorenal syndrome. See Bart B, *Ultrafiltration in decompensated heart failure with cardiorenal syndrome, NEJM* 2012; 367:2296-2304 (hereinafter "Bart").

In view of such problematic effects of fluid retention, devices and methods for improving removal of urine from the urinary tract and, specifically for increasing quantity and quality of urine output from the kidneys, are needed.

SUMMARY

According to one example, a ureteral catheter includes a drainage lumen having a proximal portion configured to be positioned in at least a portion of a patient's urethra and/or bladder and a distal portion configured to be positioned in a patient's kidney, renal pelvis, and/or in the ureter adjacent to the renal pelvis. The distal portion includes a retention portion for maintaining positioning of the distal portion of the drainage lumen. The retention portion includes a plurality of sections, each section having one or more openings on a sidewall of the retention portion for permitting fluid flow into the drainage lumen. A total area of openings of a first section of the plurality of sections is less than a total area of openings of an adjacent second section of the plurality of sections. The second section is closer to a distal end of the drainage lumen than the first section.

According to another example, a ureteral catheter includes a drainage lumen having a proximal portion configured to be positioned in at least a portion of a patient's urethra and a distal portion configured to be positioned in a patient's kidney, renal pelvis, and/or in the ureter adjacent to the renal pelvis. The distal portion includes a retention portion for maintaining positioning of the distal portion of the drainage lumen. The retention portion includes a plurality of equal length sections of the drainage lumen, each of which has one or more openings on a sidewall of the drainage lumen for permitting fluid flow into the drainage lumen. A volumetric flow rate for fluid flowing into a proximal-most section of the plurality of sections is between about 1% and 60%, preferably between about 10% and 60%, and more preferably between about 30% and 60%, of a volumetric flow rate of fluid flowing through the proximal portion of the drainage lumen, as calculated based on a mass transfer shell balance evaluation for calculating volumetric flow rates through openings of the sections when a negative pressure of −45 mmHg is applied to a proximal end of the drainage lumens.

According to another example, a ureteral catheter includes: a drainage lumen having a proximal portion configured to be positioned in at least a portion of a patient's urethra and/or bladder and a distal portion configured to be positioned in a patient's kidney, renal pelvis, and/or in the ureter adjacent to the renal pelvis. The distal portion includes a coiled retention portion for maintaining positioning of the distal portion of the drainage lumen. The coiled retention portion includes: at least a first coil having a first diameter extending about an axis of the retention portion that is at least partially coextensive with a straight or curvilinear central axis of a portion of the drainage lumen proximal to the retention portion; and a plurality of sections, each of which includes one or more openings on a sidewall of the retention portion for permitting fluid flow into the drainage lumen. Along the plurality of sections, the sidewall of the retention portion includes a radially inwardly facing side and a radially outwardly facing side. A total area of the openings on the radially inwardly facing side is greater than a total area of the openings on the radially outwardly facing side. A total area of openings of a first section of the plurality of sections is less than a total area of openings of an adjacent second section of the plurality of sections, when the second section is closer to a distal end of the drainage lumen than the first section.

According to another example, a ureteral catheter includes a drainage lumen having a proximal portion configured to be positioned in at least a portion of a patient's urethra and/or bladder and a distal portion configured to be positioned in a patient's kidney, renal pelvis, and/or in the ureter adjacent to the renal pelvis. The distal portion includes a retention portion for maintaining positioning of the distal portion of the drainage lumen. The retention portion includes a plurality of openings on a sidewall of the retention portion for permitting fluid flow into the drainage lumen. An area of an opening of the plurality of openings which is closer to a proximal end of the retention portion is less than an area of an opening of the plurality of openings which is closer to the distal end of the drainage lumen.

According to another example, a system for inducing negative pressure in a portion of a urinary tract of a patient includes at least one ureteral catheter including a drainage lumen having a proximal portion configured to be positioned in at least a portion of a patient's urethra and/or bladder and a distal portion configured to be positioned in a patient's kidney, renal pelvis, and/or in the ureter adjacent to the renal pelvis. The distal portion includes a retention portion for maintaining positioning of the distal portion of the drainage lumen. The retention portion includes a plurality of equal length sections of the drainage lumen, each of which includes one or more openings on a sidewall of the drainage lumen for permitting fluid flow into the drainage lumen. The system also includes a pump in fluid communication with the drainage lumen of the at least one ureteral catheter. The pump is configured for inducing a positive and/or a negative pressure in a portion of the urinary tract of the patient to draw fluid into the drainage lumen through the openings of the sections of the retention portion. A total area of openings of a first section of the plurality of sections is less than a total area of openings of an adjacent second section of the plurality of sections, when the second section is closer to a distal end of the drainage lumen than the first section.

Non-limiting examples, aspects or embodiments of the present invention will now be described in the following numbered clauses:

Clause 1: A ureteral catheter, comprising: a drainage lumen comprising a proximal portion configured to be positioned in at least a portion of a patient's urethra and/or bladder and a distal portion configured to be positioned in a patient's kidney, renal pelvis, and/or in the ureter adjacent to the renal pelvis, the distal portion comprising a retention portion for maintaining positioning of the distal portion of the drainage lumen, the retention portion comprising a plurality of sections, each section comprising one or more openings on a sidewall of the retention portion for permitting fluid flow into the drainage lumen, wherein a total area of openings of a first section of the plurality of sections is less than a total area of openings of an adjacent second section of the plurality of sections, the second section being closer to a distal end of the drainage lumen than the first section.

Clause 2: The ureteral catheter of clause 1, wherein the proximal portion of the drainage lumen is essentially free of or free of openings.

Clause 3: The ureteral catheter of clause 1 or clause 2, wherein the proximal portion of the drainage lumen is configured to extend outside of the patient's body.

Clause 4: The ureteral catheter of any of clauses 1 to 3, further comprising a plurality of distance markings on the sidewall of the proximal portion of the drainage lumen to indicate how far the catheter is inserted into a urinary tract of a body of the patient.

Clause 5: The ureteral catheter of clause 4, further comprising a radiopaque band on the sidewall of the drainage lumen which is adjacent to a proximal end of the retention portion for identifying a location of the retention portion using fluoroscopic imaging, the radiopaque band having a different appearance than the distance markings when viewed by fluoroscopic imaging.

Clause 6: The ureteral catheter of any of clauses 1 to 5, wherein the drainage lumen is formed, at least in part, from one or more of copper, silver, gold, nickel-titanium alloy, stainless steel, titanium, polyurethane, polyvinyl chloride, polytetrafluoroethylene (PTFE), latex, and silicone.

Clause 7: The ureteral catheter of any of clauses 1 to 6, wherein the plurality of sections of the retention portion is biased in a coiled configuration, such that the retention portion comprises: at least a first coil having a first diameter; and at least a second coil having a second diameter, the first diameter being less than the second diameter, the second coil being closer to the distal end of the drainage lumen than the first coil, and wherein, prior to insertion into a patient's urinary tract, a portion of the drainage lumen that is proximal to the retention portion defines a straight or curvilinear central axis, and wherein, when deployed, the first coil and the second coil of the retention portion extend about an axis of the retention portion that is at least partially coextensive with the straight or curvilinear central axis of the portion of the drainage lumen.

Clause 8: The ureteral catheter of clause 7, wherein a gap between the sidewall of the drainage lumen of the first coil and an adjacent sidewall of the drainage lumen of the second coil is less than 3.0 mm, preferably between about 0.25 mm and 2.5 mm, and more preferably between about 0.5 mm and 2.0 mm.

Clause 9: The ureteral catheter of clause 7 or clause 8, wherein the first coil is a half coil extending from 0 degrees to 180 degrees and is free from openings, wherein the second coil is a full coil extending from 180 degrees to 540 degrees, and wherein the first section of the plurality of sections extends between 180 and 360 degrees of the second coil and the second section extends between 360 degrees and 540 degrees of the second coil.

Clause 10: The ureteral catheter of any of clauses 7 to 9, wherein, along the plurality of sections, the sidewall of the drainage lumen comprises a radially inwardly facing side and a radially outwardly facing side, and wherein a total area of the openings on the radially inwardly facing side is greater than a total area of the openings on the radially outwardly facing side.

Clause 11: The ureteral catheter of any of clauses 7 to 10, wherein the retention portion of the drainage lumen comprises a sidewall comprising a radially inwardly facing side and a radially outwardly facing side, and wherein one or more perforations are disposed on the radially inwardly facing side, and wherein the radially outwardly facing side is essentially free of perforations.

Clause 12: The ureteral catheter of any of clauses 7 to 11, wherein a distal-most portion of the retention portion is bent inwardly relative to a curvature of a distal-most coil, such that a central axis of the distal-most portion extends from the distal end of the drainage lumen toward the axis of the retention portion.

Clause 13: The ureteral catheter of any of clauses 7 to 12, wherein the first diameter of the first coil is about 8 mm to 10 mm and the second diameter of the second coil is about 16 mm to 20 mm.

Clause 14: The ureteral catheter of any of clauses 7 to 13, wherein the retention portion further comprises a third coil extending about the axis of the retention portion, the third coil having a diameter greater than or equal to either the first diameter or the second diameter, the third coil being closer to an end of the distal portion of the drainage lumen than the second coil.

Clause 15: The ureteral catheter of any of clauses 7 to 14, wherein the drainage lumen is transitionable between an uncoiled configuration for insertion from the patient's bladder into the patient's ureter and the coiled configuration for deployment within the patient's kidney, renal pelvis, and/or in the ureter adjacent to the renal pelvis.

Clause 16: The ureteral catheter of clause 15, wherein the drainage lumen is naturally biased to the coiled configuration.

Clause 17: The ureteral catheter of any of clauses 1 to 16, wherein the sections are of equal length.

Clause 18: The ureteral catheter of any of clauses 1 to 17, wherein a volumetric flow rate for fluid which flows into a second section is at least 30% of a volumetric flow rate of fluid which flows into the openings of the first section, as calculated based on a mass transfer shell balance evaluation for calculating volumetric flow rates through openings of the sections when a negative pressure of −45 mmHg is applied to a proximal end of the drainage lumen.

Clause 19: The ureteral catheter of any of clauses 1 to 18, wherein a volumetric flow rate for fluid flowing into a proximal-most section of the plurality of sections is less than 60% of a volumetric flow rate for fluid flowing through the proximal portion of the drainage lumen, as calculated based on a mass transfer shell balance evaluation for calculating volumetric flow rates through openings of the sections when a negative pressure of −45 mmHg is applied to a proximal end of the drainage lumen.

Clause 20: The ureteral catheter of any of clauses 1 to 19, wherein a volumetric flow rate for fluid flowing into two proximal-most sections of the plurality of sections is less than 90% of a volumetric flow rate of fluid flowing through the proximal portion of the draining lumen, as calculated based on a mass transfer shell balance evaluation for calculating volumetric flow rates through openings of the sections when a negative pressure of −45 mmHg measured at an outflow port of a vacuum pump is applied to a proximal end of the drainage lumen.

Clause 21: The ureteral catheter of any of clauses 1 to 20, wherein openings of a third section of the plurality of sections have a total area that is greater than the total area of the openings of the first section or the second section, and wherein the third section is closer to the distal end of the drainage lumen than the first section or the second section.

Clause 22: The ureteral catheter of any of clauses 1 to 21, wherein a total area of the one or more openings of a section increases for sections closer to a distal end of the retention portion.

Clause 23: The ureteral catheter of any of clauses 1 to 22, wherein the drainage lumen has an inner diameter of between about 0.5 mm and 1.5 mm, and wherein a total area of openings of the first section and/or a total area of openings of the second section is between about 0.002 mm$^2$ and about 2.5 mm$^2$.

Clause 24: The ureteral catheter of any of clauses 1 to 23, wherein the drainage lumen has an inner diameter of between about 0.5 mm and 1.5 mm, and wherein a total area of openings of the first section is between about 0.002 mm$^2$ and about 1.0 mm$^2$ and a total area of openings of the second section is greater than about 0.5 mm$^2$.

Clause 25: The ureteral catheter of clause 24, wherein each of the sections of the plurality of sections is an equal length of between about 5 mm and about 35 mm, and preferably between about 5 mm and 15 mm.

Clause 26: The ureteral catheter of any of clauses 1 to 25, wherein the drainage lumen has an uncoiled longitudinal length of between about 30 cm and about 120 cm.

Clause 27: The ureteral catheter of any of clauses 1 to 26, wherein one or more of the openings have a cross-sectional area of between about 0.002 mm$^2$ and about 0.25 mm$^2$, and wherein the second section comprises more openings than the first section.

Clause 28: The ureteral catheter of any of clauses 1 to 27, wherein the drainage lumen comprises an open distal end having an inner diameter of between about 0.5 mm and about 1.5 mm.

Clause 29: The ureteral catheter of any of clauses 1 to 28, wherein the openings are circles with a diameter of between about 0.5 mm and about 1.5 mm, and wherein a diameter of an opening of one of the sections is at least 0.05 mm greater than a diameter of an opening of a proximally adjacent section.

Clause 30: The ureteral catheter of any of clauses 1 to 29, wherein a distance between a center of an opening of one of the sections and a center of an opening of an adjacent section is between about 5.0 mm and about 15.0 mm.

Clause 31: The ureteral catheter of any of clauses 1 to 30, wherein the openings of the plurality of sections are circular and have a diameter of between about 0.05 mm and about 1.0 mm.

Clause 32: The ureteral catheter of any of clauses 1 to 31, wherein each section comprises a single opening.

Clause 33: The ureteral catheter of clause 32, wherein an area of a single opening of a section closer to the proximal portion of the drainage lumen is less than an area of a single opening of a section closer to the distal end of the drainage lumen.

Clause 34: The ureteral catheter of clause 32 or clause 33, wherein an area of each of the single openings is less than an area of a distally adjacent single opening.

Clause 35: The ureteral catheter of any of clauses 32 to 34, wherein the distal end of the drainage lumen has an opening having an area greater than an area of the single opening of an adjacent section of the plurality of sections.

Clause 36: The ureteral catheter of any of clauses 1 to 35, wherein each of the openings of the plurality of sections has the same area, and wherein the second section comprises more openings than the first section.

Clause 37: The ureteral catheter of any of clauses 1 to 36, wherein at least two openings of a section of the plurality of sections are arranged such that a virtual line extending around a circumference of the sidewall of the drainage lumen contacts at least a portion of each of the at least two openings.

Clause 38: The ureteral catheter of any of clauses 1 to 37, wherein the openings of at least one of the sections are arranged such that a virtual line extending along the sidewall of the drainage lumen in a curvilinear direction contacts at least a portion of each of the openings of the respective section.

Clause 39: The ureteral catheter of any of clauses 1 to 38, wherein openings of the first section are arranged along a first virtual line extending in an curvilinear direction along the sidewall of the drainage lumen, wherein at least one of the openings of the second section is arranged along a second virtual line extending in a curvilinear direction along the sidewall of the drainage lumen, and wherein at least one of the openings of the second section is arranged along a third virtual line extending in a curvilinear direction along the sidewall of the drainage lumen.

Clause 40: The ureteral catheter of clause 39, wherein the first virtual line is not coextensive with the second virtual line and/or with the third virtual line.

Clause 41: The ureteral catheter of clause 39 or clause 40, wherein the second virtual line is not coextensive with the third virtual line.

Clause 42: The ureteral catheter of any of clauses 39 to 41, wherein the first, second, and third virtual lines are parallel.

Clause 43: The ureteral catheter of any of clauses 1 to 42, wherein each opening of a plurality of openings is independently selected from one or more of circles, triangles, rectangles, ellipses, ovals, and squares.

Clause 44: A ureteral catheter, comprising: a drainage lumen comprising a proximal portion configured to be positioned in at least a portion of a patient's urethra and a distal portion configured to be positioned in a patient's kidney, renal pelvis, and/or in the ureter adjacent to the renal pelvis, the distal portion comprising a retention portion for maintaining positioning of the distal portion of the drainage lumen, the retention portion comprising a plurality of equal length sections of the drainage lumen, each of which comprises one or more openings on a sidewall of the drainage lumen for permitting fluid flow into the drainage lumen, wherein a volumetric flow rate for fluid flowing into a proximal-most section of the plurality of sections is between about 1% and 60%, preferably between about 10% and 60%, and more preferably between about 30% and 60%, of a volumetric flow rate of fluid flowing through the proximal portion of the drainage lumen, as calculated based on a mass transfer shell balance evaluation for calculating volumetric flow rates through openings of the sections when a negative pressure of −45 mmHg is applied to a proximal end of the drainage lumens.

Clause 45: The ureteral catheter of clause 44, wherein a volumetric flow rate of fluid flowing into two proximal-most sections of the plurality of sections is between about 1% and 90%, preferably between about 30% and 90%, and more preferably between about 60% and 90% of the volumetric flow rate of fluid flowing through the proximal portion of the drainage lumen, as calculated based on a mass transfer shell balance evaluation for calculating volumetric flow rates through openings of the sections when a negative pressure of −45 mmHg is applied to a proximal end of the drainage lumen.

Clause 46: The ureteral catheter of clause 44 or clause 45, wherein each section comprises a single opening, and wherein a single opening of a section closer to the proximal end of the drainage lumen is less than an area of a single opening in a section closer to a distal end of the drainage lumen.

Clause 47: The ureteral catheter of any of clauses 44 to 46, wherein a distal end of the drainage lumen has an opening having an area greater than an area of a single opening of an adjacent section of the plurality of sections.

Clause 48: The ureteral catheter of any of clauses 44 to 47, wherein each of the openings of the plurality of sections has the same area, and wherein a second section of the plurality of sections comprises more openings than the proximal-most section.

Clause 49: The ureteral catheter of any of clauses 44 to 48, wherein a shape of the openings of the plurality of sections are one or more of circles, triangles, rectangles, squares, ellipses, hourglass shapes, and random perimeter openings.

Clause 50: A ureteral catheter, comprising: a drainage lumen comprising a proximal portion configured to be positioned in at least a portion of a patient's urethra and/or bladder and a distal portion configured to be positioned in a patient's kidney, renal pelvis, and/or in the ureter adjacent to the renal pelvis, the distal portion comprising a coiled retention portion for maintaining positioning of the distal portion of the drainage lumen, the coiled retention portion comprising: at least a first coil having a first diameter extending about an axis of the retention portion that is at least partially coextensive with a straight or curvilinear central axis of a portion of the drainage lumen proximal to the retention portion; and a plurality of sections, each of which comprises one or more openings on a sidewall of the retention portion for permitting fluid flow into the drainage lumen, wherein, along the plurality of sections, the sidewall of the retention portion comprises a radially inwardly facing side and a radially outwardly facing side, and wherein a total area of the openings on the radially inwardly facing side is greater than a total area of the openings on the radially outwardly facing side, and wherein a total area of openings of a first section of the plurality of sections is less than a total area of openings of an adjacent second section of the plurality of sections, the second section being closer to a distal end of the drainage lumen than the first section.

Clause 51: The ureteral catheter of clause 50, wherein the retention portion further comprises a second coil having a second diameter, the first diameter being less than the second diameter, the second coil being closer to the distal end of the drainage lumen than the first coil.

Clause 52: The ureteral catheter of clause 51, wherein the first coil is a half coil extending from 0 degrees to 180 degrees and is free from openings, wherein the second coil is a full coil extending from 180 degrees to 540 degrees, and wherein the first section of the plurality of sections extends between 180 and 360 degrees of the second coil and the second section extends between 360 degrees and 540 degrees of the second coil.

Clause 53: The ureteral catheter of clauses 51 or clause 52, wherein the retention portion further comprises a third coil extending about the axis of the retention portion, the third coil having a diameter greater than or equal to either the first diameter or the second diameter, the third coil being closer to an end of the distal portion of the drainage lumen than the second coil.

Clause 54: A ureteral catheter, comprising: a drainage lumen comprising a proximal portion configured to be positioned in at least a portion of a patient's urethra and/or bladder and a distal portion configured to be positioned in a patient's kidney, renal pelvis, and/or in the ureter adjacent to the renal pelvis, the distal portion comprising a retention portion for maintaining positioning of the distal portion of the drainage lumen, the retention portion comprising a plurality of openings on a sidewall of the retention portion for permitting fluid flow into the drainage lumen, wherein an area of an opening of the plurality of openings which is closer to a proximal end of the retention portion is less than an area of an opening of the plurality of openings which is closer to the distal end of the drainage lumen.

Clause 55: The ureteral catheter of clause 54, wherein an area of each opening of the plurality of openings is greater than an area of a proximally adjacent opening of the plurality of openings.

Clause 56: The ureteral catheter of clause 54 or clause 55, wherein a shape of each opening is independently selected from one or more of circles, triangles, rectangles, and squares.

Clause 57: A system for inducing negative pressure in a portion of a urinary tract of a patient, the system comprising: at least one ureteral catheter comprising a drainage lumen comprising a proximal portion configured to be positioned in at least a portion of a patient's urethra and/or bladder and a distal portion configured to be positioned in a patient's kidney, renal pelvis, and/or in the ureter adjacent to the renal pelvis, the distal portion comprising a retention portion for maintaining positioning of the distal portion of the drainage lumen, the retention portion comprising a plurality of equal length sections of the drainage lumen, each of which comprises one or more openings on a sidewall of the drainage lumen for permitting fluid flow into the drainage lumen; and a pump in fluid communication with the drainage lumen of the at least one ureteral catheter, the pump being configured for inducing a positive and/or a negative pressure in a portion of the urinary tract of the patient to draw fluid into the drainage lumen through the openings of the sections of the retention portion, wherein a total area of openings of a first section of the plurality of sections is less than a total area of openings of an adjacent second section of the plurality of sections, the second section being closer to a distal end of the drainage lumen than the first section.

Clause 58: The system of clause 57, wherein the pump is configured to generate the position and/or negative pressure in a proximal end of the drainage lumen.

Clause 59: The system of clause 57 or clause 58, wherein the pump applies a negative pressure of 100 mmHg or less to a proximal end of the drainage lumen.

Clause 60: The system of clause 59, wherein the pump is configured to operate at one of three pressure levels selected by a user, the pressure levels generating a negative pressure of 15 mmHg, 30 mmHg, and 45 mmHg.

Clause 61: The system of any of clauses 57 to 60, wherein the pump is configured to alternate between generating negative pressure and generating positive pressure.

Clause 62: The system of any of clauses 57 to 61, wherein the pump is configured to alternate between providing negative pressure and equalizing pressure to atmosphere.

Clause 63: The system of any of clauses 57 to 62, further comprising: one or more sensors in fluid communication with the drainage lumen, the one or more sensors being configured to determine information comprising at least one of capacitance, analyte concentration, and temperature of urine within the drainage lumen; and a controller comprising computer readable memory including programming instructions that, when executed, cause the controller to: receive the information from the one or more sensors and adjust an operating parameter of the pump based, at least in part, on the information received from the one or more sensors to increase or decrease vacuum pressure in the drainage lumen of the at least one ureteral catheter to adjust flow of urine through the drainage lumen.

Clause 64: The system of any of clauses 57 to 63, comprising a first ureteral catheter configured to be placed in a first kidney, renal pelvis, and/or in the ureter adjacent to the renal pelvis of the patient and a second ureteral catheter configured to be placed in a second kidney, renal pelvis, and/or in the ureter adjacent to the renal pelvis of the patient, wherein the pump is configured to apply negative pressure independently to the first ureteral catheter and the second ureteral catheter such that the pressure in each catheter can be the same or different from the other catheter.

Clause 65: The system of any of clauses 57 to 64, wherein the pump has a sensitivity of 10 mmHg or less.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which.

DETAILED DESCRIPTION

Figure 1:
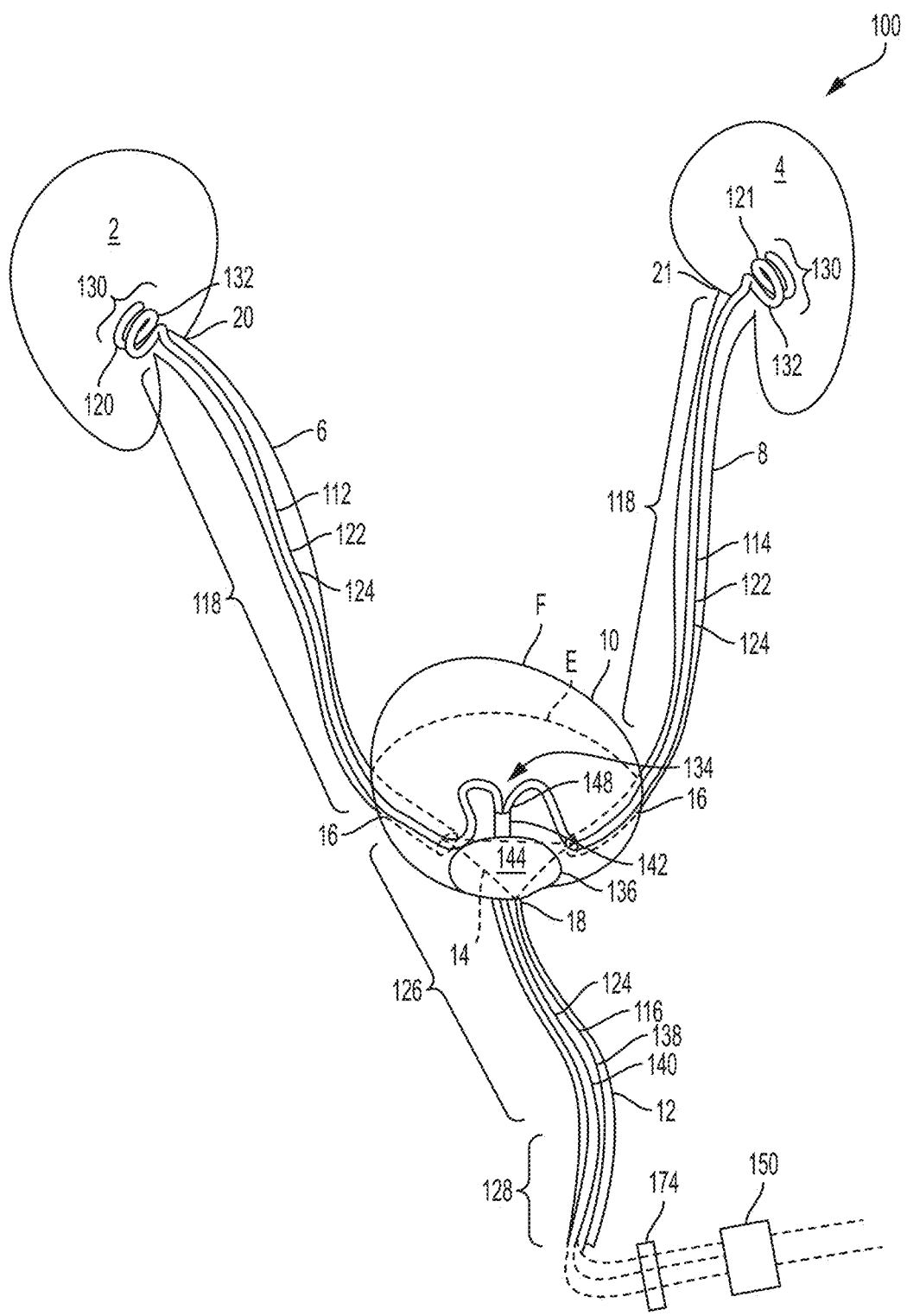
FIG. 1 is a schematic drawing of an indwelling portion of a urine collection assembly deployed in a urinary tract of a patient, according to an example of the present invention.

As used herein, the singular form of "a", "an", and "the" include plural referents unless the context clearly states otherwise.

As used herein, the terms "right", "left", "top", and derivatives thereof shall relate to the invention as it is oriented in the drawing figures. The term "proximal" refers to the portion of the catheter device that is manipulated or contacted by a user and/or to a portion of an indwelling catheter nearest to the urinary tract access site. The term "distal" refers to the opposite end of the catheter device that is configured to be inserted into a patient and/or to the portion of the device that is inserted farthest into the patient's urinary tract. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

For the purposes of this specification, unless otherwise indicated, all numbers expressing quantities of ingredients, reaction conditions, dimensions, physical characteristics, and so forth used in the specification and claims are to be understood as being modified in all instances by the term "about." Unless indicated to the contrary, the numerical parameters set forth in the following specification and attached claims are approximations that can vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

Fluid retention and venous congestion are central problems in the progression to advanced renal disease. Excess sodium ingestion coupled with relative decreases in excretion leads to isotonic volume expansion and secondary compartment involvement. In some examples, the present invention is generally directed to devices and methods for facilitating drainage of urine or waste from the bladder, ureter, and/or kidney(s) of a patient. In some examples, the present invention is generally directed to devices and methods for inducing a negative pressure in the bladder, ureter, and/or kidney(s) of a patient. While not intending to be bound by any theory, it is believed that applying a negative pressure to the bladder, ureter, and/or kidney(s) can offset the medullary nephron tubule re-absorption of sodium and water in some situations. Offsetting re-absorption of sodium and water can increase urine production, decrease total body sodium, and improve erythrocyte production. Since the intra-medullary pressures are driven by sodium and, therefore, volume overload, the targeted removal of excess sodium enables maintenance of volume loss. Removal of volume restores medullary hemostasis. Normal urine production is 1.48-1.96 L/day (or 1-1.4 ml/min).

Fluid retention and venous congestion are also central problems in the progression of prerenal Acute Kidney Injury (AKI). Specifically, AKI can be related to loss of perfusion or blood flow through the kidney(s). Accordingly, in some examples, the present invention facilitates improved renal hemodynamics and increases urine output for the purpose of relieving or reducing venous congestion. Further, it is anticipated that treatment and/or inhibition of AKI positively impacts and/or reduces the occurrence of other conditions, for example, reduction or inhibition of worsening renal function in patients with NYHA Class III and/or Class IV heart failure. Classification of different levels of heart failure are described in *The Criteria Committee of the New York Heart Association*, (1994), *Nomenclature and Criteria for Diagnosis of Diseases of the Heart and Great Vessels*, (9th ed.), Boston: Little, Brown & Co. pp. 253-256, the disclosure of which is incorporated by reference herein in its entirety. Reduction or inhibition of episodes of AKI and/or chronically decreased perfusion may also be a treatment for Stage 4 and/or Stage 5 chronic kidney disease. Chronic kidney disease progression is described in National Kidney Foundation, K/DOQI *Clinical Practice Guidelines for Chronic Kidney Disease: Evaluation, Classification and Stratification*. Am. J. Kidney Dis. 39:S1-S266, 2002 (Suppl. 1), the disclosure of which is incorporated by reference herein in its entirety.

Systems for Inducing Negative Pressure

Figure 27:
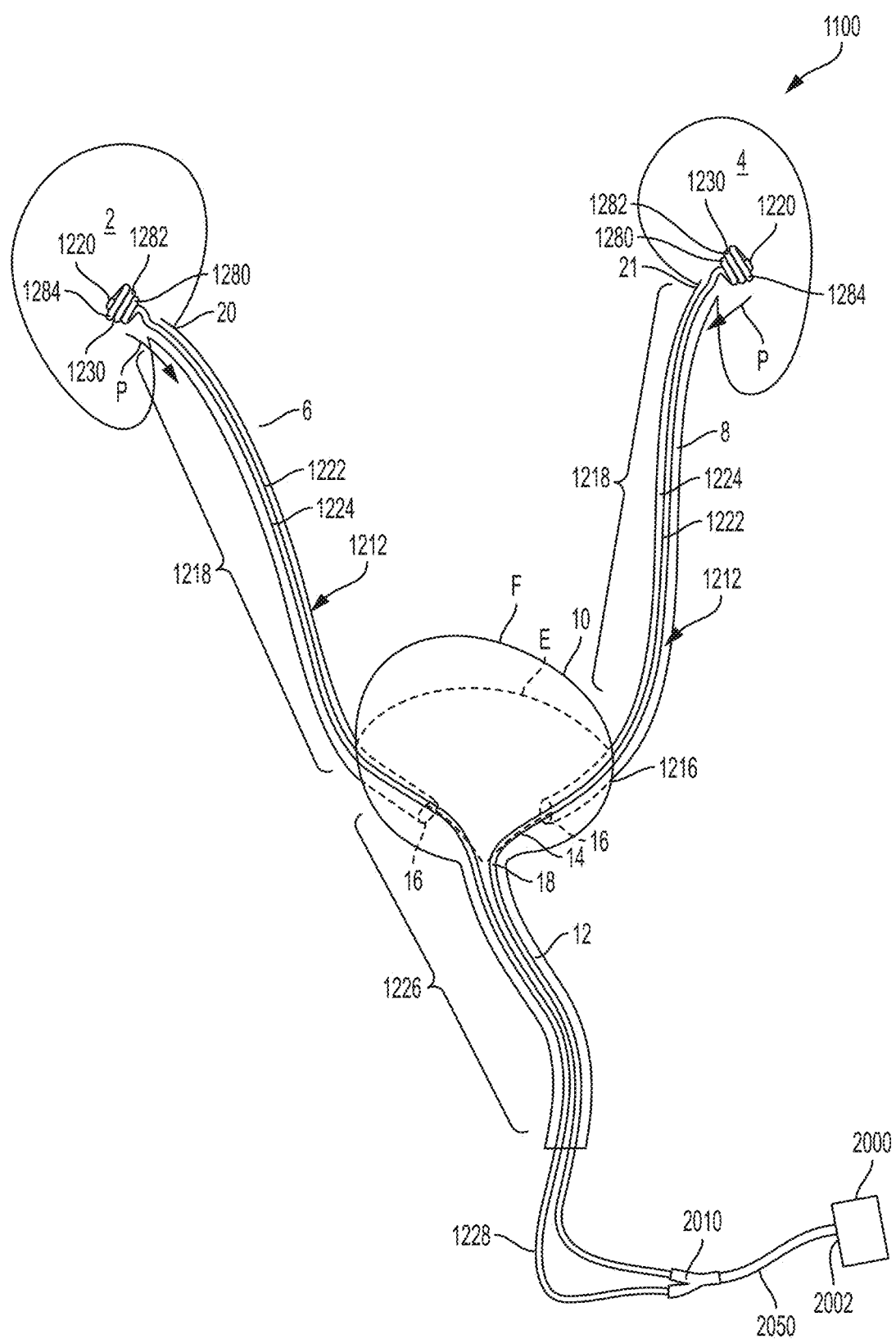
FIG. 27 is a schematic drawing of another example of an indwelling portion of a urine collection assembly deployed in a urinary tract of a patient, according to an example of the present invention.

With reference to FIG. 27, an exemplary system 1100 for inducing negative pressure in a urinary tract of a patient for increasing renal perfusion is illustrated. The system 1100 comprises one or two ureteral catheters 1212 connected to a fluid pump 2000 for generating the negative pressure. In some examples, the pump 2000 may also generate a positive pressure and, for example, may be configured to alternate between providing negative pressure, positive pressure, and equalizing pressure to atmosphere based on a selection from a user or automatically according to a predetermined schedule. The pump 2000 can be configured to provide a low level negative pressure of 100 mmHg or less to a proximal end of the catheter 1212. In some examples, the pump 2000 can be configured to operate at a number of discrete pressure levels. For example, the pump 2000 may be configured to operate at pressure levels of 15 mmHg, 30 mmHg, and 45 mmHg. A user can select one of the pressure levels using a switch, dial, or controller as are known in the art.

A commercially available pump which can be adapted for use with the system 1100 is the Air Cadet Vacuum Pump from Cole-Partner Instrument Company (Model No. EW-07530-85). The pump 2000 can be connected in series to the regulator, such as the V-800 Series Miniature Precision Vacuum Regulator—⅛ NPT Ports (Model No. V-800-10-W/K), manufactured by Airtrol Components Inc. Pumps which can be adapted for use with the system 2000 are also available from Ding Hwa Co., Ltd (DHCL Group) of Dacun, Changhua, China.

In some examples, at least a portion of the pump 2000 can be positioned within the patient's urinary tract, for example within the bladder. For example, the pump 2000 can comprise a pump module and a control module coupled to the pump module, the control module being configured to direct motion of the pump module. At least one (one or more) of the pump module, the control module, or the power supply may be positioned within the patient's urinary tract. The pump module can comprise at least one pump element positioned within the fluid flow channel to draw fluid through the channel. Some examples of suitable pump assemblies, systems and methods of use are disclosed in U.S. Patent Application No. 62/550,259, entitled "Indwelling Pump for Facilitating Removal of Urine from the Urinary Tract", filed concurrently herewith, which is incorporated by reference herein in its entirety.

The patient's urinary tract comprises the patient's right kidney 2 and left kidney 4. The kidneys 2, 4 are responsible for blood filtration and clearance of waste compounds from the body through urine. Urine produced by the right kidney 2 and the left kidney 4 is drained into a patient's bladder 10 through tubules, namely a right ureter 6 and a left ureter 8, which are connected to the kidneys at the renal pelvis 20, 21. Urine may be conducted through the ureters 6, 8 by peristalsis of the ureter walls, as well as by gravity. The ureters 6, 8 enter the bladder 10 through a ureter orifice or opening 16. The bladder 10 is a flexible and substantially hollow structure adapted to collect urine until the urine is excreted from the body. The bladder 10 is transitionable from an empty position (signified by reference line E) to a full position (signified by reference line F). Normally, when the bladder 10 reaches a substantially full state, urine is permitted to drain from the bladder 10 to a urethra 12 through a urethral sphincter or opening 18 located at a lower portion of the bladder 10. Contraction of the bladder 10 can be responsive to stresses and pressure exerted on a trigone region 14 of the bladder 10, which is the triangular region extending between the ureteral openings 16 and the urethral opening 18. The trigone region 14 is sensitive to stress and pressure, such that as the bladder 10 begins to fill, pressure on the trigone region 14 increases. When a threshold pressure on the trigone region 14 is exceeded, the bladder 10 begins to contract to expel collected urine through the urethra 12.

Figure 28:
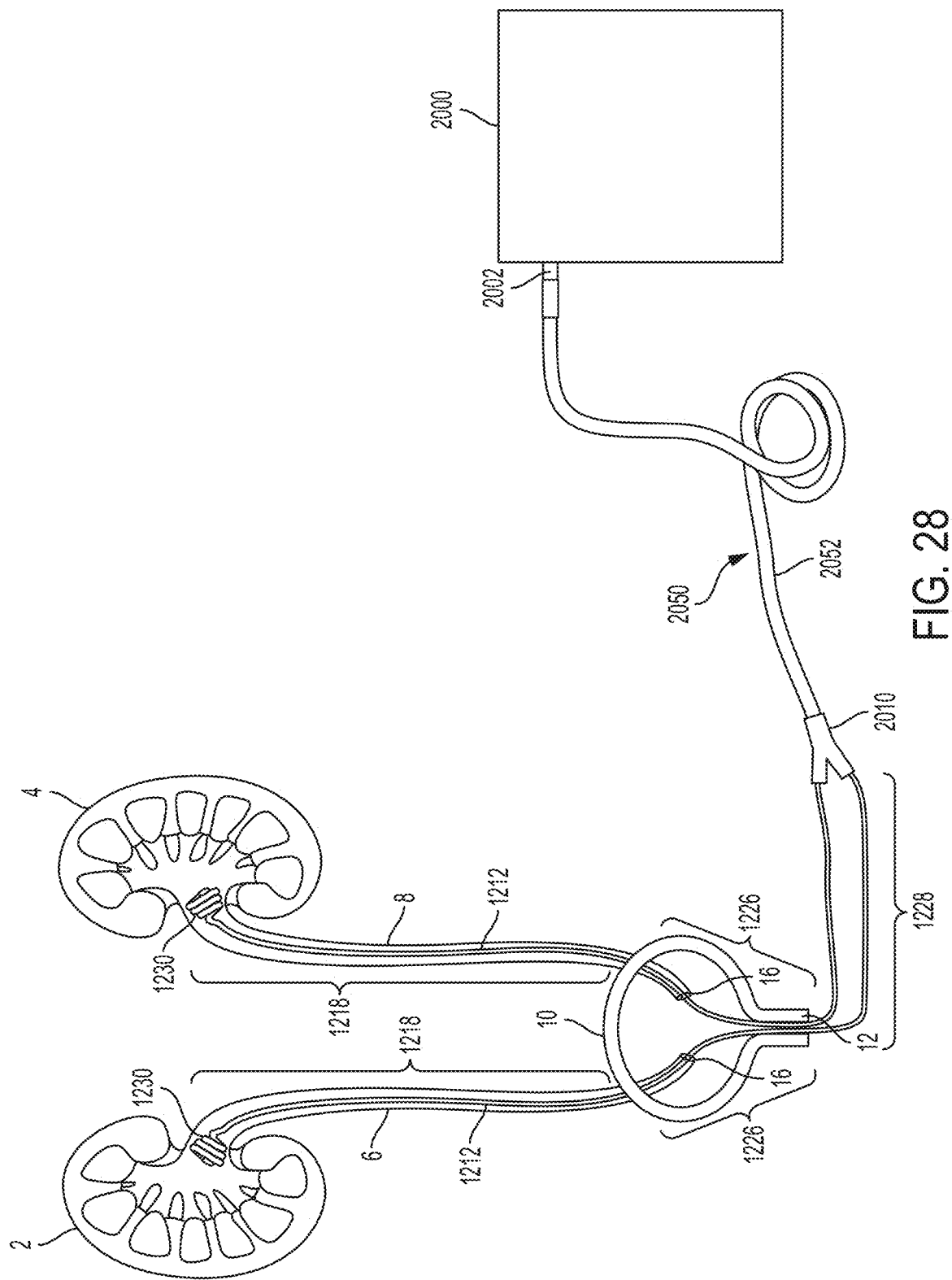
FIG. 28 is another schematic drawing of the urine collection assembly of FIG. 27.
Figure 29:
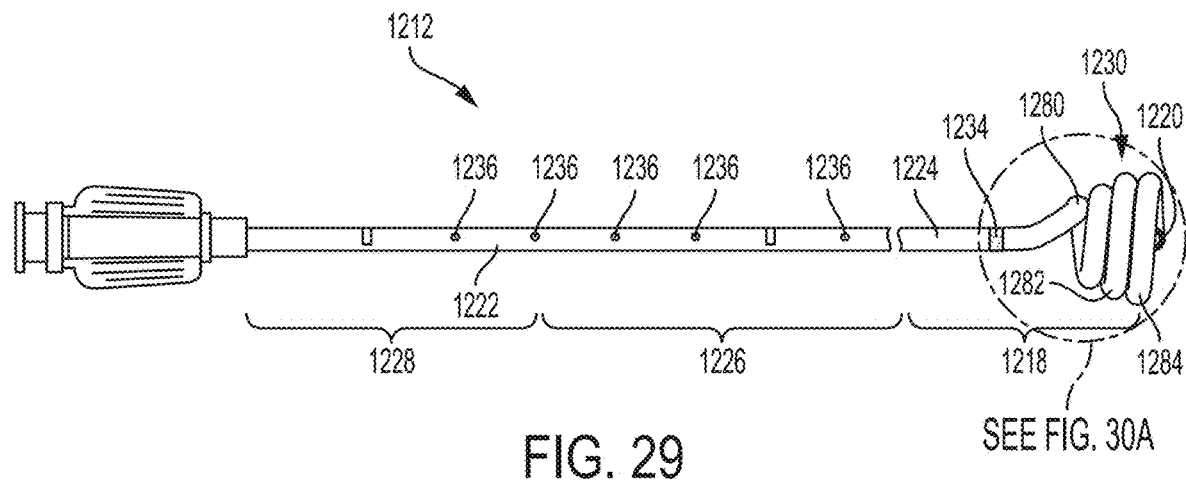
FIG. 29 is a front view of another example of a ureteral catheter according to an example of the disclosure.
Figure 30A:
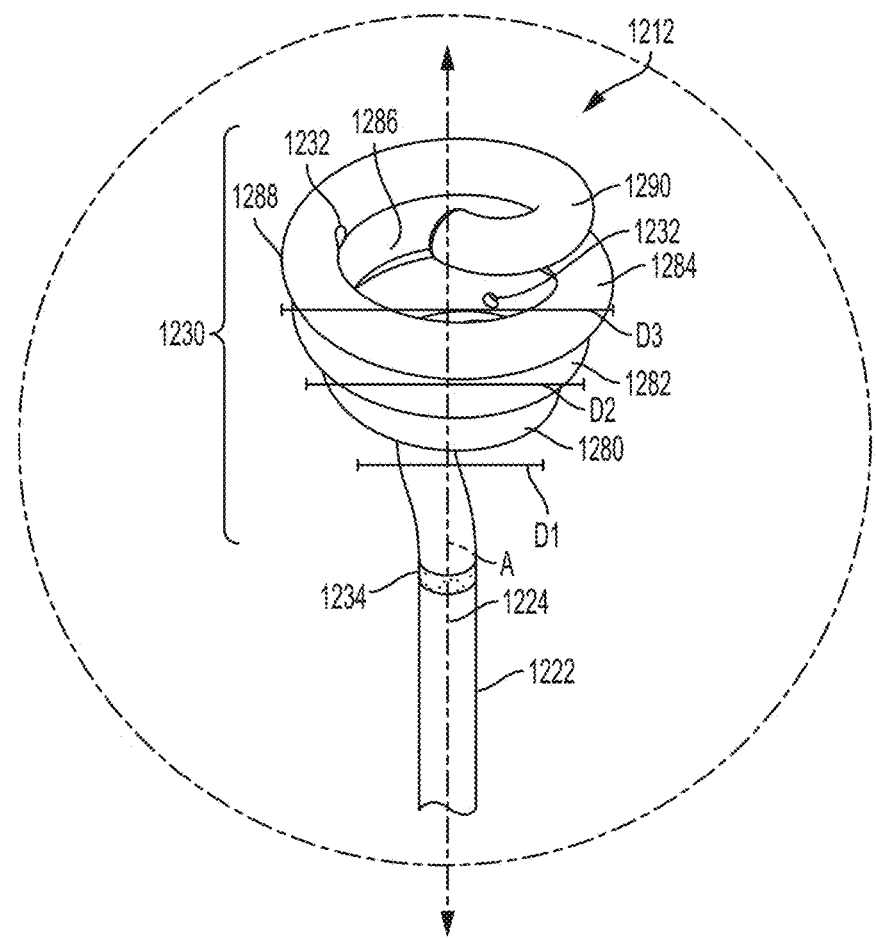
FIG. 30A is a perspective view of the retention portion of the ureteral catheter of FIG. 29 enclosed by circle 30A according to an example of the disclosure.
Figure 30B:
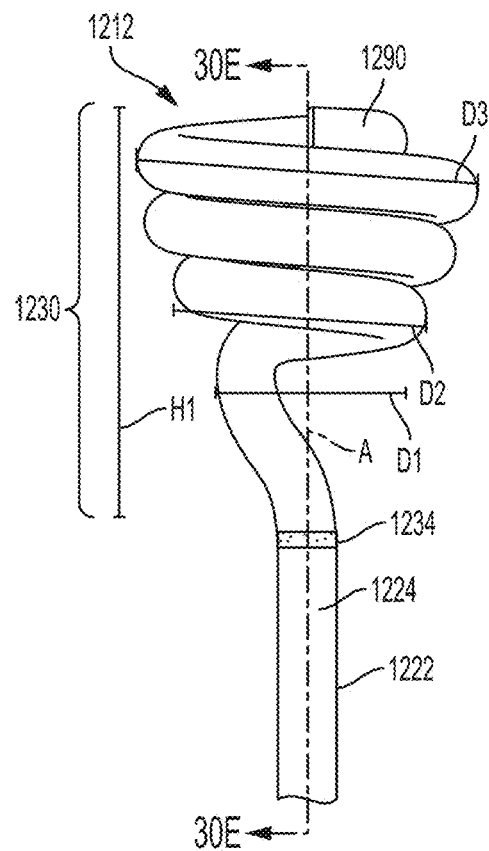
FIG. 30B is a front view of the retention portion of FIG. 30A according to an example of the disclosure.
Figure 30C:
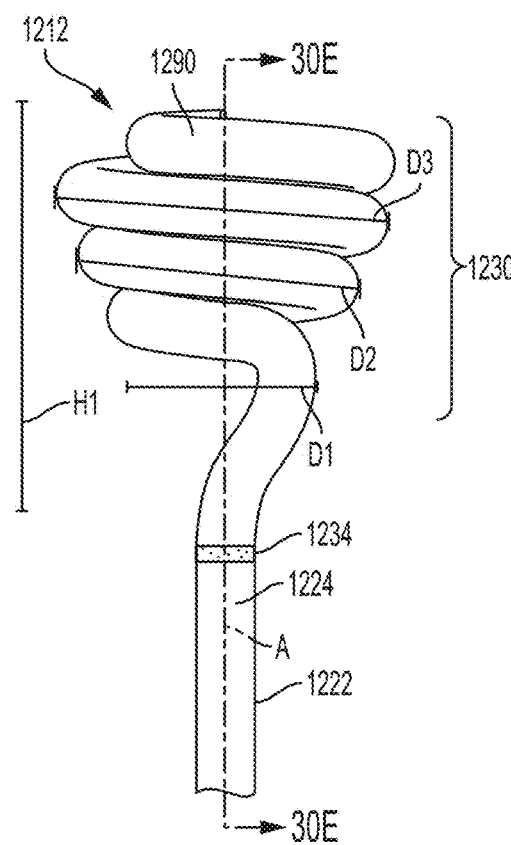
FIG. 30C is a rear view of the retention portion of FIG. 30A according to an example of the disclosure.
Figure 30D:
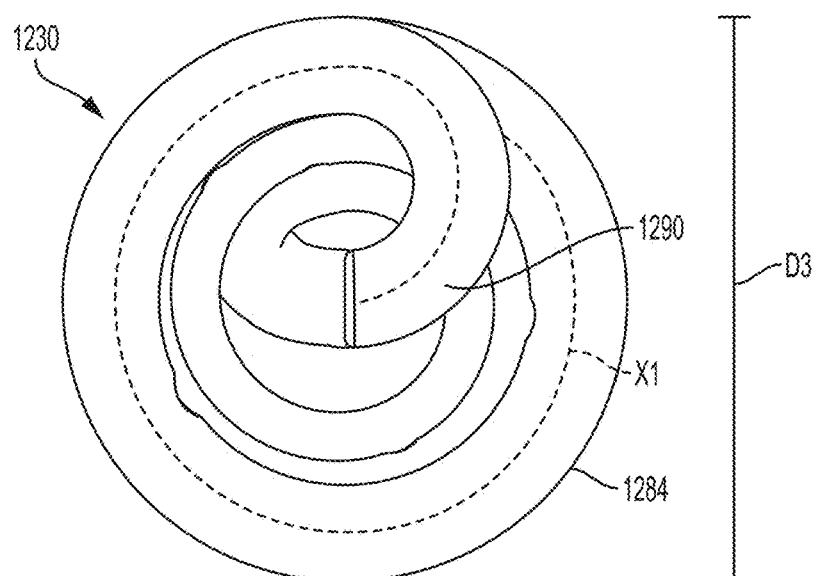
FIG. 30D is a top view of the retention portion of FIG. 30A according to an example of the disclosure.
Figure 30E:
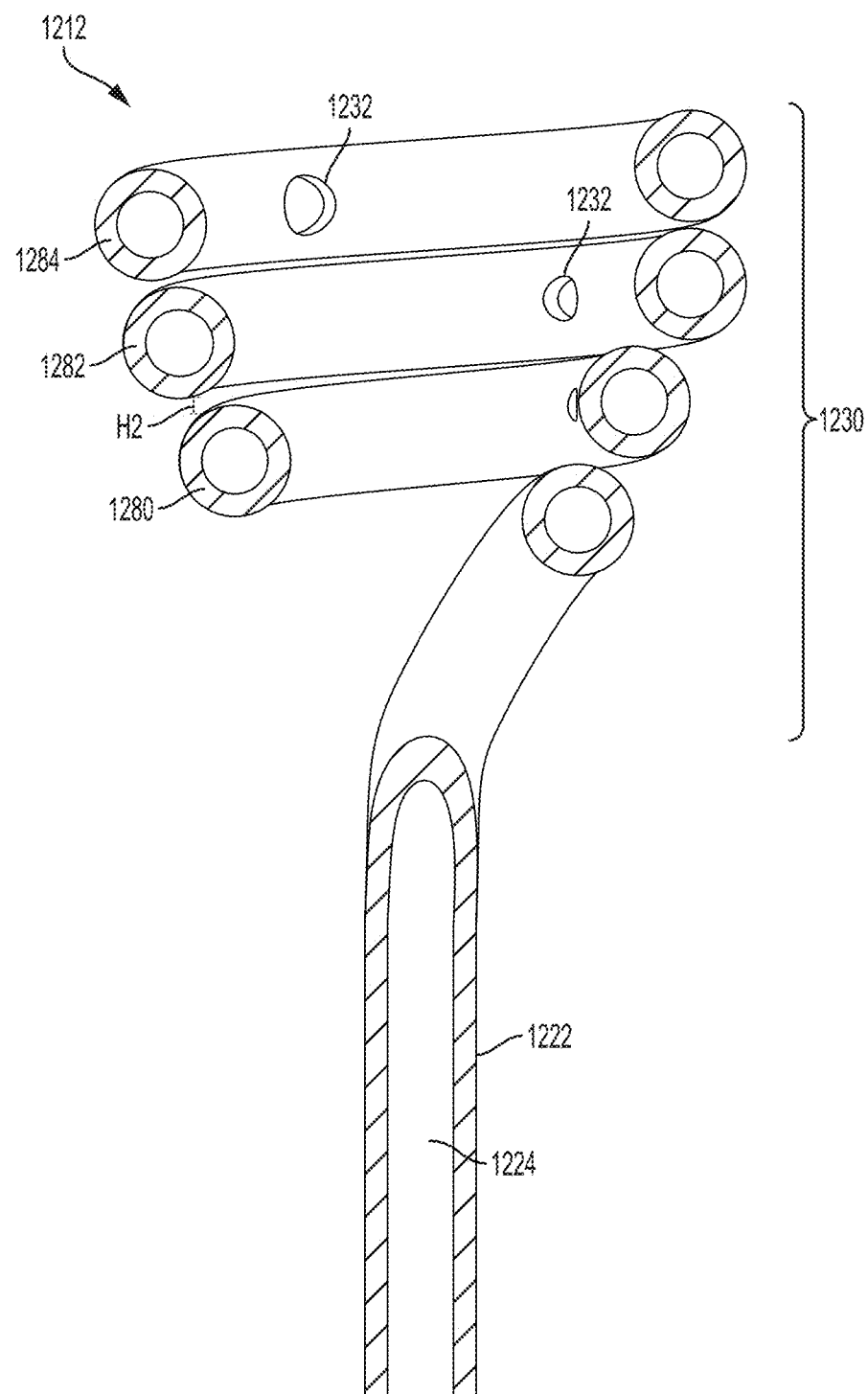
FIG. 30E is a cross sectional view of the retention portion of FIG. 30A taken along line 30E-30E according to an example of the disclosure.
Figure 36:
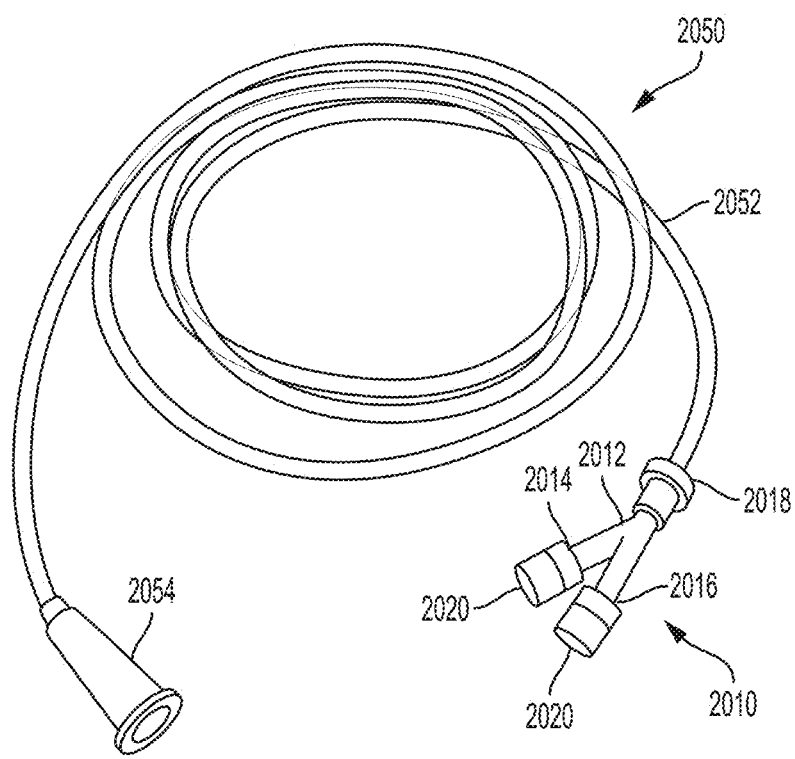
FIG. 36 is a perspective view of a tubing assembly and y-connector for connecting a ureteral catheter to a fluid pump according to an example of the disclosure.
Figure 37:
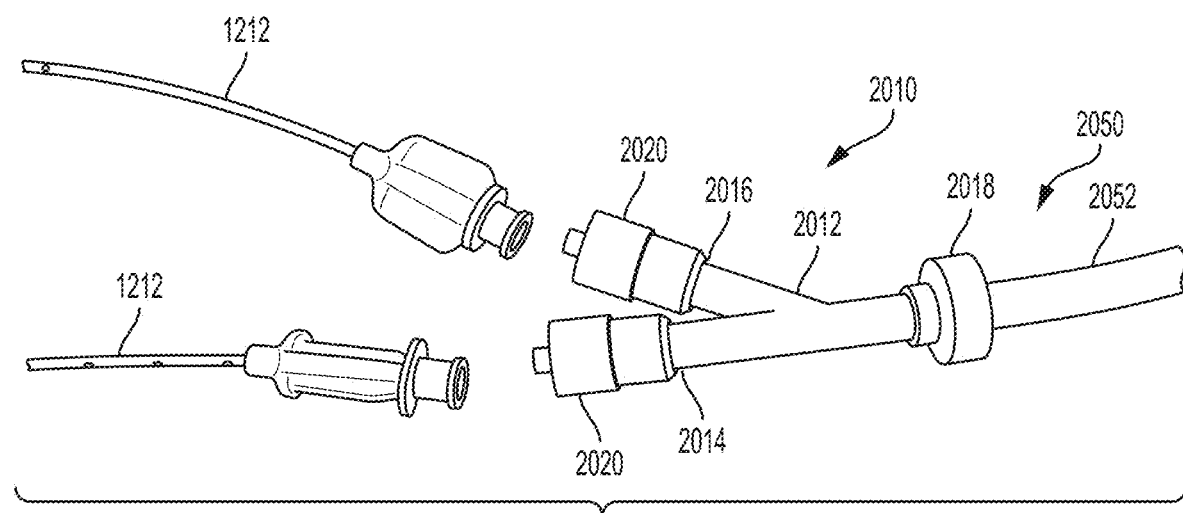
FIG. 37 is a perspective view of ureteral catheters being connected to the y-connector of FIG. 36 according to an example of the present disclosure.

As shown in FIGS. 27 and 28, distal portions of the ureteral catheter(s) are deployed in the renal pelvis 20, 21 near the kidneys 2, 4. Proximal portions of one or more of the catheter(s) 1212 are connected to a single outflow port 2002 of a fluid pump 2000 through a Y-connector 2010 and tubing set 2050. An exemplary Y-connector 2010 and tubing set 2020 connected thereto are shown in FIGS. 36 and 37. The Y-connector 2010 comprises a tubular body 2012 formed from a rigid plastic material, the body 2012 comprising two inflow ports 2014, 2016 and a single outflow port comprising a one-way check valve 2018 to prevent backflow. The inflow ports 2014, 2016 can comprise a connector portion 2020, such as a luer lock connector, screw connector, or similar mechanism as is known in the art for receiving the proximal end of the catheters 1212. As shown in FIG. 37, the proximal ends of catheters 1212 have a corresponding structure for mounting to the Y-connector 2010. The tubing set 2050 comprises a length of flexible medical tubing 2052 extending between the one-way check valve 2018 of the Y-connector 2010 and a funnel-shaped connector 2054 configured to engage the outflow port 2002 of a fluid pump 2000. The shape and size of the funnel-shaped connector 2054 can be selected based on the type of pump 2000 being used. In some examples, the funnel-shaped connector 2054 can be manufactured with a distinctive configuration so that it can only be connected to a particular pump type, which is deemed to be safe for inducing negative pressure in a patient's bladder, ureter, or kidneys. In other examples, as described herein, the connector 2054 can be a more generic configuration adapted for attachment to a variety of different types of fluid pumps.

System 1100 is but one example of a negative pressure system for inducing negative pressure that can be used with the ureteral catheters 1212 disclosed herein. Other systems and urine collection assemblies which can be used with catheters 1212 are shown, for example, in FIGS. 1, 9A, 10A, 11A, and 19. In addition, catheter(s) 1212 can be connected to separate sources of negative pressure. In other examples, one or more catheter(s) 1212 can be connected to a negative pressure source, while other caterer(s) 1212 can be connected to an unpressurized fluid collection container.

Exemplary Ureteral Catheters:

Specific characteristics of exemplary ureteral catheters will now be described in detail. As shown in FIGS. 27-39D, an exemplary ureteral catheter 1212 comprises at least one elongated body or tube 1222, the interior of which defines or comprises one or more drainage channel(s) or lumen(s), such as drainage lumen 1224. The tube 1222 size can range from about 1 Fr to about 9 Fr (French catheter scale). In some examples, the tube 1222 can have an external diameter ranging from about 0.33 to about 3.0 mm and an internal diameter ranging from about 0.165 to about 2.39 mm. In one example, the tube 1222 is 6 Fr and has an outer diameter of 2.0±0.1 mm. The length of the tube 1222 can range from about 30 cm to about 120 cm depending on the age (e.g., pediatric or adult) and gender of the patient.

The tube 1222 can be formed from a flexible and/or deformable material to facilitate advancing and/or positioning the tube 1222 in the bladder 10 and ureters 6, 8 (shown in FIGS. 27 and 28). For example, the tube 1222 can be formed from materials including biocompatible polymers, polyvinyl chloride, polytetrafluoroethylene (PTFE) such as Teflon®, silicone coated latex, or silicone. In one example, the tube 1222 is formed from a thermoplastic polyurethane. The tube 1222 can also include or be impregnated with one or more of copper, silver, gold, nickel-titanium alloy, stainless steel, and titanium. In some examples, the tube 1222 is impregnated with or formed from a material viewable by fluoroscopic imaging. In other examples, the biocompatible polymer which forms the tube 1222 can be impregnated with barium sulfate or a similar radiopaque material. As such, the structure and position of the tube 1222 is visible to fluoroscopy.

In some examples, the drainage lumen 1224 defined by tube 1222 comprises: a distal portion 1218 (e.g., a portion of the tube 1222 configured to be positioned in the ureter 6, 8 and renal pelvis 20, 21 (shown in FIGS. 27-29)); a middle portion 1226 (e.g., a portion of the tube 1222 configured to extend from the distal portion through ureteral openings 16 into the patient's bladder 10 and urethra 12 (shown in FIGS. 27-29)); and a proximal portion 1228 (e.g., a portion of the tube 1222 extending from the urethra 12 to an external fluid collection container and/or pump 2000). In one preferred example, the combined length of the proximal portion 1228 and the middle portion 1226 of the tube 1222 is about 54±2 cm. In some examples, the middle portion 1226 and proximal portion 1228 of the tube 1222 includes distance markings 1236 (shown in FIG. 29) on a sidewall of the tube 1222 which can be used, during deployment of the catheter 1212, to determine how far the tube 1222 is inserted into the urinary tract of the patient.

In some examples, the distal portion 1218 comprises an open distal end 1220 for drawing fluid into the drainage lumen 1224. The distal portion 1218 of the ureteral catheter 1212 further comprises a retention portion 1230 for maintaining the distal portion 1218 of the drainage lumen or tube 1222 in the ureter and/or kidney. In some examples, the retention portion comprises a plurality of radially extending coils 1280, 1282, 1284. The retention portion 1230 can be a flexible and bendable to permit positioning of the retention portion 1230 in the ureter, renal pelvis, and/or kidney. For example, the retention portion 1230 is desirably sufficiently bendable to absorb forces exerted on the catheter 1212 and to prevent such forces from being translated to the ureters. Further, if the retention portion 1230 is pulled in the proximal direction P (shown in FIGS. 27 and 28) toward the patient's bladder 10, the retention portion 1230 can be sufficiently flexible to begin to unwind or be straightened so that it can be drawn through the ureter 6, 8. In some examples, the retention portion 1230 is integral with the tube 1222. In other examples, the retention portion 1230 can comprise a separate tubular member connected to and extending from the tube or drainage lumen 1224. In some examples, the catheter 1212 comprises a radiopaque band 1234 (shown in FIG. 29) positioned on the tube 1222 at a proximal end of the retention portion 1230. The radiopaque band 1234 is visible by fluoroscopic imaging during deployment of the catheter 1212. In particular, a user can monitor advancement of the band 1234 through the urinary tract by fluoroscopy to determine when the retention portion 1230 is in the renal pelvis and ready for deployment.

In some examples, the retention portion 1230 comprises perforations, drainage ports, or openings 1232 (shown in FIG. 30A) in a sidewall of the tube 1222. As used herein, "opening" or "hole" means a continuous void space or channel through the sidewall from the outside to the inside of the sidewall, or vice versa. In some examples, each of the at least one opening(s) can have an area which can be the same or different and can range from about 0.002 mm$^2$ to about 100 mm$^2$, or about 0.002 mm$^2$ to about 10 mm$^2$. As used herein, the "area" or "surface area" or "cross-sectional area" of an opening means the smallest or minimum planar area defined by a perimeter of the opening. For example, if the opening is circular and has a diameter of about 0.36 mm (area of 0.1 mm$^2$) at the outside of the sidewall, but a diameter of only 0.05 mm (area of 0.002 mm$^2$) at some point within the sidewall or on the opposite side of the sidewall, then the "area" would be 0.002 mm$^2$ since that is the minimum or smallest planar area for flow through the opening in the sidewall. If the hole is square or rectangular, the "area" would be the length times the width of the planar area. For any other shapes, the "area" can be determined by conventional mathematical calculations well known to those skilled in the art. For example, the "area" of an irregular shaped opening is found by fitting shapes to fill the planar area of the opening, calculating the area of each shape and adding together the area of each shape.

Openings 1232 can be positioned extending along on a sidewall of the tube 1222 in any direction desired, such as longitudinal and/or axial. In some examples, spacing between the openings 1232 can range from about 1.5 mm to about 15 mm. Fluid passes through one or more of the perforations, drainage ports, or openings 1232 and into the drainage lumen 1234. Desirably, the openings 1232 are positioned so that they are not occluded by tissues of the ureters 6, 8 or kidney when negative pressure is applied to the drainage lumen 1224. For example, as described herein, openings 1234 can be positioned on interior portions of coils or other structures of the retention portion 1230 to avoid occlusion of the openings 1232. In some examples, the middle portion 1226 and proximal portion 1228 of the tube 1222 can be essentially free of or free from perforations, ports, holes or openings to avoid occlusion of openings along those portions of the tube 1222. In some examples, a portion 1226, 1228 which is essentially free from perforations or openings includes substantially fewer openings than other portions of the tube 1222. For example, a total area of openings 1232 of the distal portion 1218 may be greater than or substantially greater than a total area of openings of the proximal portion 1226 and/or the distal portion 1228 of the tube 1222.

In some examples, the openings 1232 are sized and spaced to improve fluid flow through the retention portion 1230. In particular, the present inventors have discovered that when a negative pressure is applied to the drainage lumen 1224 of the catheter 1212 a majority of fluid is drawn into the drainage lumen 1224 through proximal-most perforations or openings 1232. In order to improve flow dynamics so that fluid is also received through more distal openings and/or through the open distal end 1220 of the tube 1222, larger size or a greater number of openings can be provided toward the distal end of the retention portion 1230. For example, a total area of openings 1232 on a length of tube 1222 near a proximal end of the retention portion 1230 may be less than a total area of openings 1232 of a similar sized length of the tube 1222 located near the open distal end 1220 of the tube 1222. In particular, it may be desirable to produce a flow distribution through the drainage lumen 1224 in which less than 90%, preferably less than 70%, and, more preferably, less than 55% of fluid flow is drawn into the drainage lumen 1224 through a single opening 1232 or a small number of openings 1232 positioned near the proximal end of the retention portion 1230.

In many examples, the openings 1232 are generally a circular shape, though triangular, elliptical, square, diamond, and any other opening shapes may also be used. Further, as will be appreciated by one of ordinary skill in the art, a shape of the openings 1232 may change as the tube 1222 transitions between an uncoiled or elongated position and a coiled or deployed position. It is noted that while the shape of the openings 1232 may change (e.g., the orifices may be circular in one position and slightly elongated in the other position), the area of the openings 1232 is substantially similar in the elongated or uncoiled position compared to the deployed or coiled position.

Helical Coil Retention Portion

Referring now to FIGS. 30A-30E, an exemplary retention portion 1230 comprises helical coils 1280, 1282, 1284. In some examples, the retention portion 1230 comprises a first or half coil 1280 and two full coils, such as a second coil 1282 and a third coil 1284. As shown in FIGS. 30A-30D, in some examples, the first coil comprises a half coil extending from 0 degrees to 180 degrees around a curvilinear central axis A of the retention portion 1230. In some examples, as shown the curvilinear central axis A is substantially straight and co-extensive with a curvilinear central axis of the tube 1222. In other examples, the curvilinear central axis A of the retention portion 1230 can be curved giving the retention portion 1230 a cornucopia shape. The first coil 1280 can have a diameter D1 of about 1 mm to 20 mm and preferably about 8 mm to 10 mm. The second coil 1282 can be a full coil extending from 180 degrees to 540 degrees along the retention portion 1230 having a diameter D2 of about 5 mm to 50 mm, preferably about 10 mm to 20 mm, and more preferably about 14 mm±2 mm. The third coil 1284 can be a full coil extending between 540 degrees and 900 degrees and having a diameter D3 of between 5 mm and 60 mm, preferably about 10 mm to 30 mm, and more preferably about 18 mm±2 mm. In other examples, multiple coils 1282, 1284 can have the same inner and/or outer diameter. For example, an outer diameter of the full coils 1282, 1284, can each be about 18±2 mm.

In some examples, an overall height H1 of the retention portion 1230 ranges from about 10 mm to about 30 mm and, preferably about 18±2 mm. A height H2 (shown in FIG. 30E) of a gap between coils 1284, namely between the sidewall of the tube 1222 of the first coil 1280 and the adjacent sidewall of the tube 122 of the second coil 1282 is less than 3.0 mm, preferably between about 0.25 mm and 2.5 mm, and more preferably between about 0.5 mm and 2.0 mm.

The retention portion 1230 can further comprise a distal-most curved portion 1290. For example, the distal most portion 1290 of the retention portion 1230, which includes the open distal end 1220 of the tube 1222, can be bent inwardly relative to a curvature of the third coil 1284. For example, a curvilinear central axis X1 (shown in FIG. 30D) of the distal-most portion 1290 can extend from the distal end 1220 of the tube 1222 toward the curvilinear central axis A of the retention portion 1230.

The retention portion 1230 is capable of moving between a contracted position, in which the retention portion 1230 is straight for insertion into the patient's urinary tract, and the deployed position, in which the retention portion 1230 comprises the helical coils 1280, 1282, 1284. Generally, the tube 1222 is naturally biased toward the coiled configuration. For example, an uncoiled or substantially straight guidewire can be inserted through the retention portion 1230 to maintain the retention portion 1230 in its straight contracted position, as shown for example in FIGS. 31-35. When the guidewire is removed, the retention portion 1230 naturally transitions to its coiled position.

In some examples, the openings 1232 are disposed essentially only or only on a radially inwardly facing side 1286 of the coils 1280, 1282, 1284 to prevent occlusion or blockage of the openings 1232. A radially outwardly facing side 1288 of the coils 1280, 1282, 1284 may be essentially free of the openings 1232. In similar examples, a total area of openings 1232 on the inwardly facing side 1286 of the retention portion 1230 can be substantially greater than a total area of openings 1232 on the radially outwardly facing side 1288 of the retention portion 1230. Accordingly, when negative pressure is induced in the ureter and/or renal pelvis, mucosal tissue of the ureter and/or kidney may be drawn against the retention portion 1230 and may occlude some openings 1232 on the outer periphery of the retention portion 1230. However, openings 1232 located on the radially inward side 1286 of the retention portion 1230 are not appreciably occluded when such tissues contact the outer periphery of the retention portion 1230. Therefore, risk of injury to the tissues from pinching or contact with the drainage openings 1232 can be reduced or eliminated.

Hole or Opening Distribution Examples

In some examples, the first coil 1280 can be free or essentially free from openings. For example, a total area of openings on the first coil 1280 can be less than or substantially less than a total area of openings of the full coils 1282, 1284. Examples of various arrangements of holes or openings which could be used for a coiled retention portion (such as coiled retention portion 1230 shown in FIGS. 30A-30E), are illustrated in FIGS. 31-34. As shown in FIGS. 31-34, a retention portion is depicted in its uncoiled or straight position, as occurs when a guidewire is inserted through the drainage lumen.

Figure 31:
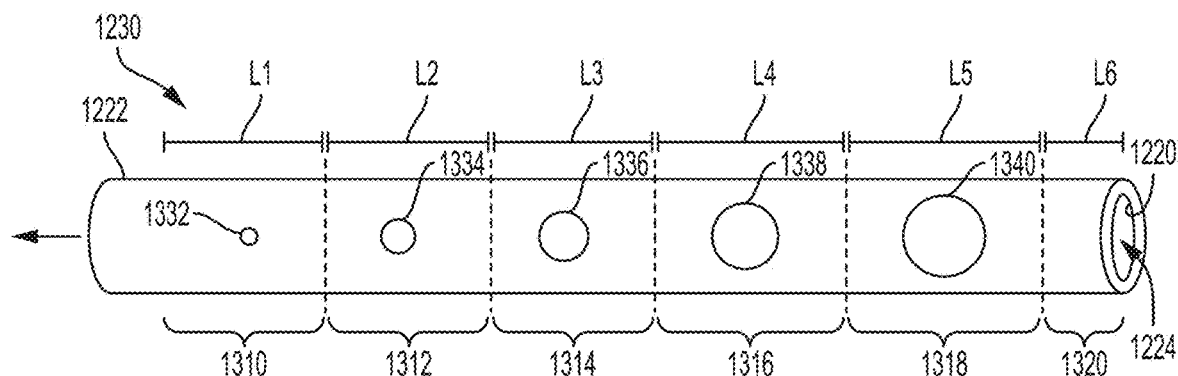
FIG. 31 is a schematic drawing of a retention portion of a ureteral catheter in a constrained or linear position according to an example of the disclosure.

An exemplary retention portion 1330 is illustrated in FIG. 31. In order to more clearly describe positioning of openings of the retention portion 1330, the retention portion 1330 is referred to herein as being divided into a plurality of sections or perforated sections, such as a proximal-most or first section 1310, a second section 1312, a third, section 1314, a fourth section 1316, a fifth section 1318, and a distal-most or sixth section 1320. One of ordinary skill in the art would understand that additional sections can be included, if desired. As used herein, "section" refers to a discrete length of the tube 1322 within the retention portion 1330. In some examples, sections are equal in length. In other examples, some sections can have the same length, and other sections can have a different length. In other examples, each section has a different length. For example, sections can have a length L1-L6 of between about 5 mm and about 35 mm, and preferably between about 5 mm and 15 mm.

In some examples, each section comprises one or more openings. In some examples, each section each comprises a single opening 1332. In other examples, the first section 1310 includes a single opening 1332 and other sections comprise multiple openings 1332. In other examples, different sections comprise one or more openings 1332, each of the opening(s) having a different shape or different total area.

In some examples, such as the retention portion 1230 shown in FIGS. 30A-30E, the first or half coil 1280, which extends from 0 to about 180 degrees of the retention portion 1230 can be free from or essentially free from openings. The second coil 1282 can include the first section 1310 extending between about 180 and 360 degrees. The second coil 1282 can also include the second and third sections 1312, 1314 positioned between about 360 degrees and 540 degrees of the retention portion 1230. The third coil 1284 can include the fourth and fifth sections 1316, 1318 positioned between about 540 degrees and 900 degrees of the retention portion 1230.

In some examples, the openings 1332 can be sized such that a total area of openings of the first section 1310 is less than a total area of openings of the adjacent second section 1312. In a similar manner, if the retention portion 1330 further comprises a third section 1314, then openings of a third section 1314 can have a total area that is greater than the total area of the openings of the first section 1310 or the second section 1312. Openings of the fourth 1316, fifth 1318, and sixth 1320 sections may also have a gradually increasing total area and/or number of openings to improve fluid flow through the tube 1222.

As shown in FIG. 31, the retention portion 1230 of the tube includes five sections 1310, 1312, 1314, 1316, 1318 each of which includes a single opening 1332, 1334, 1336, 1338, 1340. The retention portion 1230 also includes a sixth section 1320 which includes the open distal end 1220 of the tube 1222. In this example, the opening 1332 of the first section 1310 has the smallest total area. For example, a total area of the opening 1332 of the first section can be between about 0.002 mm² and about 2.5 mm², or between about 0.01 mm² and 1.0 mm², or between about 0.1 mm² and 0.5 mm². In one example, the opening 1332 is about 55 mm from the distal end 1220 of the catheter, has a diameter of 0.48 mm, and an area of about 0.18 mm². In this example, a total area of an opening 1334 of the second section 1312 is greater than the total area of an opening 1332 of the first section 1310 and can range in size from about 0.01 mm² and 1.0 mm². The third 1336, fourth 1338, and fifth 1350 openings can also range in size from about 0.01 mm² and 1.0 mm². In one example, the second opening 1334 is about 45 mm from the distal end of the catheter 1220, has a diameter of about 0.58 mm, and an area of about 0.27 mm². The third opening 1336 can be about 35 mm from the distal end of the catheter 1220 and have a diameter of about 0.66 mm. The fourth opening 1338 can be about 25 mm from the distal end 1220 and have a diameter of about 0.76 mm. The fifth opening 1340 can be about 15 mm from the distal end 1220 of the catheter and have a diameter of about 0.889 mm. In some examples, the open distal end 1220 of the tube 1222 has the largest opening having an area of between about 0.5 mm² to about 5.0 mm² or more. In one example, the open distal end 1220 has a diameter of about 0.97 mm and an area of about 0.74 mm².

As described herein, openings 1332, 1334, 1336, 1338, 1340 can be positioned and sized so that a volumetric flow rate of fluid passing through the first opening 1332 more closely corresponds to a volumetric flow rate of openings of more distal sections when negative pressure is applied to the drainage lumen 1224 of the catheter 1212. As described above, if each opening were the same area, then when negative pressure is applied to the drainage lumen 1224, the volumetric flow rate of fluid passing through the proximal-most of first opening 1332 would be substantially greater than a volumetric flow rate of fluid passing through openings 1334 closer to the distal end 1220 of the retention portion 1330. While not intending to be bound by any theory, it is believed that when negative pressure is applied, the pressure differential between the interior of the drainage lumen 1224 and external to the drainage lumen 1224 is greater in the region of the proximal-most opening and decreases at each opening moving toward the distal end of the tube. For example, sizes and positions of the openings 1332, 1334, 1336, 1338, 1340 can be selected so that a volumetric flow rate for fluid which flows into openings 1334 of the second section 1312 is at least about 30% of a volumetric flow rate of fluid which flows into the opening(s) 1332 of the first section 1310. In other examples, a volumetric flow rate for fluid flowing into the proximal-most or first section 1310 is less than about 60% of a total volumetric flow rate for fluid flowing through the proximal portion of the drainage lumen 1224. In other examples, a volumetric flow rate for fluid flowing into openings 1332, 1334 of the two proximal-most sections (e.g., the first section 1310 and the second section 1312) can be less than about 90% of a volumetric flow rate of fluid flowing through the proximal portion of the drainage lumen 1224 when a negative pressure, for example a negative pressure of about −45 mmHg, is applied to the proximal end of the drainage lumen.

As will be appreciated by one of ordinary skill in the art, volumetric flow rate and distribution for a catheter or tube comprising a plurality of openings or perforations can be directly measured or calculated in a variety of different ways. As used herein, "volumetric flow rate" means actual measurement of the volumetric flow rate downstream and adjacent to each opening or using a method for "Calculated Volumetric Flow Rate" described below.

For example, actual measurement of the dispersed fluid volume over time can be used to determine the volumetric flow rate through each opening 1332, 1334, 1336, 1338, 1340. In one exemplary experimental arrangement of an ex vivo test of dispersed fluid volume, a multi-chamber vessel, such as a sleeve or box, comprising individual chambers sized to receive sections 1310, 1312, 1314, 1316, 1318, 1320 of the retention portion 1330 could be sealed around and enclose the retention portion 1330. Each opening 1332, 1334, 1336, 1338, 1340 could be sealed in one of the chambers. In this arrangement, each chamber encloses an identical volume and is filled with an equal amount of fluid, such that an initial fluid pressure within each chamber is identical. Experimental conditions may be selected to be similar to fluid collection conditions in the body. For example, a temperature of 37° C. may be used and the chambers may be filled with urine having an approximate density of 1.03 g/mL and had a coefficient of friction μ of 8.02×10-3 Pa·S (8.02×10-3 kg/s·m). Negative pressure of 100 mmHg or less can be applied to a proximal end of the catheter tube for fluid collection. In some examples, a negative pressure of −15 mmHg, −30 mmHg, or −45 mmHg is applied.

An amount of fluid volume drawn from the respective chambers into the tube 3222 through each opening 1332, 1334, 1336, 1338, 1340 could be measured to determine an amount of fluid volume drawn into each opening over time when a negative pressure is applied. For example, each chamber may be initially filled with a predetermined fluid volume of, for example, 100 mL of urine. Negative pressure can be applied by a pump for a predetermined period of time, such as 30 seconds, 1 minute, 5 minutes, or 15 minutes. After the predetermined period of time, the pump can be shut off and the fluid remaining in each chamber can be measured. A difference between the measured fluid remaining and the initial fluid amount corresponds to an amount of fluid drawn into the drainage lumen of the tube through each opening. The cumulative amount of fluid volume collected in the tube 1222 by a negative pressure pump system would be equivalent to the sum of fluid drawn into each opening 1332, 1334, 1336, 1338, 1340.

Figure 35A:
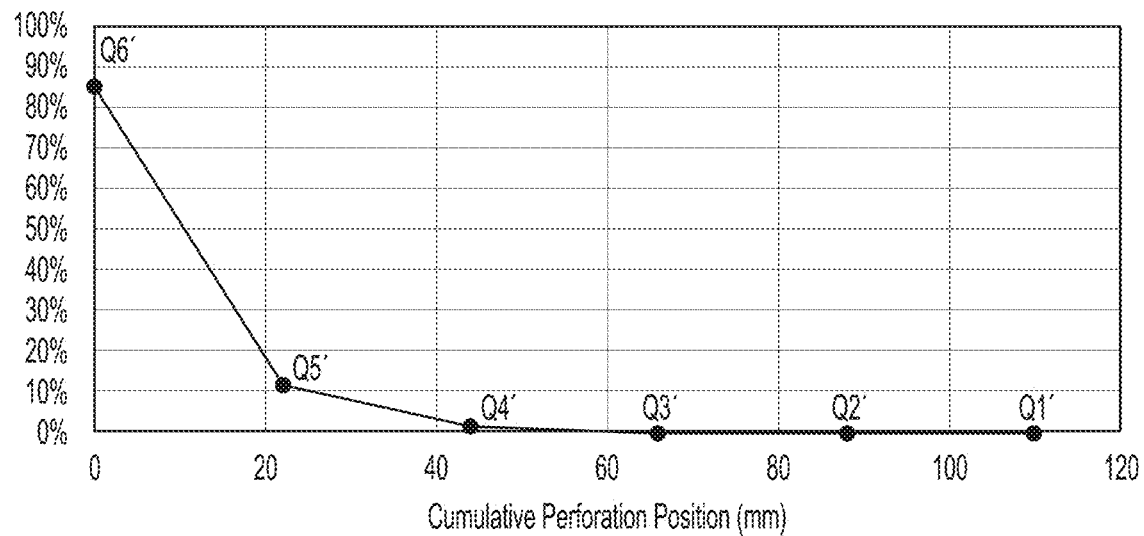
FIG. 35A is a graph showing a percentage of fluid flow through openings of an exemplary ureteral catheter as a function of position according to an example of the disclosure.
Figure 35B:
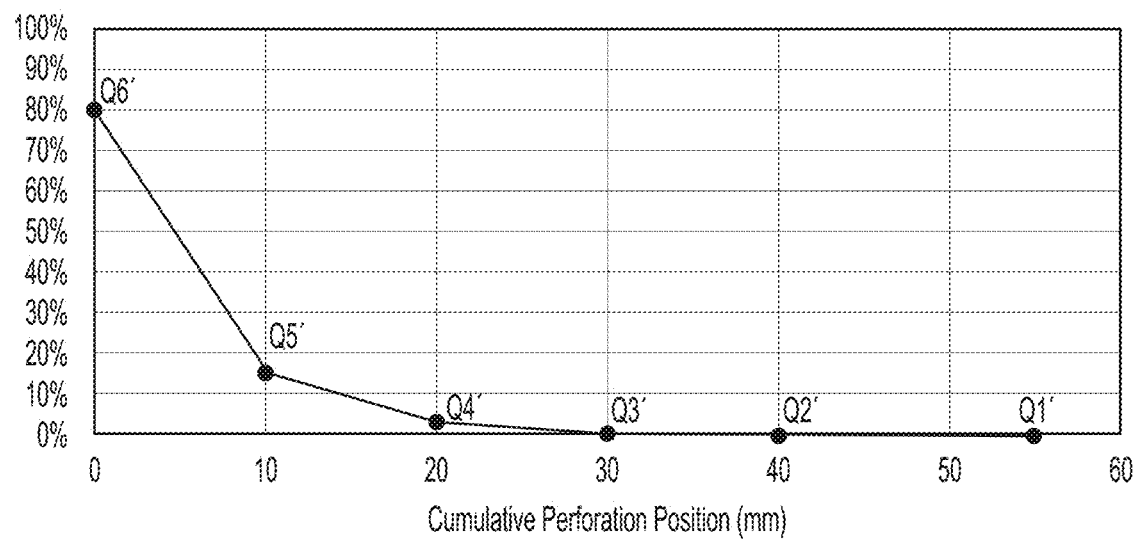
FIG. 35B is a graph showing a percentage of fluid flow through openings of another exemplary ureteral catheter as a function of position according to an example of the disclosure.
Figure 35C:
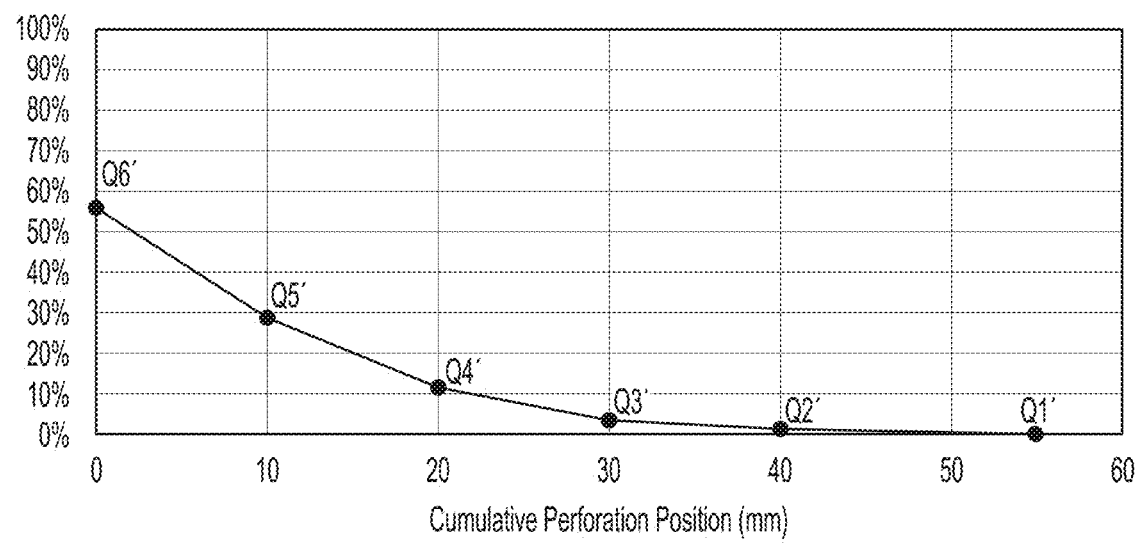
FIG. 35C is a graph showing a percentage of fluid flow through openings of another exemplary ureteral catheter as a function of position according to an example of the disclosure.

Alternatively, volumetric fluid flow rate through different openings 1332, 1334, 1336, 1338, 1340 can be calculated mathematically using equations for modeling fluid flow through a tubular body. For example, volumetric flow rate of fluid passing through openings 1332, 1334, 1336, 1338, 1340 and into the drainage lumen 1224 can be calculated based on a mass transfer shell balance evaluation, as described in detail below in connection with the Mathematical Examples and FIGS. 35A-35C. Steps for deriving mass balance equations and for calculating a flow distribution between or volumetric flow rates for the openings 1332,

1334, 1336, 1338, 1340 are also described in detail below in connection with FIGS. 35A-35C.

Figure 32:
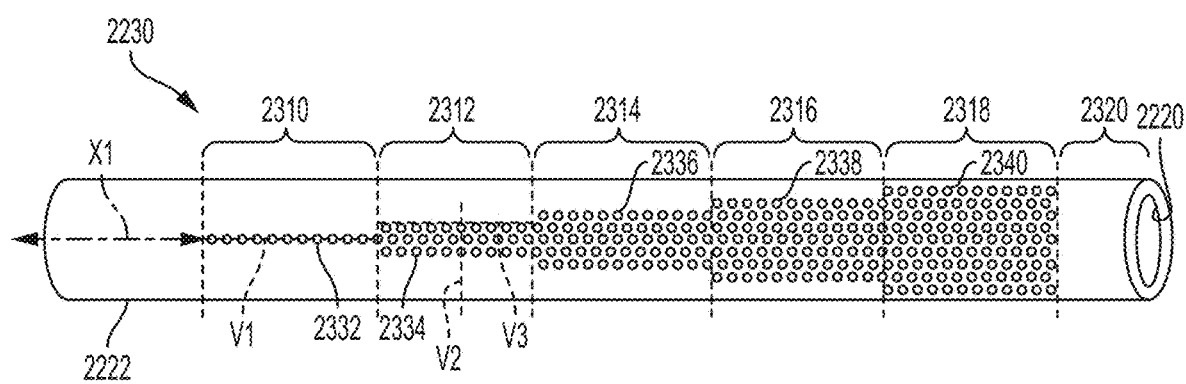
FIG. 32 is a schematic drawing of another example of a retention portion of a ureteral catheter in a constrained or linear position according to an example of the disclosure.

Another exemplary retention portion 2230 with openings 2332, 2334, 2336, 2338, 2340 is illustrated in FIG. 32. As shown in FIG. 32, the retention portion 2230 comprises numerous smaller perforations or openings 2332, 2334, 2336, 2338, 2340. Each of the openings 2332, 2334, 2336, 2338, 2340 can have a substantially identical minimum area through the sidewall of the tube 2222. As shown in FIG. 32, the retention portion 2330 comprises six sections 2310, 2312, 2314, 2316, 2318, 2320, such as are described above, wherein each section comprises a plurality of the openings 2332, 2334, 2336, 2338, 2340. In the example shown in FIG. 32, a number of openings 2332, 2334, 2336, 2338, 2340 per section increases toward the distal end 2220 of the tube 1222, such that a total area of openings 1332 in each section increases compared to a proximally adjacent section.

As shown in FIG. 32, openings 2332 of the first section 2310 are arranged along a first virtual line V1, which is substantially parallel to a curvilinear central axis X1 of the retention portion 2230. Openings 2334, 2336, 2338, 2340 of the second 2312, third 2314, fourth 2316, and fifth 2318 sections, respectively, are positioned on the sidewall of the tube 2222 in a gradually increasing number of rows, such that openings 2334, 2336, 2338, 2340 of these sections also line up around a circumference of the tube 2222. For example, some of the openings 2334 of the second section 2312 are positioned such that a second virtual line V2 extending around a circumference of the sidewall of the tube 2222 contacts at least a portion of multiple openings 2334. For example, the second section 2312 can comprise two or more rows of perforations or openings 2334, in which each opening 2334 has an equal minimum area. Further, in some examples, at least one of the rows of the second section 2312 can be aligned along a third virtual line V3, which is parallel with the curvilinear central axis X1 of the tube 2222, but is not co-extensive with the first virtual line V1. In a similar manner, the third section 2314 can comprise five rows of perforations or openings 2336, in which each opening 2336 has an equal minimum area; the fourth section 2316 can comprise seven rows of perforations or openings 2338; and the fifth section 2318 can comprise nine rows of perforations or openings 2340. As in previous examples, the sixth section 2320 comprises a single opening, namely, the open distal end 2220 of the tube 2222. In the example of FIG. 32, each of the openings has the same area, although the area of one or more openings can be different if desired.

Figure 33:
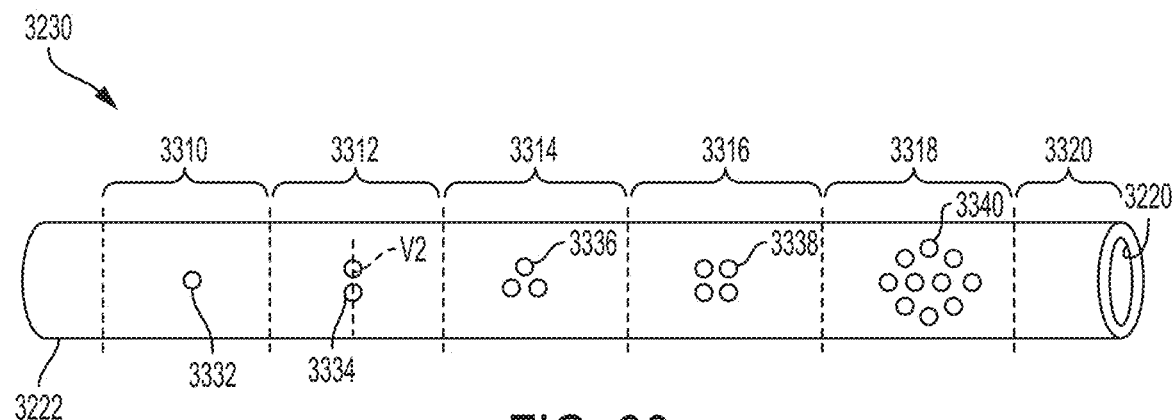
FIG. 33 is a schematic drawing of another example of a retention portion of a ureteral catheter in a constrained or linear position according to an example of the disclosure.

Another exemplary retention portion 3230 with openings 3332, 3334, 3336, 3338, 3340 is illustrated in FIG. 33. The retention portion 3230 of FIG. 33 includes a plurality of similarly sized perforations or openings 3332, 3334, 3336, 3338, 3340. As in previous examples, the retention portion 3230 can be divided into six sections 3310, 3312, 3314, 3316, 3318, 3320, each of which comprises at least one opening. The proximal-most or first section 3310 includes one opening 3332. The second section 3312 includes two openings 3334 aligned along the virtual line V2 extending around a circumference of the sidewall of the tube 3222. The third section 3314 comprises a grouping of three openings 3336, positioned at vertices of a virtual triangle. The fourth section 3316 comprises a grouping of four openings 3338 positioned at corners of a virtual square. The fifth section 3318 comprises ten openings 3340 positioned to form a diamond shape on the sidewall of the tube 3222. As in previous examples, the sixth section 3320 comprises a single opening, namely, the open distal end 3220 of the tube 3222. The area of each opening can range from about 0.002 mm$^2$ and about 2.5 mm$^2$.

Figure 34:
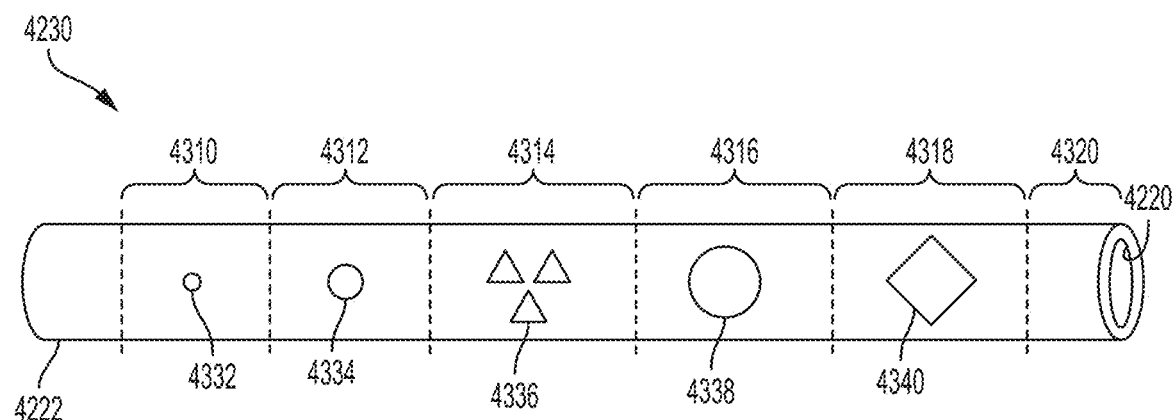
FIG. 34 is a schematic drawing of another example of a retention portion of a ureteral catheter in a constrained or linear position according to an example of the disclosure.

Another exemplary retention portion 4230 with openings 4332, 4334, 4336, 4338, 4340 is illustrated in FIG. 34. The openings 4332, 4334, 4336, 4338, 4340 of the retention portion 4330 have different shapes and sizes. For example, the first section 4310 includes a single circular opening 4332. The second section 4312 has a circular opening 4334 with a larger cross-sectional area than the opening 4332 of the first section 4310. The third section 4314 comprises three triangular-shaped openings 4336. The fourth section 4316 comprises a large circular opening 4338. The fifth section 4318 comprises a diamond-shaped opening 4340. As in previous examples, the sixth section 4320 comprises the open distal end 4220 of the tube 4222. FIG. 34 illustrates one example of an arrangement of different shapes of openings in each section. It is understood that the shape of each opening in each section can be independently selected, for example the first section 4310 can have one or more diamond-shaped openings or other shapes. The area of each opening can range from about 0.002 mm$^2$ and about 2.5 mm$^2$.

EXAMPLES

Calculation of Volumetric Flow Rate and Percentage of Flow Distribution

Figure 38:
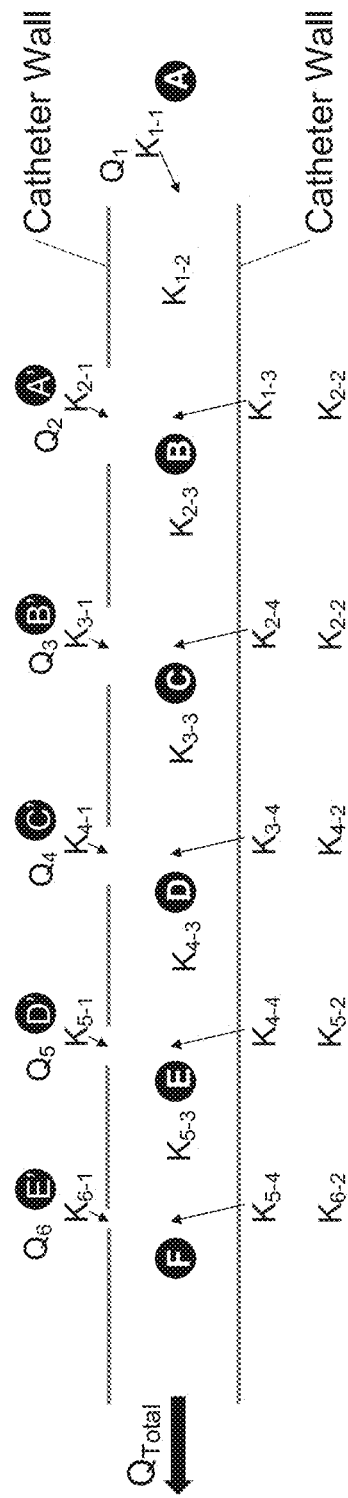
FIG. 38 is a schematic drawing of a retention portion of a ureteral catheter showing "Stations" for calculating fluid flow coefficients for a mass transfer balance evaluation according to an example of the present disclosure.
Figure 39:
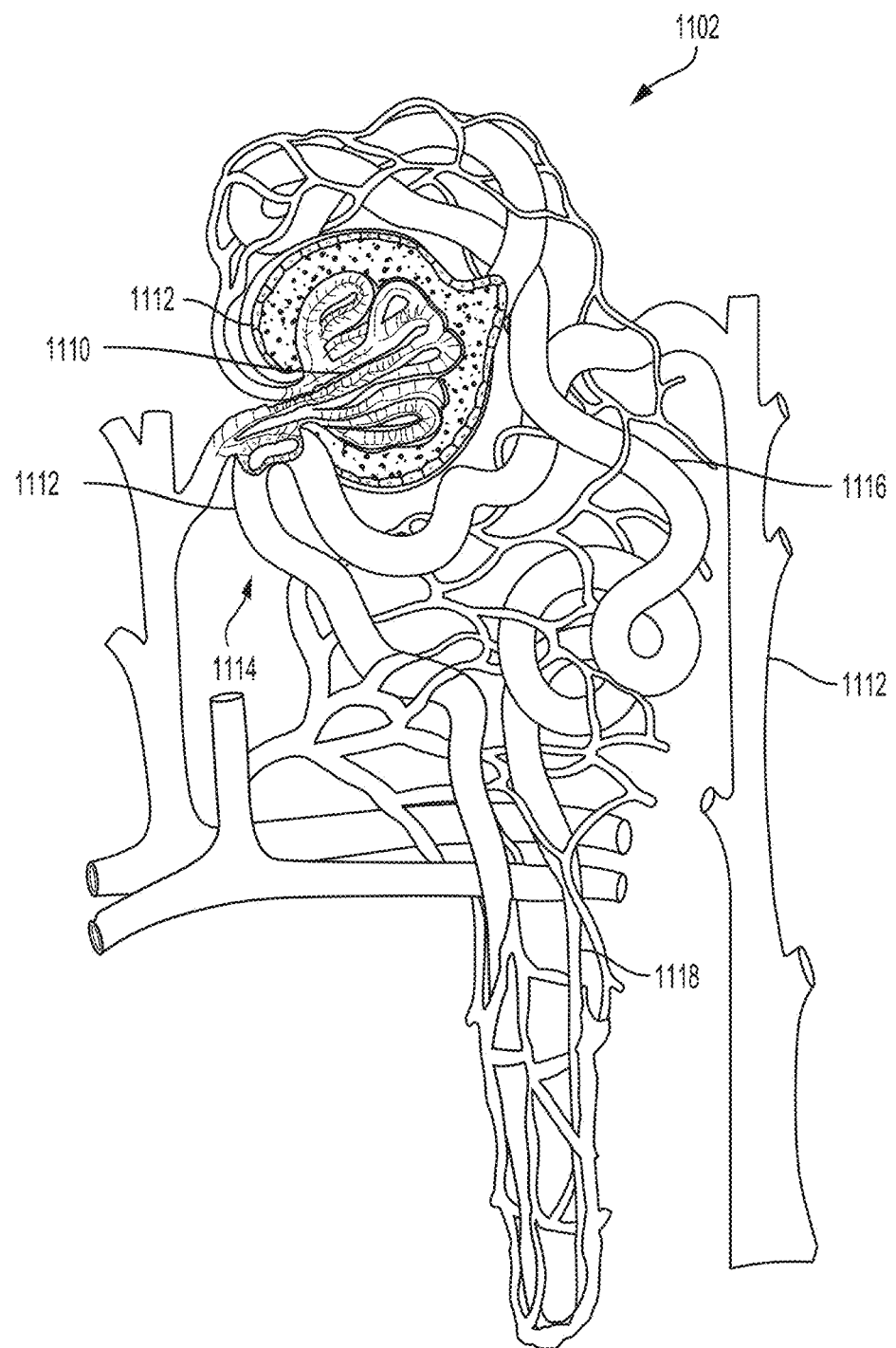
FIG. 39 is a schematic drawing of a nephron and surrounding vasculature showing a position of the capillary bed and convoluted tubules.

Having described various arrangements of openings for retention portions of the ureteral catheter 1212, a method for determining the Calculated Percentage of Flow Distribution and Calculated Volumetric Flow Rate through the catheter will now be described in detail. A schematic drawing of an exemplary catheter with sidewall openings showing a position of portions of the tube or drainage lumen used in the following calculations is shown in FIG. 38. Calculated Percentage of Flow Distribution refers to a percentage of total fluid flowing through proximal portions of the drainage lumen which enters the drainage lumen through different openings or sections of the retention portion. Calculated Volumetric Flow rate refers to fluid flow per unit time through different portions of the drainage lumen or openings of the retention portion. For example, a volumetric flow rate for a proximal portion of the drainage lumen describes a rate of flow for a total amount of fluid passing through the catheter. A volumetric flow rate for an opening refers to a volume of fluid which passes through the opening and into the drainage lumen per unit time. In Tables 3-5 below flow is described as a percentage of total fluid flow or of a total volumetric flow rate for a proximal portion of the drainage lumen. For example, an opening having a flow distribution of 100% means that all fluid entering the drainage lumen passed through the opening. An opening having a distribution of 0% would indicate that none of the fluid in the drainage lumen entered the drainage lumen through that opening.

These volumetric flow rate calculations were used to determine and model fluid flow through the retention portion 1230 of the ureter catheter 1212 shown in FIGS. 27-34. Further, these calculations show that adjusting the area of openings and linear distribution of openings along the retention portion affects a distribution of fluid flow through different openings. For example, reducing the area of the proximal-most opening decreases the proportion of fluid drawn into the catheter through the proximal most opening and increases the proportion of fluid drawn into more distal openings of the retention portion.

For the following calculations, a tube length of 86 cm having an inner diameter of 0.97 mm and an end hole inner diameter of 0.97 mm was used. Density of urine was 1.03 g/mL and had a coefficient of friction μ of 8.02×10-3 Pa·S (8.02×10-3 kg/s·m) at 37° C. The urine volumetric flow rate passing through the catheter was 2.7 ml per minute ($Q_{Total}$) as determined by experimental measurement.

charts) to the pipe cross-sectional area (referred to as A3 in the charts) and the ratio of the inlet orifice volumetric flow rate (Q1 in the charts) to the resulting combined pipe volumetric flow rate (Q3 in the charts). For example, for an area ratio of 0.6 between an area of the opening and an area of the drainage lumen, the following Flow Junction Loss Coefficients ($K_{13}$ and $K_{23}$) would be used.

| Flow Ratio ($Q_1/Q_3$) | 0.1 | 0.2 | 0.3 | 0.4 | 0.5 | 0.6 | 0.7 | 0.8 | 0.9 | 1.0 |
| --- | --- | --- | --- | --- | --- | --- | --- | --- | --- | --- |
| $K_{13}$ | −0.58 | −0.04 | 0.11 | 0.45 | 0.75 | 1.13 | 1.48 | 1.81 | 2.16 | 2.56 |
| $K_{23}$ | 0.15 | 0.27 | 0.39 | 0.48 | 0.56 | 0.63 | 0.69 | 0.72 | 0.74 | 0.76 |

Calculated Volumetric Flow Rate is determined by a volumetric mass balance equation in which a sum total of volumetric flow through all perforations or openings 1232 of the five sections of the retention portion (referred to herein as volumetric flow $Q_2$ to $Q_6$) and through the open distal end 1220 (referred to herein as volumetric flow $Q_1$) equals the total volumetric flow ($Q_{Total}$) exiting the proximal end of the tube 1222 at a distance of 10 cm to 60 cm away from the last proximal opening, as shown in Equation 2.

$$Q_{Total} = Q_1 + Q_2 + Q_3 + Q_4 + Q_5 + Q_6 \quad \text{(Equation 2)}$$

A Modified Loss Coefficient (K') for each of the sections is based on three types of loss coefficients within the catheter model, namely: an Inlet Loss Coefficient taking into account a pressure loss resulting at a pipe inlet (e.g., the openings and open distal end of the tube 1222); a Friction Loss Coefficient which takes into account pressure loss resulting from friction between the fluid and pipe wall; and a Flow Junction Loss Coefficient taking into account pressure loss resulting from the interaction of two flows coming together.

The Inlet Loss Coefficient is dependent on a shape of the orifice or opening. For example, a tapered or nozzle shaped orifice would increase flow rate into the drainage lumen 1224. In a similar manner, a sharp-edged orifice would have different flow properties than an orifice with less defined edges. For purposes of the following calculations, it is assumed that the openings 1232 are side orifice openings and the open distal end 1220 of the tube 1222 is a sharp-edged opening. The cross sectional area of each opening is considered constant through the tube sidewall.

The Friction Loss Coefficient approximates pressure loss resulting from friction between the fluid and the adjacent inner wall of the tube 1222. Friction loss is defined according to the following equations:

$$Re = \frac{\rho U D}{\mu} \quad \text{(Equation 3.1)}$$

$$f = \frac{c_f}{Re} \quad \text{(Equation 3.2)}$$

$$K_{1-2} = K_{2-3} = K_{3-3} = K_{4-3} = K_{5-3} = K_f = f \frac{L}{D} \quad \text{(Equation 3.3)}$$

The Flow Junction Loss Coefficients are derived from loss coefficients for combining flow at a branch angle of 90 degrees. Values for the loss coefficients were obtained from Charts 13.10 and 13.11 of Miller D S, *Internal Flow Systems*, 1990, incorporated by reference herein. The charts use the ratio of the inlet orifice area (referred to as A1 in the To calculate the Total Manifold Loss Coefficient (K), it is necessary to separate the model into so-called "reference stations" and progressively work through and balance the pressure and flow distributions of the two paths (e.g., flow through the opening and flow through the drainage lumen of the tube) to reach each station starting from the distal tip to the most proximal "Station". A graphical representation of the different stations used for this calculation is shown in FIG. 38. For example, a most-distal "Station" A is the distal open end 1220 of the tube 122. A second Station A' is the distal most opening on the sidewall of the tube 122 (e.g., the opening(s) of the fifth section 1318 in FIGS. 31-34). The next station B is for flow through the drainage lumen 1224 just proximal to the A' opening.

To calculate loss between Station A (the distal opening) and Station B for fluid entering through the open distal end of the tube 1222 (Path 1), the modified loss coefficient (K') is equal to:

$$K' = \text{Inlet Loss} + \text{Friction Loss} + \text{Flow Junction Loss} \quad \text{(Equation 4.1)}$$

$$K'_B = K_{1-1} \times \left(\frac{A_{Pipe}}{A_1} \times Q_1\right)^2 + K_{1-2} \times Q_1^2 + K_{1-3} \times (Q_1 + Q_2)^2 \quad \text{(Equation 4.2)}$$

In a similar manner, a second path to Station B is through the opening(s) 1334 of the fifth section 1318 (shown in FIGS. 31-34) of the retention portion 1330. A modified loss calculation for Path 2 is calculated as follows:

$$K' = \text{Inlet Loss} + \text{Flow Junction Loss} \quad \text{(Equation 5.1)}$$

$$K'_B = K_{2-1} \times \left(\frac{A_{Pipe}}{A_2} \times Q_2\right)^2 + K_{2-2} \times (Q_1 + Q_2)^2 \quad \text{(Equation 5.2)}$$

The modified loss coefficients of both Path 1 and Path 2 must equate to ensure the volumetric flow rates ($Q_1$ and $Q_2$) reflect the balanced distribution within the manifold at Station B. The volumetric flow rates are adjusted until equal modified loss coefficients for both paths is achieved. The volumetric flow rates can be adjusted because they represent a fractional portion of a total volumetric flow rate ($Q'_{Total}$), which is assumed to be unity for the purpose of this step-by-step solution. Upon equating the two modified loss coefficients, one can then proceed to equating the two paths to reach station C (the fourth section 1316 in FIGS. 31-34).

Loss coefficients between Station B (flow through drainage lumen in the fifth section 1318) and Station C (flow through lumen in the fourth section 1316) are calculated in a similar manner as shown by Equations 5.1 and 5.2). For example, for Path 1 (Station B to Station C), the modified loss coefficient (K') for the opening(s) of the fourth section 1316 is defined as:

$K'$=Loss to Station $B$+Friction Loss+Flow Junction Loss (Equation 6.1)

$K_C' = K_B' + K_{2-3} \times (Q_1+Q_2)^2 + K_{2-4} \times (Q_1+Q_2+Q_3)^2$ (Equation 6.2)

For Path 2 (Station B to C), the modified loss coefficient (K') based on the flow area of the opening(s) of the fourth section 1316 are defined as:

$K'$ = Inlet Loss + Flow Junction Loss (Equation 7.1)

$K_C' = K_{3-1} \times \left(\dfrac{A_{Pipe}}{A_3} \times Q_3\right)^2 + K_{3-2} \times (Q_1+Q_2+Q_3)^2$ (Equation 7.2)

As with the previous stations, the modified loss coefficients of both Path 1 and Path 2 must equate to ensure the volumetric flow rates ($Q_1$, $Q_2$, and $Q_3$) reflect the balanced distribution within the manifold up to Station C. Upon equating the two modified loss coefficients, one can then proceed to equating the two paths to reach Station D, Station E, and Station F. The step-by-step solution process proceeds through each station as demonstrated until calculating the modified loss coefficient for the final station, Station F in this case. The Total Loss Coefficient (K) for the manifold can then be calculated using an actual $Q_{Total}$ (volumetric flow rate through a proximal portion of the drainage lumen) determined through experimental measurement.

$$K = \dfrac{K_F'}{Q_{Total}}$$ (Equation 8)

The fractional volumetric flow rates calculated through the step-by-step exercise can then be multiplied by the actual total volumetric flow rate ($Q_{Total}$) to determine the flow through each opening 1232 (shown in FIGS. 30A-3E) and open distal end 1220.

EXAMPLES

Examples are provided below and shown in Tables 3-5 and FIGS. 35A-35C for the calculated volumetric flow rates.

Example 1

Example 1 illustrates a distribution of fluid flow for a retention member tube with different sized openings, which corresponds to the embodiment of the retention member 1330 shown in FIG. 31. As shown in Table 3, the proximal most opening ($Q_6$) had a diameter of 0.48 mm, the distal-most opening ($Q_5$) on the sidewall of the tube had a diameter of 0.88 mm, and the open distal end ($Q_6$) of the tube had a diameter of 0.97 mm. Each of the openings was circular.

The Percentage of Flow Distribution and Calculated Volumetric Flow Rate were determined as follows.
Path to Station B Through Distal End of Tube (Path 1)

$f \; 8.4 = C_f / \text{Re} \left(C_f = 64 \text{ for circular cross-section}\right)$ $K_{INLET}$ 0.16

(Contraction coefficient.for sharp edged orifice entering pipe)

$K_{ORIFICE}$ 2.8

(Contraction coefficient.for sharp edged orifice w/ no outlet)

$K_{FRICTION} = f^*(L/D)$ (Dependent on the length between orifices)

Part 1–1 = Inlet loss $coef \times (A_T/A_1 \times Q_1')^2$

Part 1–2 = Catheter friction loss $\times Q_1'^2$

Part 1–3 = Through flow junction loss to station $2 \times (Q_1' + Q_2')^2$ $A_2/A_T = 0.82$ $Q_2'/(Q_1' + Q) = 0.83$ $K_{1-3} = 0.61$ (From Miller, see table above)

Part 1–1 = 0.0000
Part 1–2 = 0.0376
Part 1–3 = 0.0065
$K' = 0.0442$

Path to Station B Through Sidewall Opening (Path 2)

Part 2–1 = Orifice loss $coef \times (A_T/A_2 \times Q_2')^2$

Part 2–2 = Branch flow junction loss to station $2 \times (Q_1' + Q_2')^2$ $A_2/A_T = 0.82$ $Q_2'/(Q_1' + Q_2') = 0.83$ $K_{2-2} = 1.3$ (From Chart 13.10 of Miller)

Part 2–1 = 0.0306
Part 2–3 = 0.0138
$K' = 0.0444$

Path to Station C from Station B (Path 1+Path 2)

Part 2–3 = Catheter friction loss $\times (Q_1' + Q_2')^2$

Part 2–4 = Through flow junction loss to station $3 \times (Q_1' + Q_2' + Q_3')^2$ $A_3/A_T = 0.61$ $Q_3'/(Q_1' + Q_2' + Q_3') = 0.76$ $K_{2-4} = 0.71$ (From Chart 13.11 of Miller)

Loss coefficient to Station 2 = 0.044
Part 2–3 = 0.921
Part 2–4 = 0.130
$K' = 1.095$ Path to Station C Through Sidewall Opening (Path 3)

Part 3–1 = Orifice loss $coef \times (A_T/A_3 \times Q_3')^2$

Part 3–2 = Branch flow junction loss to station $3 \times (Q_1' + Q_2' + Q_3')^2$ $A_3/A_T = 0.61$ $Q_3'/(Q_1' + Q_2' + Q_3') = 0.76$ Part 3–1 = 0.785
Part 3–2 = 0.311
$K' = 1.096$ Path to Station D from Station C (Path 1+Path 2+Path 3)

Part 3-3 = Catheter friction loss $\times (Q'_1 + Q'_2 + Q'_3)^2$

Part 3-4 =

Through flow junction loss to station $4 \times (Q'_1 + Q'_2 + Q'_3 + Q'_4)^2$ $A_4/A_T = 0.46$ $Q'_4/(Q'_1 + Q'_2 + Q'_3 + Q'_4) = 0.70$ $K_{3-4} = 0.77$ (From Chart 13.11 of Miller)

Loss coefficient to Station 4 = 18.6
Part 4-3 = 182.3
Part 4-4 = 13.3
$\overline{\phantom{xxxx} K' = 18.62 \phantom{xxxx}}$ Path to Station D Through Sidewall Opening (Path 4)

Part 4-1 = Orifice loss $coef \times (A_T/A_4 \times Q'_4)^2$

Part 4-2 = Branch flow junction loss to station $4 \times (Q'_1 + Q'_2 + Q'_3 + Q'_4)^2$ $A_4/A_T = 0.46$ $Q'_4/(Q'_1 + Q'_2 + Q'_3 + Q'_4) = 0.70$ $K_{4-2} = 2.4$ (From Chart 13.10 of Miller)

Part 4-1 = 13.59
Part 4-2 = 5.04
$\overline{\phantom{xxxx} K' = 18.62 \phantom{xxxx}}$ Path to Station E from Station D (Path 1+Path 2+Path 3+Path 4)

Part 4-3 = Catheter friction loss $\times (Q'_1 + Q'_2 + Q'_3 + Q'_4)^2$

Part 4-4 =

Through flow junction loss to station $5 \times (Q'_1 + Q'_2 + Q'_3 + Q'_4 + Q'_5)^2$ $A_5/A_T = 0.36$ $Q'_5/(Q'_1 + Q'_2 + Q'_3 + Q'_4 + Q'_5) = 0.65$ $K_{3-4} = 0.78$ (From Chart 13.11 of Miller)

Loss coefficient to Station 4 = 18.6
Part 4-3 = 182.3
Part 4-4 = 13.3
$\overline{\phantom{xxxx} K' = 214.2 \phantom{xxxx}}$ Path to Station E Through Sidewall Opening (Path 5)

Part 5-1 = Orifice loss $coef \times (A_T/A_5 \times Q'_5)^2$

Part 5-2 =

Branch flow junction loss to station $5 \times (Q'_1 + Q'_2 + Q'_3 + Q'_4 + Q'_5)^2$ $A_5/A_T = 0.36$ $Q'_5/(Q'_1 + Q'_2 + Q'_3 + Q'_4 + Q'_5) = 0.65$ $K_{4-2} = 3.3$ (From Chart 13.10 of Miller)

Part 5-1 = 157.8
Part 5-2 = 56.4
$\overline{\phantom{xxxx} K' = 214.2 \phantom{xxxx}}$ Path to Station F from Station E (Through Paths 1-5)

Part 5-3 = Catheter friction loss $\times (Q'_1 + Q'_2 + Q'_3 + Q'_4 + Q'_5)^2$

Part 5-4 =

Through flow junction loss to station $6 \times (Q'_1 + Q'_2 + Q'_3 + Q'_4 + Q'_5 + Q'_6)^2$ $A_6/A_T = 0.24$ $Q'_5/(Q'_1 + Q'_2 + Q'_3 + Q'_4 + Q'_5 + Q'_6) = 0.56$ $K_{3-4} = 0.77$ (From Chart 13.11 of Miller)

Loss coefficient to Station 5 = 214.2
Part 5-3 = 1482.9
Part 5-4 = 68.3
$\overline{\phantom{xxxx} K' = 1765.4 \phantom{xxxx}}$ Path to Station F Through Sidewall Opening (Path 6)

Part 6-1 = Orifice loss $coef \times (A_T/A_6 \times Q'_6)^2$

Part 6-2 =

Branch flow junction loss to station $6 \times (Q'_1 + Q'_2 + Q'_3 + Q'_4 + Q'_5 + Q'_6)^2$ $A_6/A_T = 0.24$ $Q'_6/(Q'_1 + Q'_2 + Q'_3 + Q'_4 + Q'_5 + Q'_6) = 0.56$ $K_{4-2} = 5.2$ (From Chart 13.10 of Miller)

Part 6-1 = 1304.3
Part 6-2 = 461.2
$\overline{\phantom{xxxx} K' = 1765.5 \phantom{xxxx}}$ In order to calculate flow distribution for each "Station" or opening, the calculated K' values were multiplied by actual total volumetric flow rate ($Q_{Total}$) to determine the flow through each perforation and distal end hole. Alternatively, calculated results could be presented as a percentage of total flow or a flow distribution as shown in Table 3. As shown in Table 3 and in FIG. 35C, the Percentage of Flow Distribution (% Flow Distribution) through the proximal most opening (Q6) was 56.1%. Flow through the two proximal-most holes (Q6 and Q5) was 84.6%.

TABLE 3

| Position | % Flow Distribution | Diameter (mm) | Length (mm) | Cumulative Length (mm) |
|---|---|---|---|---|
| $Q_6'$ (proximal) | 56.1% | 0.48 | 0 | 0 |
| $Q_5'$ | 28.5% | 0.58 | 10 | 10 |
| $Q_4'$ | 10.8% | 0.66 | 10 | 20 |
| $Q_3'$ | 3.5% | 0.76 | 10 | 30 |
| $Q_2'$ | 0.9% | 0.88 | 10 | 40 |
| $Q_1'$ (distal) | 0.2% | 0.97 | 15 | 55 |
| $Q_{TOTAL}$ | 100% | | | |

As demonstrated in Example 1, by increasing hole diameter and cross-sectional area from the proximal to distal regions of the retention portion, distribution of fluid flow was more evenly distributed across the entire retention portion.

Example 2

In Example 2, each opening has the same diameter and area. As shown in Table 4 and FIG. 35A, flow distribution through the proximal-most opening is 86.2% of total flow through the tube. Flow distribution through the second opening is 11.9%. Therefore, in this example, it was calculated that 98.1% of fluid passing through the drainage lumen entered the lumen through the two proximal-most openings. Compared to Example 1, Example 2 has increased flow through the proximal end of the tube. Therefore, Example 1 provides a wider flow distribution in which a greater percentage of fluid enters the drainage lumen through openings other than the proximal-most opening. As such, fluid can be more efficiently collected through multiple openings reducing fluid backup and improving distribution of negative pressure through the renal pelvis and/or kidneys.

TABLE 4

| Position | % Flow Distribution | Diameter (mm) | Length (mm) | Cumulative Length (mm) |
|---|---|---|---|---|
| $Q_6'$ (proximal) | 86.2% | 0.88 | 0 | 0 |
| $Q_5'$ | 11.9% | 0.88 | 22 | 22 |
| $Q_4'$ | 1.6% | 0.88 | 22 | 44 |
| $Q_3'$ | 0.2% | 0.88 | 22 | 66 |
| $Q_2'$ | 0.03% | 0.88 | 22 | 88 |
| $Q_1'$ (distal) | 0.01% | 0.97 | 22 | 110 |
| $Q_{TOTAL}$ | 100% | | | |

Example 3

Example 3 also illustrates flow distribution for openings having the same diameter. However, as shown in Table 5, the openings are closer together (10 mm vs. 22 mm). As shown in Table 5 and FIG. 35B, 80.9% of fluid passing through the drainage lumen entered the drainage lumen through the proximal most opening ($Q_6$). 96.3% of fluid in the drainage lumen entered the drainage lumen through the two proximal-most openings ($Q_5$ and $Q_6$).

TABLE 5

| Position | % Flow Distribution | Diameter (mm) | Length (mm) | Cumulative Length (mm) |
|---|---|---|---|---|
| $Q_6'$ (proximal) | 80.9% | 0.88 | 0 | 0 |
| $Q_5'$ | 15.4% | 0.88 | 10 | 10 |
| $Q_4'$ | 2.9% | 0.88 | 10 | 20 |
| $Q_3'$ | 0.6% | 0.88 | 10 | 30 |
| $Q_2'$ | 0.1% | 0.88 | 10 | 40 |
| $Q_1'$ (distal) | 0.02% | 0.97 | 15 | 55 |
| $Q_{TOTAL}$ | 100% | | | |

Additional Exemplary Ureteral Catheters

As shown in FIG. 1, a urine collection assembly 100 including ureteral catheters 112, 114 configured to be positioned within the urinary tract of a patient is illustrated. For example, distal ends 120, 121 of the ureteral catheters 112, 114 can be configured to be deployed in the patient's ureters 2, 4 and, in particular, in a renal pelvis 20, 21 area of the kidneys 6, 8.

In some examples, the urine collection assembly 100 can comprise two separate ureteral catheters, such as a first catheter 112 disposed in or adjacent to the renal pelvis 20 of the right kidney 2 and a second catheter 114 disposed in or adjacent to the renal pelvis 21 of the left kidney 4. The catheters 112, 114 can be separate for their entire lengths, or can be held in proximity to one another by a clip, ring, clamp, or other type of connection mechanism (e.g., connector 150) to facilitate placement or removal of the catheters 112, 114. In some examples, catheters 112, 114 can merge or be connected together to form a single drainage lumen. In other examples, the catheters 112, 114 can be inserted through or enclosed within another catheter, tube, or sheath along portions or segments thereof to facilitate insertion and retraction of the catheters 112, 114 from the body. For example, a bladder catheter 116 can be inserted over and/or along the same guidewire as the ureteral catheters 112, 114, thereby causing the ureteral catheters 112, 114 to extend from the distal end of the bladder catheter 116.

Figure 2A:
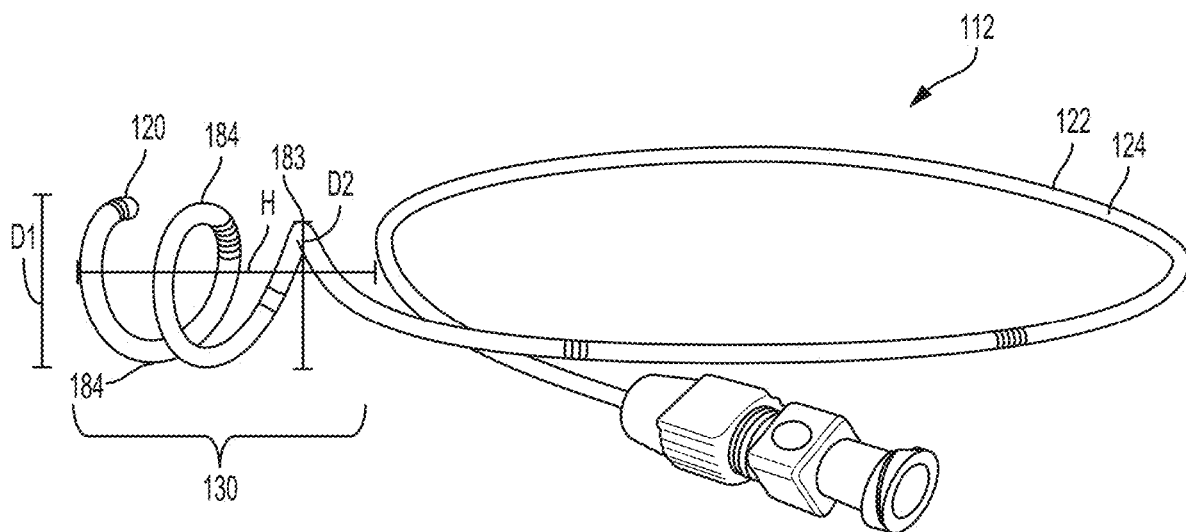
FIG. 2A is a perspective view of an exemplary ureteral catheter according to an example of the disclosure.
Figure 2B:
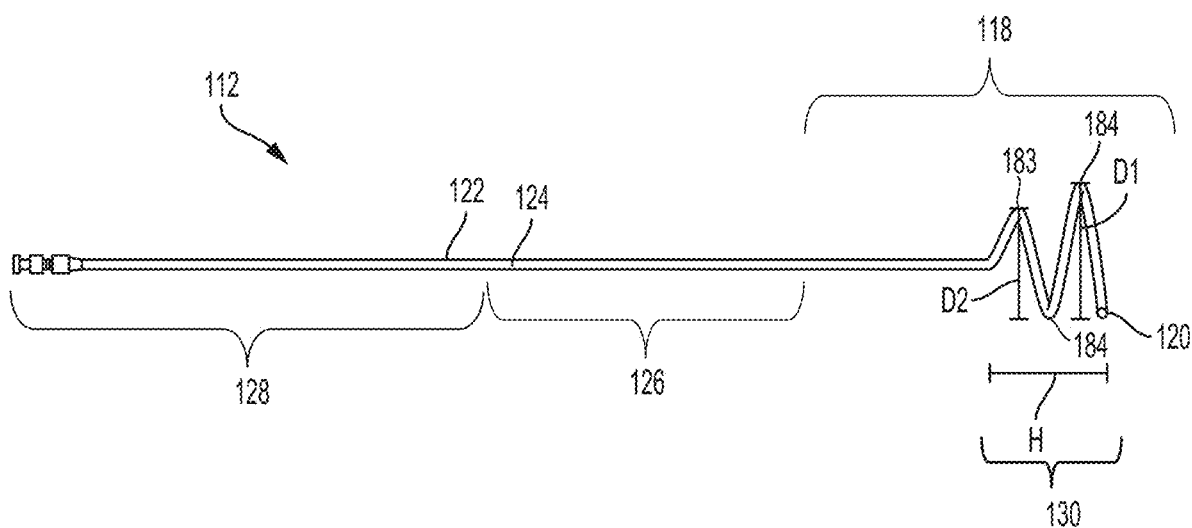
FIG. 2B is a front view of the ureteral catheter of FIG. 2A.

With reference to FIGS. 1, 2A, and 2B, an exemplary ureteral catheter 112 can comprise at least one elongated body or tube 122, the interior of which defines or comprises one or more drainage channel(s) or lumen(s), such as drainage lumen 124. The tube 122 size can range from about 1 Fr to about 9 Fr (French catheter scale). In some examples, the tube 122 can have an external diameter ranging from about 0.33 to about 3 mm, and an internal diameter ranging from about 0.165 to about 2.39 mm. In one example, the tube 122 is 6 Fr and has an outer diameter of 2.0±0.1 mm. The length of the tube 122 can range from about 30 cm to about 120 cm depending on the age (e.g., pediatric or adult) and gender of the patient.

The tube 122 can be formed from a flexible and/or deformable material to facilitate advancing and/or positioning the tube 122 in the bladder 10 and ureters 6, 8 (shown in FIG. 1). The catheter material should be flexible and soft enough to avoid or reduce irritation of the renal pelvis and ureter, but should be rigid enough that the tube 122 does not collapse when the renal pelvis or other portions of the urinary tract exert pressure on the exterior of the tube 122, or when the renal pelvis and/or ureter are drawn against the tube 122 during inducement of negative pressure. For example, the tube 122 can be formed from materials including biocompatible polymers, polyvinyl chloride, polytetrafluoroethylene (PTFE) such as Teflon®, silicone coated latex, or silicone. In one example, the tube 122 is formed from a thermoplastic polyurethane. At least a portion or all of the catheter 112, such as the tube 122, can be coated with a hydrophilic coating to facilitate insertion and/or removal, and/or to enhance comfort. In some examples, the coating is a hydrophobic and/or lubricious coating. For example, suitable coatings can comprise ComfortCoat® hydrophilic coating which is available from Koninklijke DSM N.V. or hydrophilic coatings comprising polyelectrolyte(s) such as are disclosed in U.S. Pat. No. 8,512,795, which is incorporated herein by reference.

In some examples, the tube 122 can comprise: a distal portion 118 (e.g., a portion of the tube 122 configured to be positioned in the ureter 6, 8 and renal pelvis 20, 21); a middle portion 126 (e.g., a portion of the tube 122 configured to extend from the distal portion through the ureteral openings 16 into the patient's bladder 10 and urethra 12); and a proximal portion 128 (e.g., a portion of the tube 122 extending from the urethra 12 to an external fluid collection container and/or pump assembly). In one preferred example, the combined length of the proximal portion 128 and the middle portion 126 of the tube 122 is about 54±2 cm. In some examples, the tube 122 terminates in another indwelling catheter and/or drainage lumen, such as in a drainage lumen of the bladder catheter 116. In that case, fluid drains from the proximal end of the ureteral catheter 112, 114 and is directed from the body through the additional indwelling catheter and/or drainage lumen.

Additional Exemplary Ureteral Retention Portions:

With continued reference to FIGS. 1, 2A, and 2B, the distal portion 118 of the ureteral catheter 112 comprises a retention portion 130 for maintaining the distal end 120 of the catheter 112 at a desired fluid collection position proximate to or within the renal pelvis 20, 21 of the kidney 2, 4. In some examples, the retention portion 130 is configured to be flexible and bendable to permit positioning of the retention portion 130 in the ureter and/or renal pelvis. The retention portion 130 is desirably sufficiently bendable to absorb forces exerted on the catheter 112 and to prevent such forces from being translated to the ureters. For example, if the retention portion 130 is pulled in the proximal direction P (shown in FIG. 3A) toward the patient's bladder, the retention portion 130 can be sufficiently flexible to begin to unwind or be straightened so that it can be drawn through the ureter. Similarly, when the retention portion 130 can be reinserted into the renal pelvis or other suitable region within the ureter, it can be biased to return to its deployed configuration.

Figure 4A:
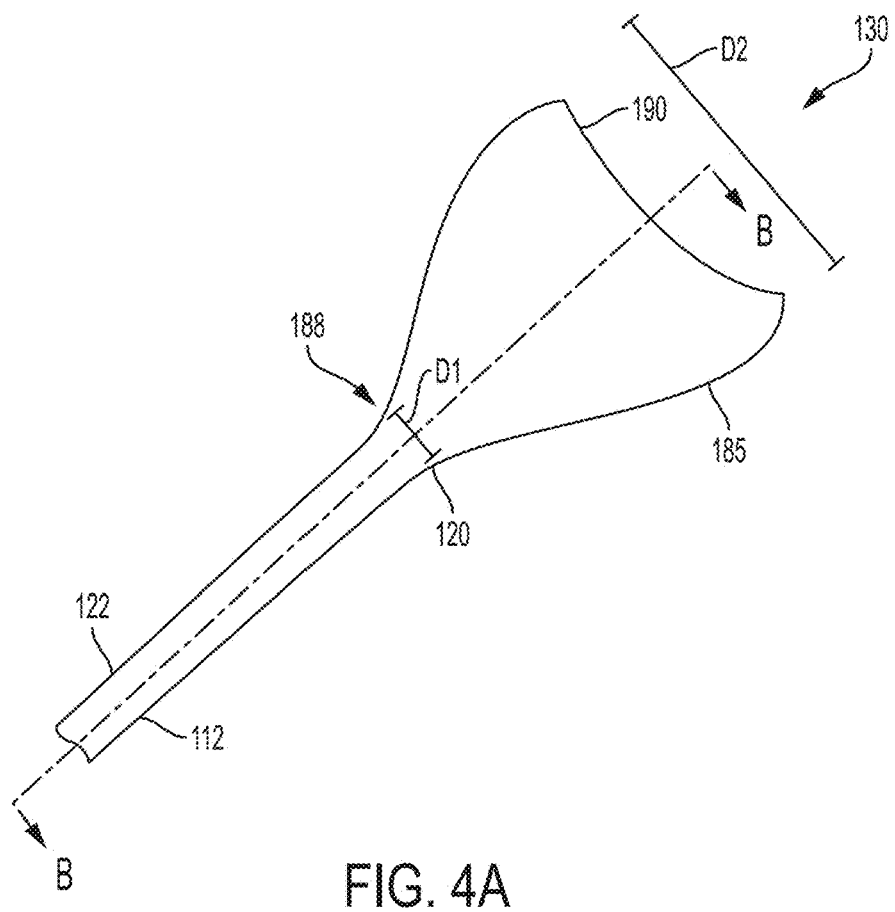
FIG. 4A is a schematic drawing of another example of a retention portion for a ureteral catheter according to an example of the present invention.
Figure 4B:
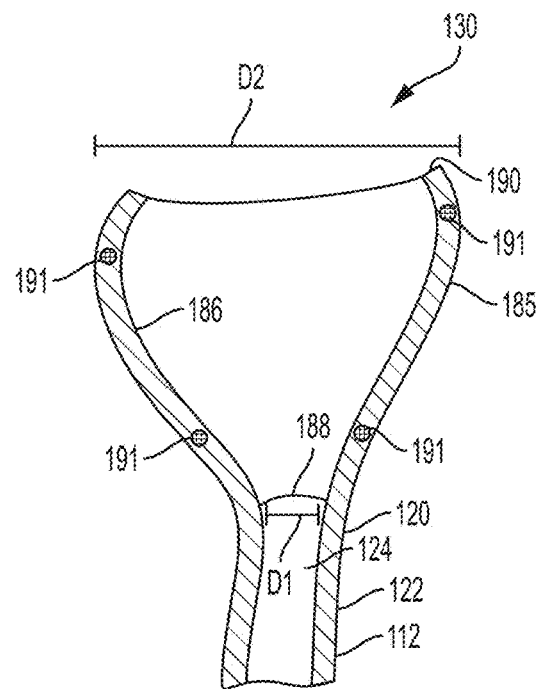
FIG. 4B is a schematic drawing of a cross-sectional view of a portion of the retention portion of FIG. 4A, taken along lines B-B of FIG. 4A.

In some examples, the retention portion 130 is integral with the tube 122. In that case, the retention portion 130 can be formed by imparting a bend or curl to the catheter body 122 that is sized and shaped to retain the catheter at a desired fluid collection location. Suitable bends or coils can include a pigtail coil, corkscrew coil, and/or helical coil. For example, the retention portion 130 can comprise one or more radially and longitudinally extending helical coils configured to contact and passively retain the catheter 112 within the ureter 6, 8 proximate to or within the renal pelvis 20, 21. In other examples, the retention portion 130 is formed from a radially flared or tapered portion of the catheter body 122. For example, the retention portion 130 can further comprise a fluid collecting portion, as shown in FIGS. 4A and 4B, such as a tapered or funnel-shaped inner surface 186. In other examples, the retention portion 130 can comprise a separate element connected to and extending from the catheter body or tube 122.

The retention portion 130 can further comprise one or more perforated sections, such as drainage holes or ports 132 (shown in FIGS. 3A-3E). A drainage port can be located, for example, at the open distal end 120, 121 of the tube 122. In other examples, perforated sections and/or drainage ports 132 are disposed along the sidewall of the distal portion 118 of the catheter tube 122. The drainage ports or holes can be used for assisting in fluid collection. In other examples, the retention portion 130 is solely a retention structure and fluid collection and/or imparting negative pressure is provided by structures at other locations on the catheter tube 122.

Referring now to FIGS. 2A, 2B, and 3A-3E, exemplary retention portions 130 comprising a plurality of helical coils, such as one or more full coils 184 and one or more half or partial coils 183, are illustrated. The retention portion 130 is capable of moving between a contracted position and the deployed position with the plurality of helical coils. For example, a substantially straight guidewire can be inserted through the retention portion 130 to maintain the retention portion 130 in a substantially straight contracted position. When the guidewire is removed, the retention portion 130 can transition to its coiled configuration. In some examples, the coils 183, 184 extend radially and longitudinally from the distal portion 118 of the tube 122. With specific reference to FIGS. 2A and 2B, in a preferred exemplary embodiment, the retention portion 130 comprises two full coils 184 and one half coil 183. The outer diameter of the full coils 184, shown by line D1, can be about 18±2 mm. The half coil 183 diameter D2 can be about 14 mm. The coiled retention portion 130 has a height H of about 16±2 mm. The retention portion 130 can further comprise the one or more drainage holes 132 (shown in FIGS. 3A-3E) configured to draw fluid into an interior of the catheter tube 122. In some examples, the retention portion 130 can comprise six drainage holes, plus an additional hole at the distal tip 120 of the retention portion. The diameter of each of the drainage holes 132 (shown in FIGS. 3A-3E) can range from about 0.7 mm to 0.9 mm and, preferably, is about 0.83±0.01 mm. The distance between adjacent drainage holes 132, specifically the linear distance between drainage holes 132 when the coils are straightened, can be about 22.5±2.5 mm.

Figure 3A:
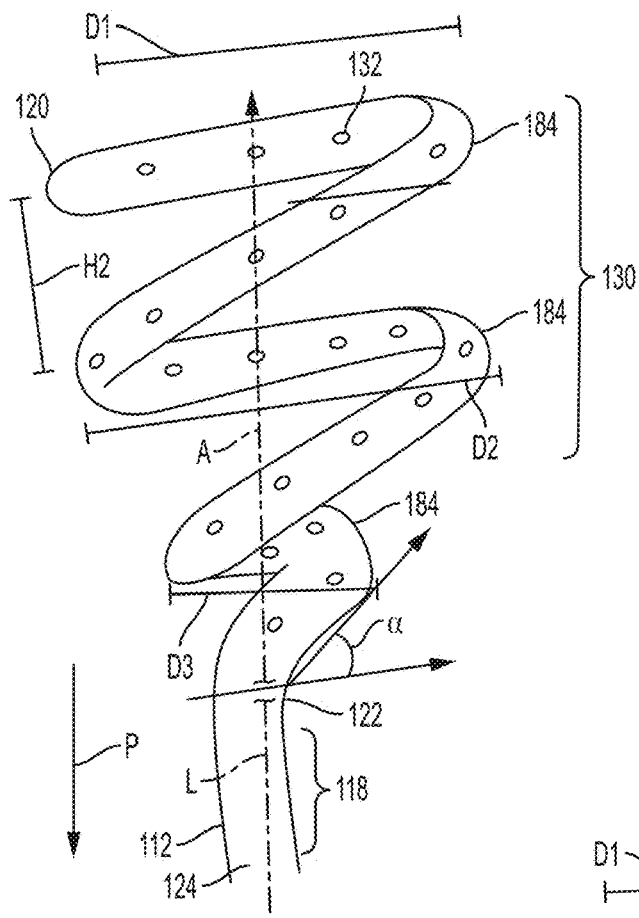
FIG. 3A is a schematic drawing of an example of a retention portion for a ureteral catheter according to an example of the present invention.
Figure 3B:
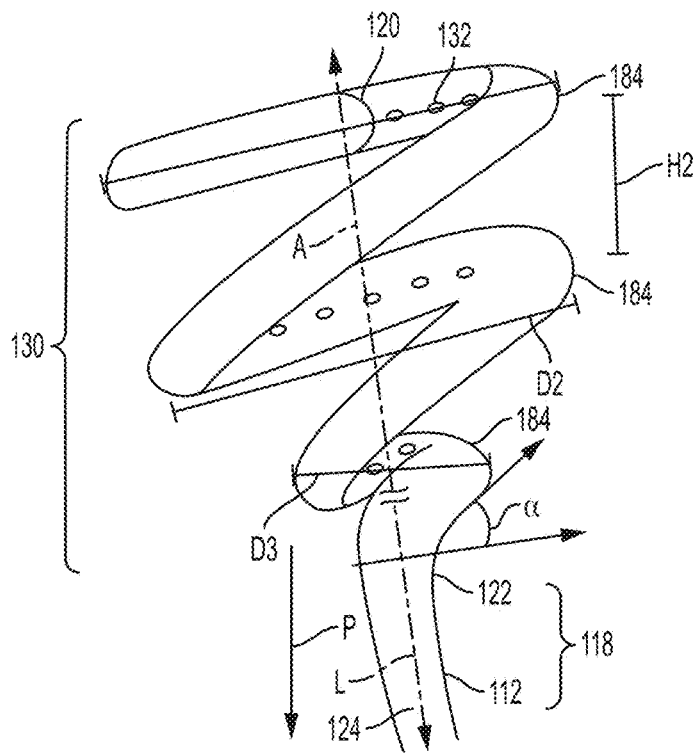
FIG. 3B is a schematic drawing of another example of a retention portion for a ureteral catheter according to an example of the present invention.
Figure 3E:
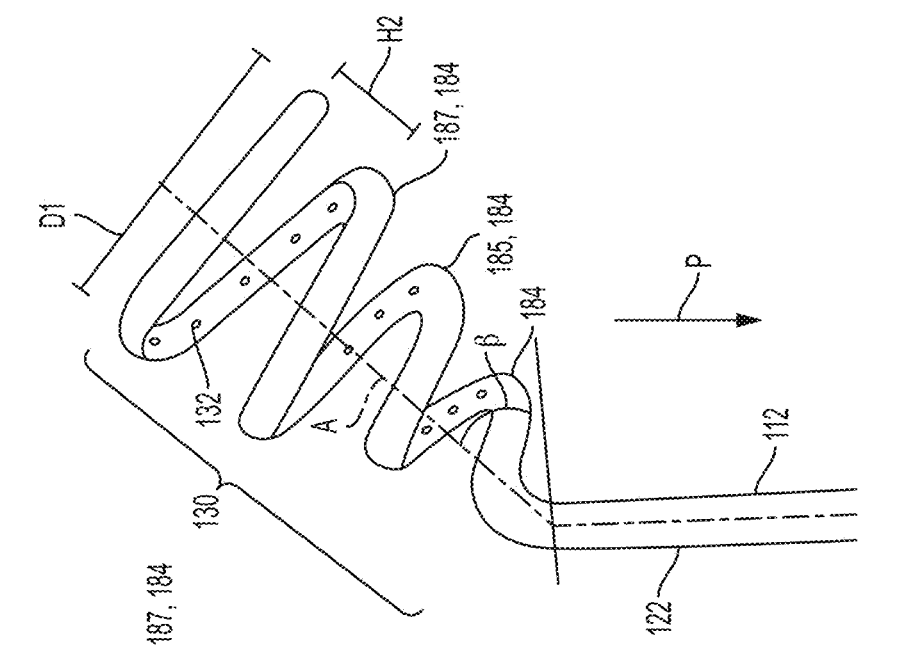
FIG. 3E is a schematic drawing of another example of a retention portion for a ureteral catheter according to an example of the present invention.
Figure 3D:
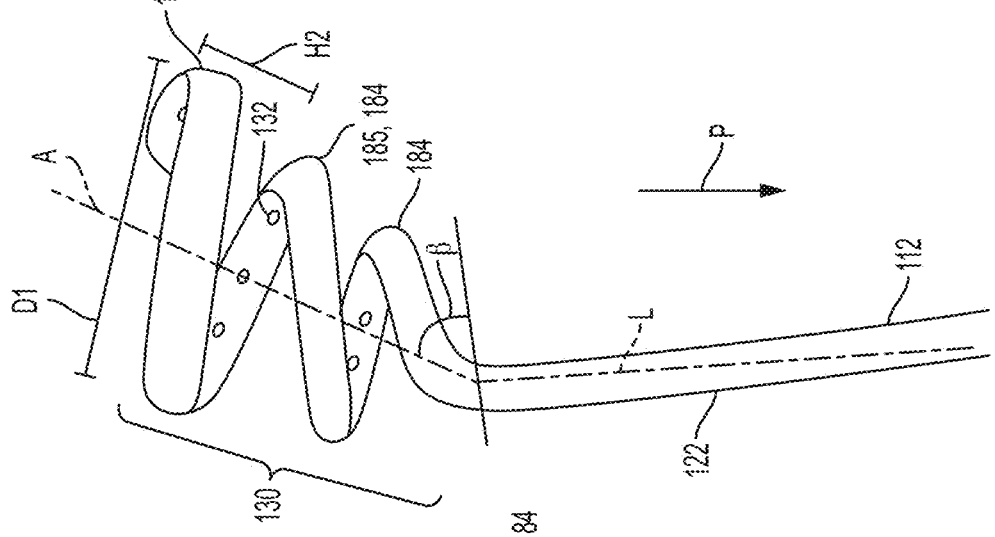
FIG. 3D is a schematic drawing of another example of a retention portion for a ureteral catheter according to an example of the present invention.
Figure 3C:
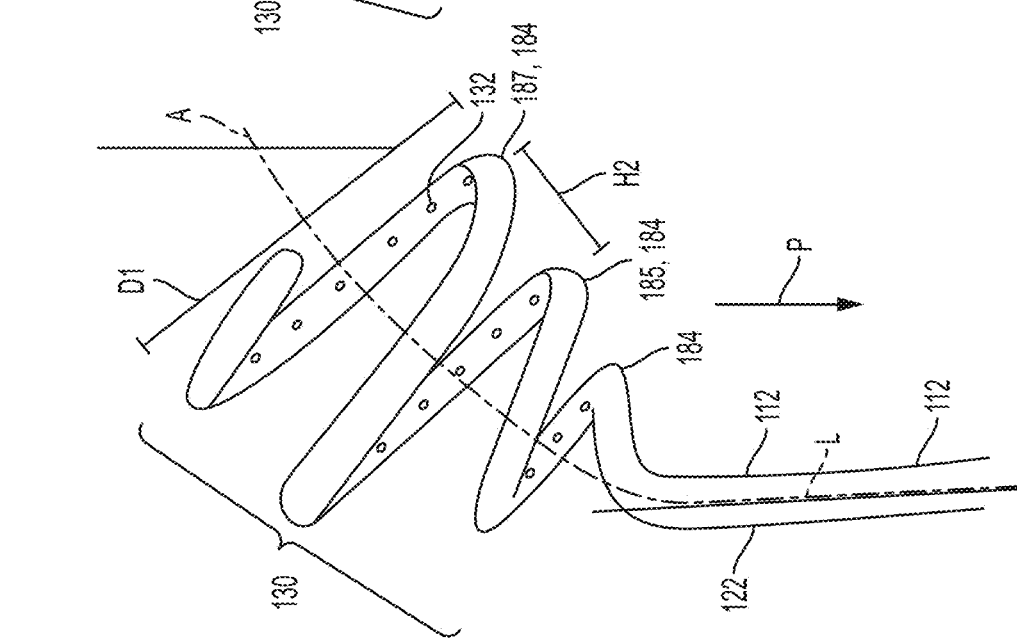
FIG. 3C is a schematic drawing of another example of a retention portion for a ureteral catheter according to an example of the present invention.

As shown in FIGS. 3A-3E, in another exemplary embodiment, the distal portion 118 of the drainage lumen proximal to the retention portion 130 defines a straight or curvilinear central axis L. In some examples, at least a half or first coil 183 and a full or second coil 184 of the retention portion 130 extend about an axis A of the retention portion 130. The first coil 183 initiates or begins at a point where the tube 122 is bent at an angle α ranging from about 15 degrees to about 75 degrees from the central axis L, as indicated by angle α, and preferably about 45 degrees. As shown in FIGS. 3A and 3B, prior to insertion in the body, the axis A can be coextensive with the longitudinal central axis L. In other examples, as shown in FIGS. 3C-3E, prior to insertion in the body, the axis A extends from and is curved or angled, for example at angle β, relative to the central longitudinal axis L.

In some examples, multiple coils 184 can have the same inner and/or outer diameter D and height H2. In that case, the outer diameter D1 of the coils 184 may range between 10 mm and 30 mm. The height H2 between coils 184 may be about 3 mm to 10 mm.

In other examples, the retention portion 130 is configured to be inserted in the tapered portion of the renal pelvis. For example, the outer diameter D1 of the coils 184 can increase toward the distal end 120 of the tube 122, resulting in a helical structure having a tapered or partially tapered configuration. For example, the distal or maximum outer diameter D1 of the tapered helical portion ranges from about 10 mm to about 30 mm, which corresponds to the dimensions of the renal pelvis. The height H2 of the retention portion 130 ranges from about 10 mm to about 30 mm.

In some examples, the outer diameter D1 and/or height H2 of the coils 184 can vary in a regular or irregular fashion. For example, the outer diameter D1 of coils or height H2 between coils can increase or decrease by a regular amount (e.g., about 10% to about 25% between adjacent coils 184). For example, for a retention portion 130 having three coils (as shown, for example, in FIGS. 3A and 3B) an outer diameter D3 of a proximal-most coil or first coil 183 can be about 6 mm to 18 mm, an outer diameter D2 of a middle coil or second coil 185 can be about 8 mm to about 24 mm, and an outer diameter D1 of a distal-most or third coil 187 can be between about 10 mm and about 30 mm.

The retention portion 130 can further comprise the drainage ports 132 or holes disposed on or through the sidewall of the catheter tube 122 on or adjacent to the retention portion 130 to permit urine waste to flow from the outside of the catheter tube 122 to the inside of the catheter tube 122. The position and size of the drainage ports 132 can vary depending upon the desired flow rate and configuration of the retention portion. The diameter of the drainage ports 132 can range from about 0.005 mm to about 1.0 mm. The spacing between the drainage ports 132 can range from about 0.1 mm to about 255 mm. The drainage ports 132 can be spaced in any arrangement, for example, linear or offset. In some examples, the drainage ports 132 can be non-circular, and can have a surface area of about 0.002 mm$^2$ to 0.79 mm$^2$ or more.

In some examples, as shown in FIG. 3A, the drainage ports 132 are located around the entire periphery of the sidewall of the catheter tube 122 to increase an amount of fluid that can be drawn into the drainage lumen 124 (shown in FIGS. 1, 2A, and 2B). In other examples, as shown in FIGS. 3B-3E, the drainage ports 132 can be disposed essentially only or only on the radially inwardly facing side of the coils 184 to prevent occlusion or blockage of the drainage ports 132, and the outwardly facing side of the coils may be essentially free of drainage ports 132 or free of drainage ports 132. For example, when negative pressure is induced in the ureter and/or renal pelvis, mucosal tissue of the ureter and/or kidney may be drawn against the retention portion 130 and may occlude some drainage ports 132 on the outer periphery of the retention portion 130. Drainage ports 132 located on the radially inward side of the retention structure would not be appreciably occluded when such tissues contact the outer periphery of the retention portion 130. Further, risk of injury to the tissues from pinching or contact with the drainage ports 132 can be reduced or ameliorated.

With reference to FIGS. 3C and 3D, other examples of ureteral catheters 112 having a retention portion 130 comprising a plurality of coils are illustrated. As shown in FIG. 3C, the retention portion 130 comprises three coils 184 extending about the axis A. The axis A is a curved arc extending from the central longitudinal axis L of the portion of the drainage lumen 181 proximal to the retention portion 130. The curvature imparted to the retention portion 130 can be selected to correspond to the curvature of the renal pelvis, which comprises a cornucopia-shaped cavity.

As shown in FIG. 3D, in another exemplary embodiment, the retention portion 130 can comprise two coils 184 extending about an angled axis A. The angled axis A extends at an angle from a central longitudinal axis L, and is angled, as shown by angle β, relative to an axis generally perpendicular to the central axis L of the portion of the drainage lumen. The angle β can range from about 15 to about 75 degrees (e.g., about 105 to about 165 degrees relative to the central longitudinal axis L of the drainage lumen portion of the catheter 112).

FIG. 3E shows another example of a ureteral catheter 112. The retention portion comprises three helical coils 184 extending about an axis A. The axis A is angled, as shown by angle β, relative to the horizontal. As in the previously-described examples, the angle β can range from about 15 to about 75 degrees (e.g., about 105 to about 165 degrees relative to the central longitudinal axis L of the drainage lumen portion of the catheter 112).

With reference to FIGS. 4A and 4B, in another example, a retention portion 130 of a ureteral catheter 112 comprises a catheter tube 122 having a widened and/or tapered distal end portion which, in some examples, is configured to be positioned in the patient's renal pelvis and/or kidney. For example, the retention portion 130 can be a funnel-shaped structure comprising an outer surface 185 configured to be positioned against the ureter and/or kidney wall and comprising an inner surface 186 configured to direct fluid toward a drainage lumen 124 of the catheter 112. The retention portion 130 can comprise a proximal end 188 adjacent to the distal end of the drainage lumen 124 and having a first diameter D1 and a distal end 190 having a second diameter D2 that is greater than the first diameter D1 when the retention portion 130 is in its deployed position. In some examples, the retention portion 130 is transitionable from a collapsed or compressed position to the deployed position. For example, the retention portion 130 can be biased radially outward such that when the retention portion 130 is advanced to its fluid collecting position, the retention portion 130 (e.g., the funnel portion) expands radially outward to the deployed state.

The retention portion 130 of the ureteral catheter 112 can be made from a variety of suitable materials that are capable of transitioning from the collapsed state to the deployed state. In one example, the retention portion 130 comprises a framework of tines or elongated members formed from a temperature sensitive shape memory material, such as nitinol. In some examples, the nitinol frame can be covered with a suitable waterproof material such as silicone to form a tapered portion or funnel. In that case, fluid is permitted to flow down the inner surface 186 of the retention portion 130 and into the drainage lumen 124. In other examples, the retention portion 130 is formed from various rigid or partially rigid sheets or materials bended or molded to form a funnel-shaped retention portion as illustrated in FIGS. 4A and 4B.

In some examples, the retention portion of the ureteral catheter 112 can include one or more mechanical stimulation devices 191 for providing stimulation to nerves and muscle fibers in adjacent tissues of the ureter(s) and renal pelvis. For example, the mechanical stimulation devices 191 can include linear or annular actuators embedded in or mounted adjacent to portions of the sidewall of the catheter tube 122 and configured to emit low levels of vibration. In some examples, mechanical stimulation can be provided to portions of the ureters and/or renal pelvis to supplement or modify therapeutic effects obtained by application of negative pressure. While not intending to be bound by theory, it is believed that such stimulation affects adjacent tissues by, for example, stimulating nerves and/or actuating peristaltic muscles associated with the ureter(s) and/or renal pelvis. Stimulation of nerves and activation of muscles may produce changes in pressure gradients or pressure levels in surrounding tissues and organs which may contribute to or, in some cases, enhance therapeutic benefits of negative pressure therapy.

Figure 5A:
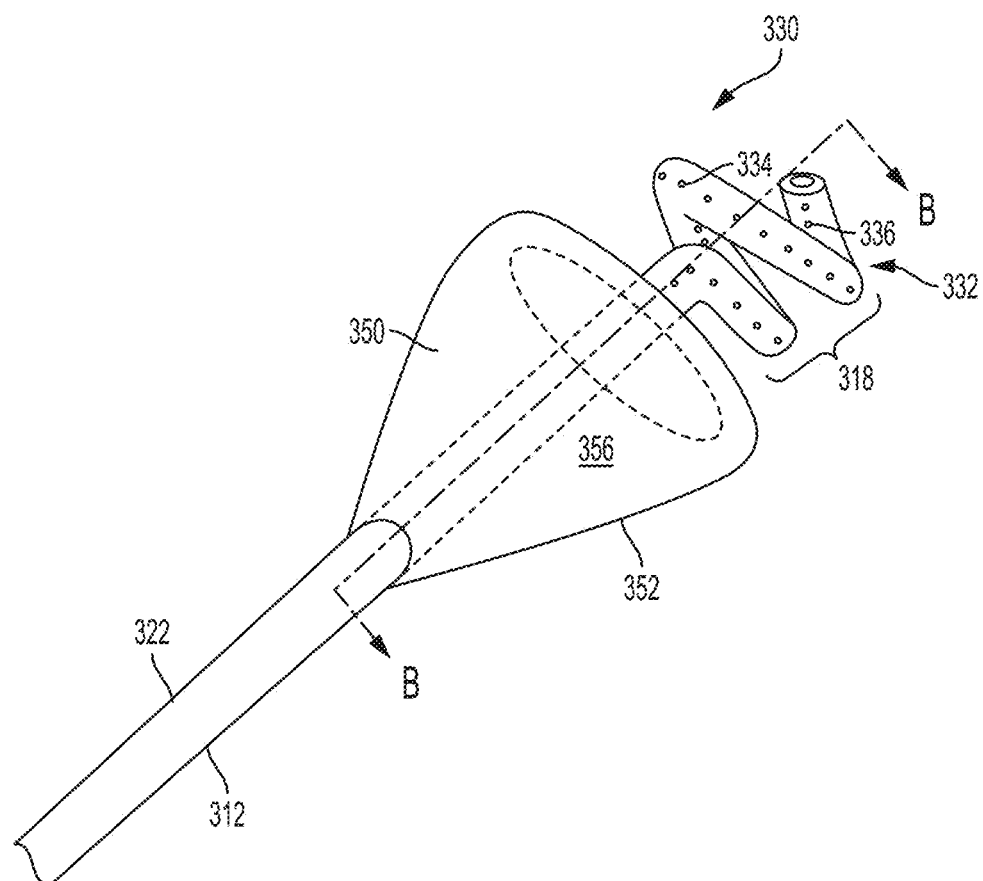
FIG. 5A is a schematic drawing of another example of a retention portion for a ureteral catheter according to an example of the present invention.
Figure 5B:
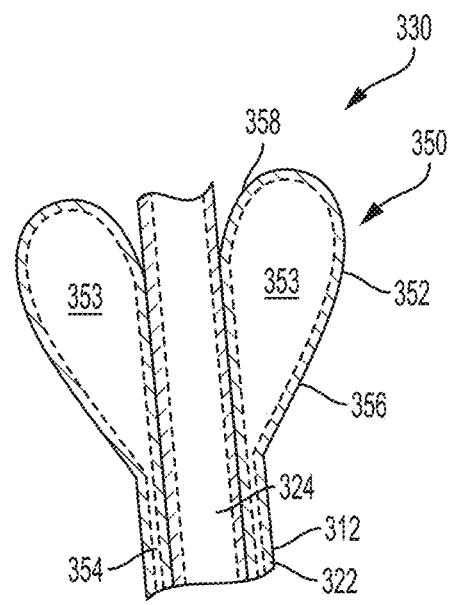
FIG. 5B is a schematic drawing of a portion of a cross-sectional view of the retention portion of FIG. 5A, taken along lines B-B of FIG. 5A.

With reference to FIGS. 5A and 5B, according to another example, a retention portion 330 of a ureteral catheter 312 comprises a catheter tube 322 having a distal portion 318 formed in a helical structure 332 and an inflatable element or balloon 350 positioned proximal to the helical structure 332 to provide an additional degree of retention in the renal pelvis and/or fluid collection location. A balloon 350 can be inflated to pressure sufficient to retain the balloon in the renal pelvis or ureter, but low enough to avoid distending or damaging these structures. Suitable inflation pressures are known to those skilled in the art and are readily discernible by trial and error. As in previously-described examples, the helical structure 332 can be imparted by bending the catheter tube 322 to form one or more coils 334. The coils 334 can have a constant or variable diameter and height as described above. The catheter tube 322 further comprises a plurality of drainage ports 336 disposed on the sidewall of the catheter tube 322 to allow urine to be drawn into the drainage lumen 324 of the catheter tube 322 and to be directed from the body through the drainage lumen 324, for example on the inwardly facing and/or outwardly facing sides of the coil 334.

As shown in FIG. 5B, the inflatable element or balloon 350 can comprise an annular balloon-like structure having, for example, a generally heart-shaped cross section and comprising a surface or cover 352 defining a cavity 353. The cavity 353 is in fluid communication with an inflation lumen 354 extending parallel to the drainage lumen 324 defined by the catheter tube 322. The balloon 350 can be configured to be inserted in the tapered portion of the renal pelvis and inflated such that an outer surface 356 thereof contacts and rests against an inner surface of the ureter and/or renal pelvis. The inflatable element or balloon 350 can comprise a tapered inner surface 358 extending longitudinally and radially inward toward the catheter tube 322. The inner surface 358 can be configured to direct urine toward the catheter tube 322 to be drawn into the drainage lumen 324. The inner surface 358 can also be positioned to prevent fluid from pooling in the ureter, such as around the periphery of the inflatable element or balloon 350. The inflatable retention portion or balloon 350 is desirably sized to fit within the renal pelvis and can have a diameter ranging from about 10 mm to about 30 mm.

Figure 6:
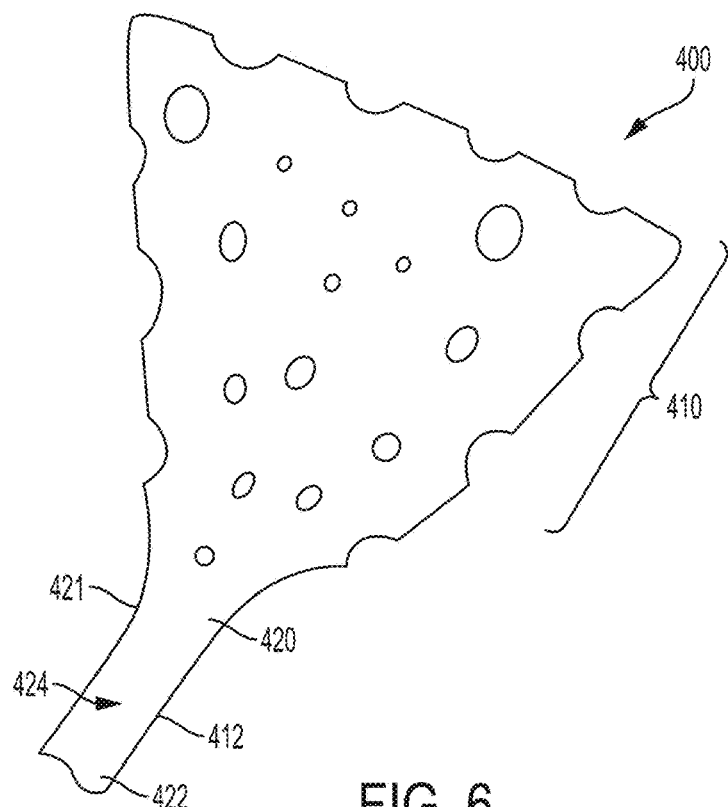
FIG. 6 is a schematic drawing of another example of a retention portion for a ureteral catheter according to an example of the present invention.
Figure 7:
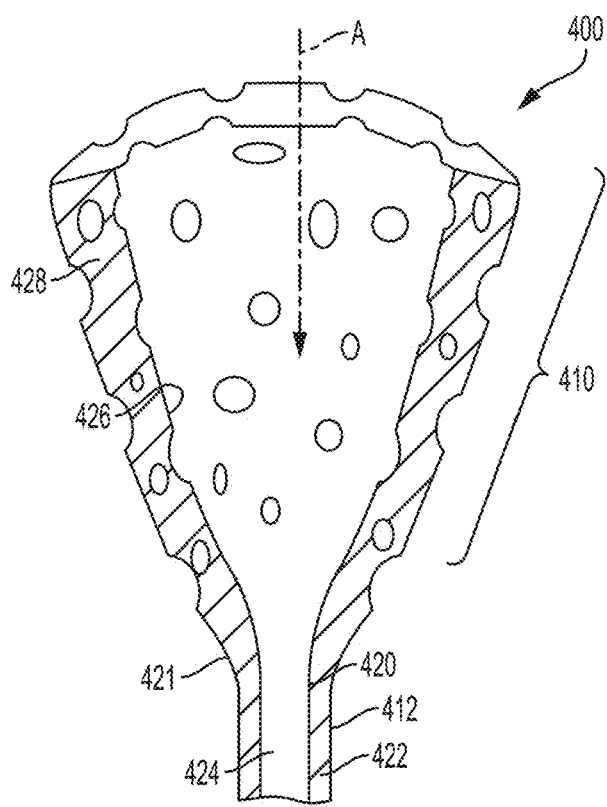
FIG. 7 is a schematic drawing of a cross section of another example of a retention portion for a ureteral catheter according to an example of the present invention.

With reference to FIGS. 6 and 7, in some examples, an assembly 400 including a ureteral catheter 412 comprising a retention portion 410 is illustrated. The retention portion 410 is formed from a porous and/or sponge-like material that is attached to a distal end 421 of a catheter tube 422. The porous material can be configured to channel and/or absorb urine and direct the urine toward a drainage lumen 424 of the catheter tube 422. As shown in FIG. 7, the retention portion 410 can be a porous wedge shaped-structure configured for insertion and retention in the patient's renal pelvis. The porous material comprises a plurality of holes and/or channels. Fluid can be drawn through the channels and holes, for example, by gravity or upon inducement of negative pressure through the catheter 412. For example, fluid can enter the wedge-shaped retention portion 410 through the holes and/or channels and is drawn toward a distal opening 420 of the drainage lumen 424, for example, by capillary action, peristalsis, or as a result of the inducement of negative pressure in the holes and/or channels. In other examples, as shown in FIG. 7, the retention portion 410 comprises a hollow, funnel structure formed from the porous sponge-like material. As shown by arrow A, fluid is directed down an inner surface 426 of the funnel structure into the drainage lumen 424 defined by the catheter tube 422. Also, fluid can enter the funnel structure of the retention portion 410 through holes and channels in the porous sponge-like material of a sidewall 428. For example, suitable porous materials can include open-celled polyurethane foams, such as polyurethane ether. Suitable porous materials can also include laminates of woven or non-woven layers comprising, for example, polyurethane, silicone, polyvinyl alcohol, cotton, or polyester, with or without antimicrobial additives such as silver, and with or without additives for modifying material properties such as hydrogels, hydrocolloids, acrylic, or silicone.

Figure 8:
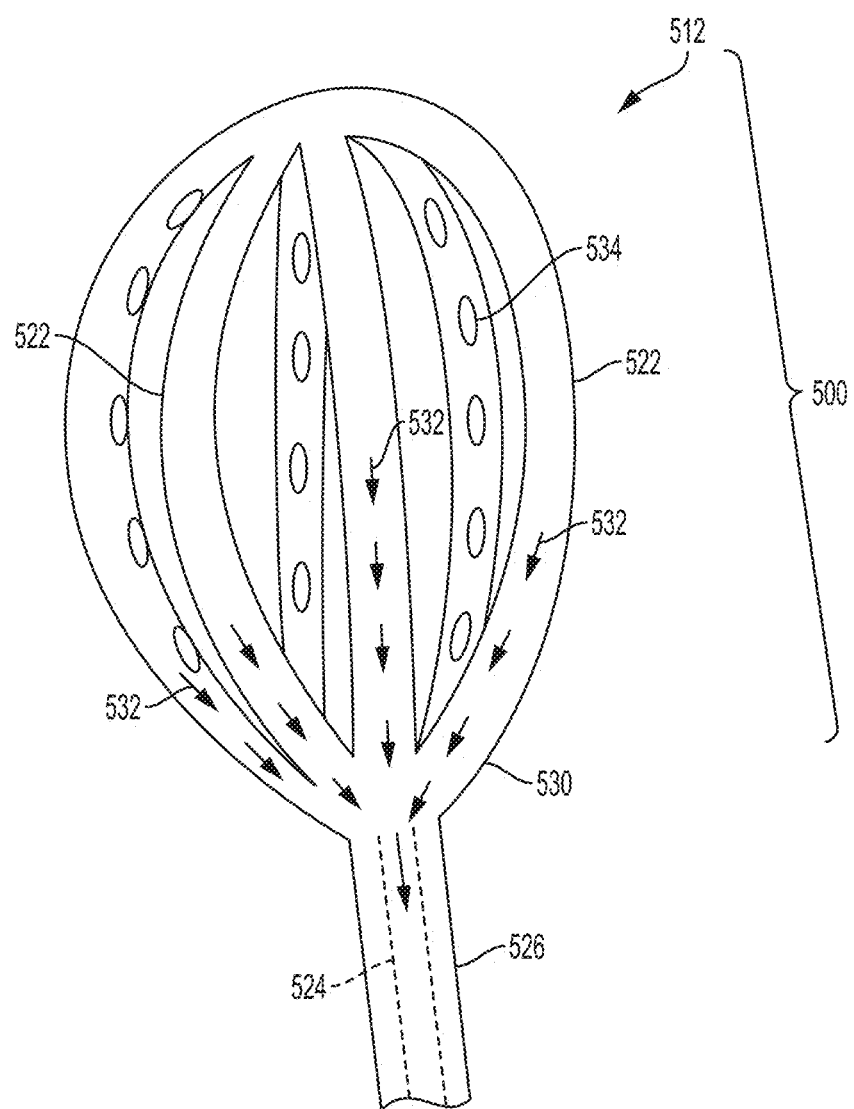
FIG. 8 is a schematic drawing of another example of a retention portion for a ureteral catheter according to an example of the present invention.

With reference to FIG. 8, according to another example, a retention portion 500 of a ureteral catheter 512 comprises an expandable cage 530. The expandable cage 530 comprises one or more longitudinally and radially extending hollow tubes 522. For example, the tubes 522 can be formed from an elastic, shape memory material such as nitinol. The cage 530 is configured to transition from a contracted state, for insertion through the patient's urinary tract, to a deployed state for positioning in the patient's ureters and/or kidney. The hollow tubes 522 comprise a plurality of drainage ports 534 which can be positioned on the tubes, for example, on radially inward facing sides thereof. The ports 534 are configured to permit fluid to flow or be drawn through the ports 534 and into the respective tubes 522. The fluid drains through the hollow tubes 522 into a drainage lumen 524 defined by a catheter body 526 of the ureteral catheter 512. For example, fluid can flow along the path indicated by the arrows 532 in FIG. 8. In some examples, when negative pressure is induced in the renal pelvis, kidneys, and/or ureters, portions of the ureter wall and/or renal pelvis may be drawn against the outward facing surfaces of the hollow tubes 522. The drainage ports 534 are positioned and configured so as not to be appreciably occluded by ureteral structures upon application of negative pressure to the ureters and/or kidney.

Figure 9A:
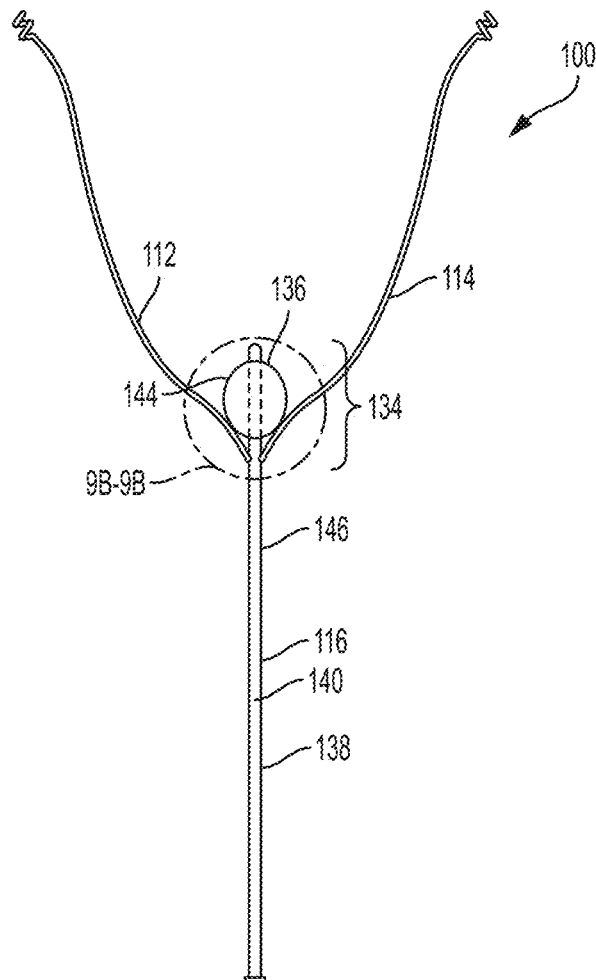
FIG. 9A is a schematic drawing of another example of a urine collection assembly according to an example of the present invention.
Figure 11A:
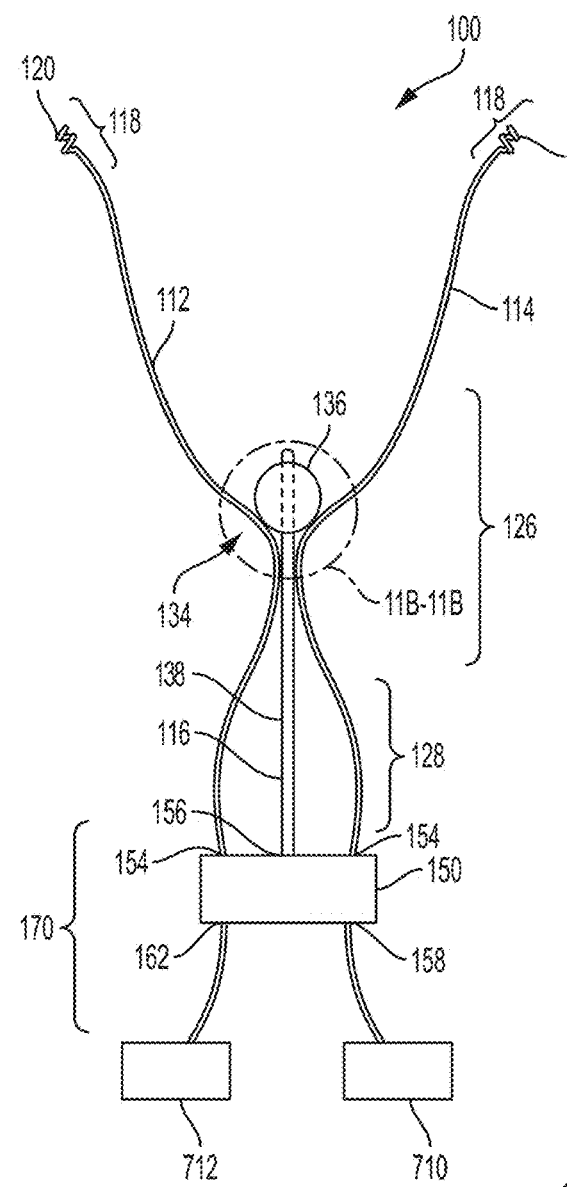
FIG. 11A is a schematic drawing of a urine collection assembly according to an example of the present invention.

Exemplary Urine Collection Assemblies:

Referring now to FIGS. 1, 9A, and 11A, the urine collection assembly 100 further comprises a bladder catheter 116. The distal ends 120, 121 of the ureteral catheters 112, 114 can be connected to the bladder catheter 116 to provide a single drainage lumen for urine, or the ureteral catheter(s) can drain via separate tube(s) from the bladder catheter 116.

Exemplary Bladder Catheter

The bladder catheter 116 comprises a deployable seal and/or anchor 136 for anchoring, retaining, and/or providing passive fixation for indwelling portions of the urine collection assembly 100 and, in some examples, to prevent premature and/or untended removal of assembly components during use. The anchor 136 is configured to be located adjacent to the lower wall of the patient's bladder 10 (shown in FIG. 1) to prevent patient motion and/or forces applied to indwelling catheters 112, 114, 116 from translating to the ureters. The bladder catheter 116 comprises an interior of which defines a drainage lumen 140 configured to conduct urine from the bladder 10 to an external urine collection container 712 (shown in FIG. 19). In some examples, the bladder catheter 116 size can range from about 8 Fr to about 24 Fr. In some examples, the bladder catheter 116 can have an external diameter ranging from about 2.7 to about 8 mm. In some examples, the bladder catheter 116 can have an internal diameter ranging from about 2.16 to about 6.2 mm. The bladder catheter 116 can be available in different lengths to accommodate anatomical differences for gender and/or patient size. For example, the average female urethra length is only a few inches, so the length of a tube 138 can be rather short. The average urethra length for males is longer due to the penis and can be variable. It is possible that woman can use bladder catheters 116 with longer length tubes 138 provided that the excess tubing does not increase difficulty in manipulating and/or preventing contamination of sterile portions of the catheter 116. In some examples, a sterile and indwelling portion of the bladder catheter 116 can range from about 1 inch to 3 inches (for women) to about 20 inches for men. The total length of the bladder catheter 116 including sterile and non-sterile portions can be from one to several feet.

The catheter tube 138 can comprise one or more drainage ports 142 configured to be positioned in the bladder 10 for drawing urine into the drainage lumen 140. For example, excess urine left in the patient's bladder 10 during placement of the ureteral catheters 112, 114 is expelled from the bladder 10 through the ports 142 and drainage lumen 140. In addition, any urine that is not collected by the ureteral catheters 112, 114 accumulates in the bladder 10, and can be conducted from the urinary tract through the drainage lumen 140. The drainage lumen 140 may be pressurized to a negative pressure to assist in fluid collection or may be maintained at atmospheric pressure such that fluid is collected by gravity and/or as a result of partial contraction of the bladder 10. In some examples, the ureteral catheters 112, 114 may extend from the drainage lumen 140 of the bladder catheter 116 to facilitate and/or simplify insertion and placement of the ureteral catheters 112, 114.

With specific reference to FIG. 1, the deployable seal and/or anchor 136 is disposed at or adjacent to a distal end 148 of the bladder catheter 116. The deployable anchor 136 is configured to transition between a contracted state for insertion into the bladder 10 through the urethra 12 and urethral opening 18 and a deployed state. The anchor 136 is configured to be deployed in and seated adjacent to a lower portion of the bladder 10 and/or against the urethral opening 18. For example, the anchor 136 can be positioned adjacent to the urethral opening 18 to enhance suction of a negative pressure applied to the bladder 10 or, in the absence of negative pressure, to partially, substantially, or entirely seal the bladder 10 to ensure that urine in the bladder 10 is directed through the drainage lumen 140 and to prevent leakage to the urethra 12. For a bladder catheter 116 including an 8 Fr to 24 Fr elongated tube 138, the anchor 136 can be about 12 Fr to 32 Fr (e.g., having a diameter of about 4 mm to about 10.7 mm) in the deployed state, and preferably between about 24 Fr and 30 Fr. A 24 Fr anchor has a diameter of about 8 mm. It is believed that a 24 Fr anchor 136 would be a single size suitable for all or most patients. For a catheter 116 with a 24 Fr anchor 136, a suitable length of the anchor 136 is between about 1.0 cm and 2.3 cm, and preferably about 1.9 cm (about 0.75 in).

Exemplary Bladder Anchor Structures

Figure 12A:
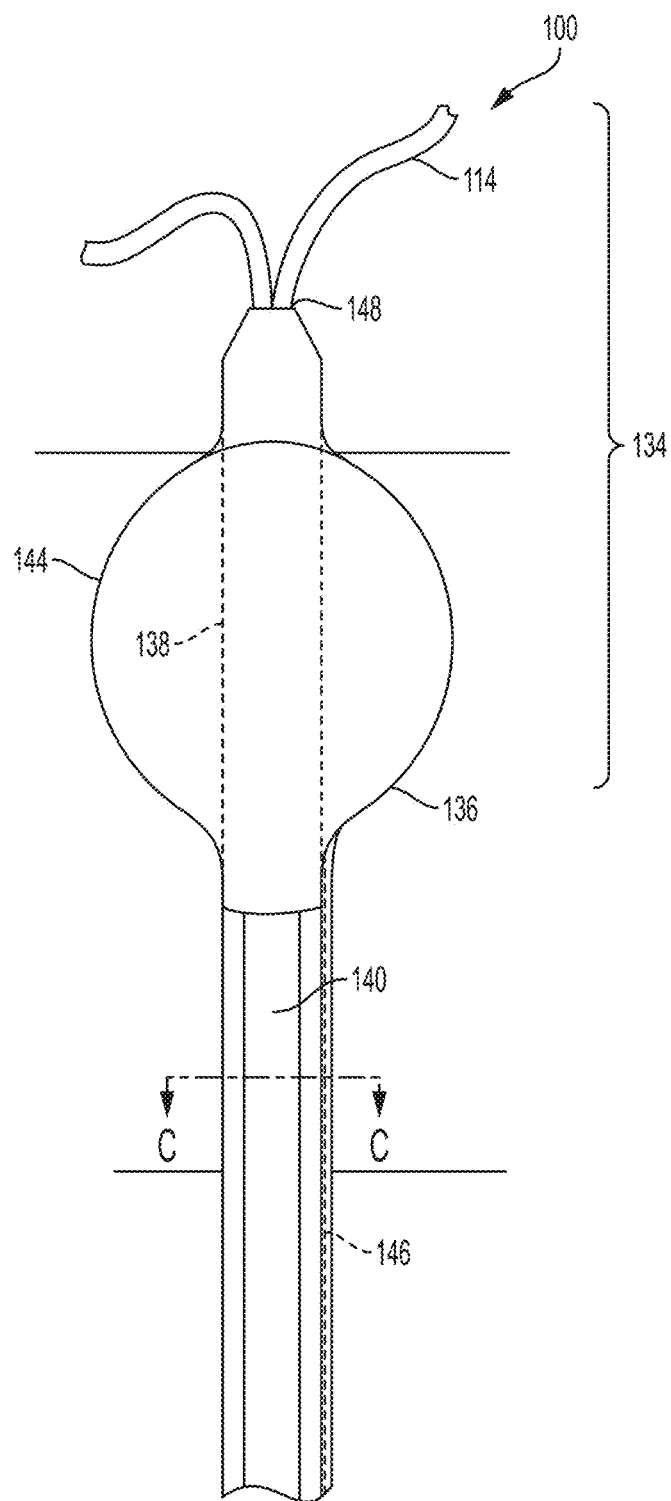
FIG. 12A is a schematic drawing of another bladder anchor portion of a urine collection assembly according to an example of the disclosure.
Figure 13:
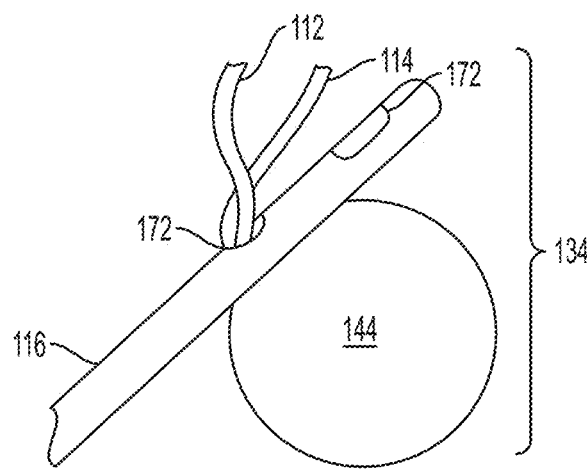
FIG. 13 is a schematic drawing of another example of a bladder anchor portion of a urine collection assembly according to an example of the present disclosure.

With specific reference to FIGS. 1, 12A, and 13, an exemplary bladder anchor 136 in the form of an expandable balloon 144 is illustrated. The expandable (e.g., inflatable) balloon 144 can be, for example, a spherical balloon of a Foley catheter. The balloon 144 can be about 1.0 cm to 2.3 cm in diameter, and preferably about 1.9 cm (0.75 in) in diameter. The balloon 144 is preferably formed from a flexible material including, for example, biocompatible polymers, polyvinyl chloride, polytetrafluoroethylene (PTFE) such as Teflon®, silicone coated latex, or silicone.

The balloon 144 is in fluid connection with an inflation lumen 146, and is inflated by introducing fluid into the balloon 144. In a deployed state, the balloon 144 can be a substantially spherical structure mounted to and extending radially outward from the catheter tube 138 of the bladder catheter 116 and comprising a central cavity or channel for the catheter tube 138 to pass through. In some examples, the catheter tube 138 extends through the cavity defined by the balloon 144, such that the open distal end 148 of the catheter tube 138 extends distally beyond the balloon 144 and toward the center of the bladder 10 (shown in FIG. 1). Excess urine collected in the bladder 10 can be drawn into the drainage lumen 140 through the distal open end 148 thereof.

Figure 14:
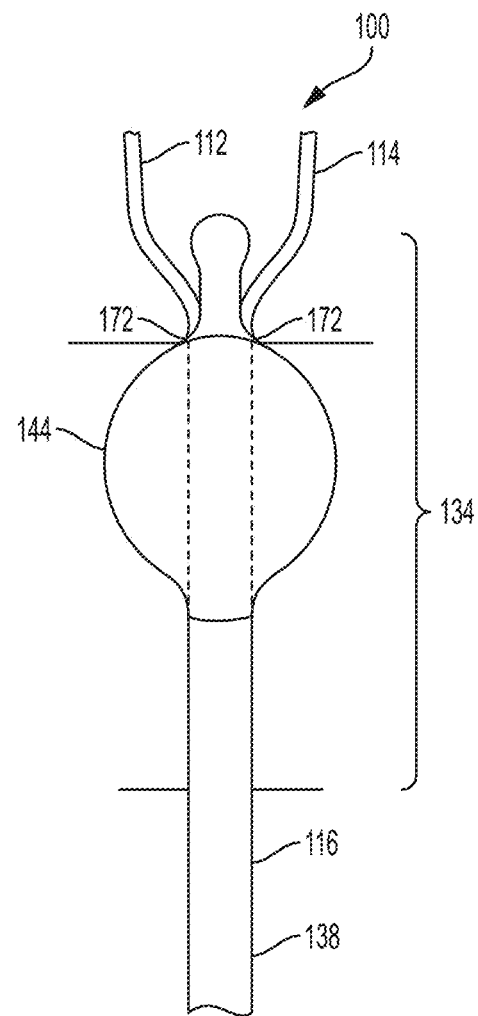
FIG. 14 is a schematic drawing of another example of a bladder anchor portion of a urine collection assembly according to an example of the present disclosure.

As shown in FIGS. 1 and 12A, in one example, the ureteral catheters 112, 114 extend from the open distal end 148 of the drainage lumen 140. In another example, as shown in FIG. 14, the ureteral catheters 112, 114 extend through ports 172 or openings disposed on a sidewall of the catheter tube 138 at a position distal to the balloon 144. The ports 172 can be circular or oval shaped. The ports 172 are sized to receive the ureteral catheters 112, 114 and, accordingly, can have a diameter ranging from about 0.33 mm to about 3 mm. As shown in FIG. 13, in another example, the bladder catheter 116 is positioned next to the balloon 144, rather than extending through a central cavity defined by the balloon 144. As in other examples, the ureteral catheters 112, 114 extend through ports 172 in the sidewall of the bladder catheter 116 and into the bladder 10.

Figure 12B:
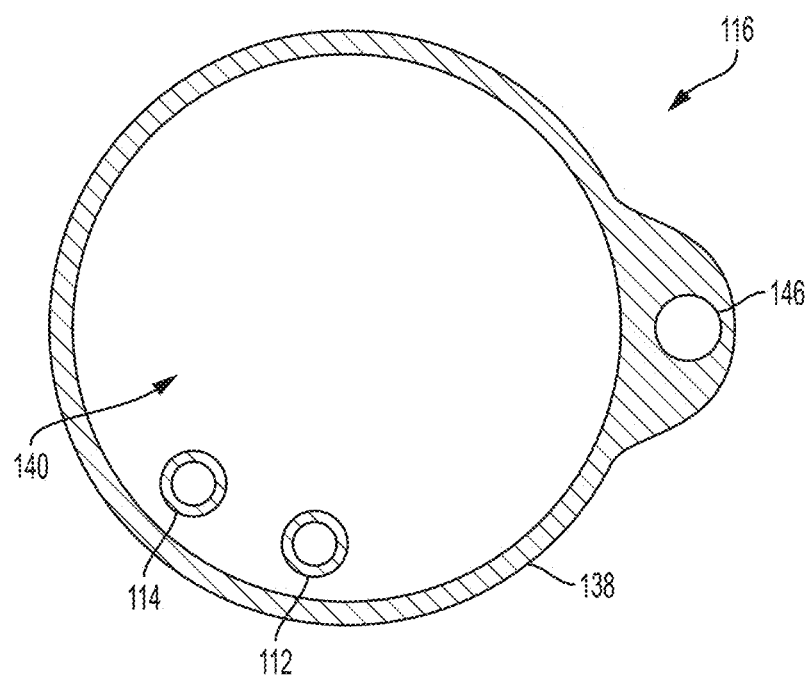
FIG. 12B is a schematic drawing of a cross section of a bladder catheter of a urine collection assembly, taken along line C-C of FIG. 12A.
Figure 12C:
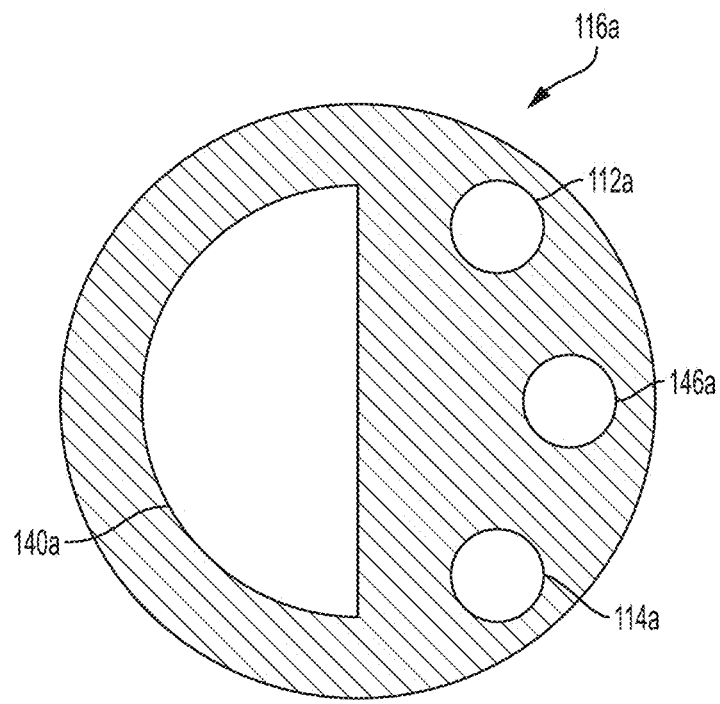
FIG. 12C is a schematic drawing of a cross section of another example of a bladder catheter of a urine collection assembly.

With reference to FIG. 12B, a cross-sectional view of the bladder catheter 116 and ureteral catheter(s) 112, 114 is shown. As shown in FIG. 12B, in one example, the bladder catheter 116 comprises a dual lumen catheter with the drainage lumen 140 at a central region thereof and a smaller inflation lumen 146 extending along the periphery of the catheter tube 138. The ureteral catheters 112, 114 are inserted or enclosed in the central drainage lumen 140. The ureteral catheters 112, 114 are single-lumen catheters having a sufficiently narrow cross section to fit within the drainage lumen 140. In some examples, as discussed above, the ureteral catheters 112, 114 extend through the entire bladder catheter 116. In other examples, the ureteral catheters 112, 114 terminate in the drainage lumen 140 of the bladder catheter 116, either at a position in the patient's ureter 12 or in an external portion of the drainage lumen 140. As shown in FIG. 12C, in another example, a bladder catheter 116a is a multi-lumen catheter that defines at least four lumens, namely a first lumen 112a for conducting fluid from the first ureteral catheter 112 (shown in FIG. 1), a second lumen 114a for conducting fluid from the second ureteral catheter 114 (shown in FIG. 1), a third lumen 140a for drainage of urine from the bladder 10 (shown in FIG. 1), and the inflation lumen 146a for conducting fluid to and from the balloon 144 (shown in FIG. 12A) for inflation and retraction thereof.

Figure 15:
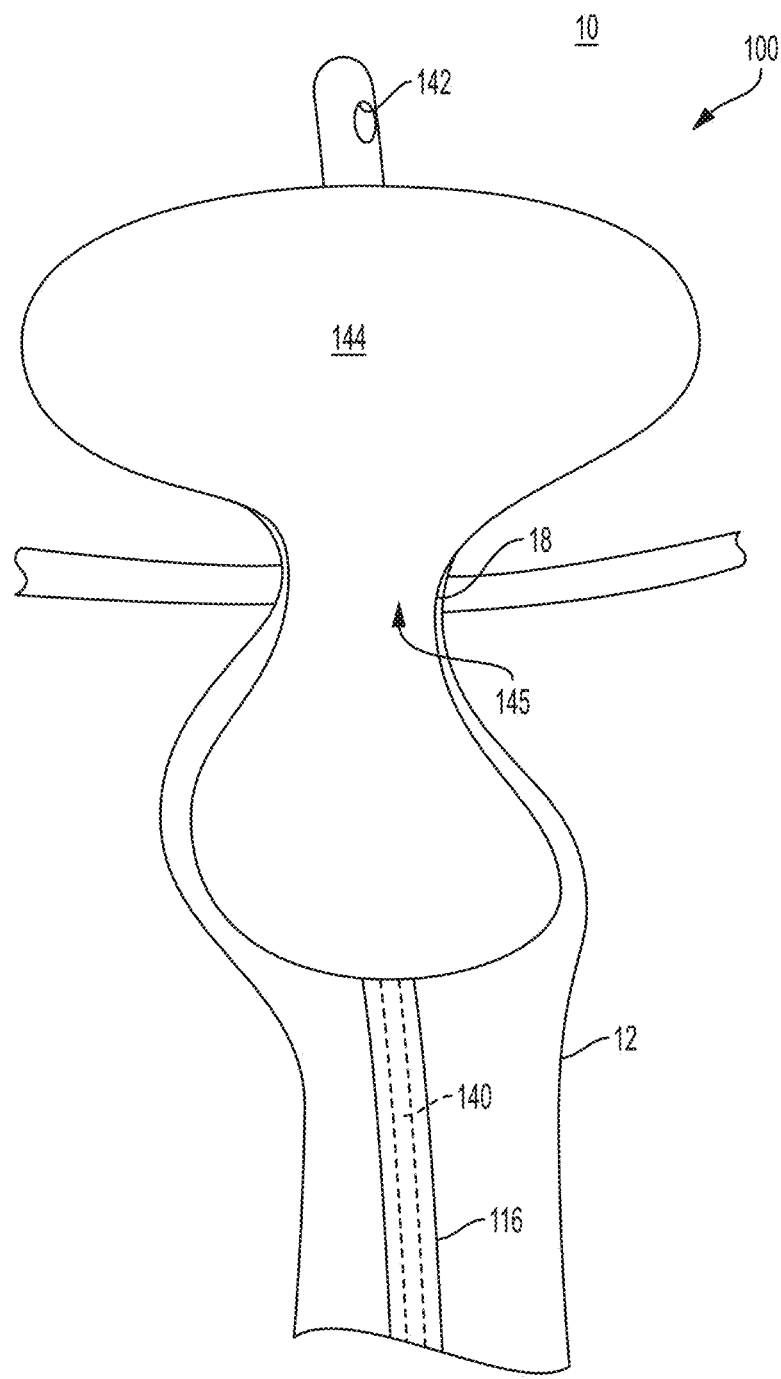
FIG. 15 is a schematic drawing of another example of a bladder anchor portion of a urine collection assembly configured to be deployed in the patient's bladder and urethra according to an example of the present invention.

As shown in FIG. 15, another example of a catheter balloon 144 for use with a urine collection assembly 100 is illustrated. In the example of FIG. 15, the balloon 144 is configured to be positioned partially within the patient's bladder 10 and partially within the urethra 12 to provide an enhanced bladder seal. A central portion 145 of the balloon 144 is configured to be radially contracted by the urethral opening 18, thereby defining a bulbous upper volume configured to be positioned in the lower portion of the bladder 10 and a bulbous lower volume configured to be position at the distal portion of the urethra 12. As in previously-described examples, the bladder catheter 116 extends through a central cavity defined by the balloon 144 and toward a central portion of the bladder 10 and includes drainage ports 142 for conducting urine from the bladder 10 through a drainage lumen 140 of the catheter 116. The drainage ports 142 can be generally circular or oval shaped and can have a diameter of about 0.005 mm to about 8.0 mm.

Figure 9B:
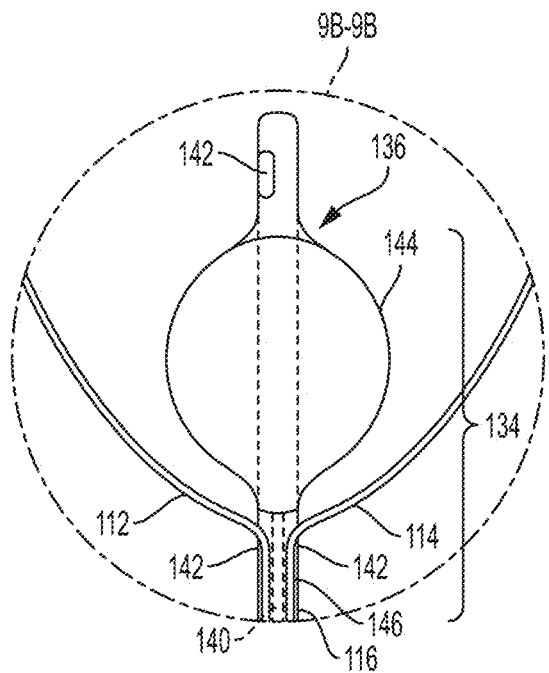
FIG. 9B is a partial schematic drawing taken along section 9B-9B of the bladder anchor portion of the assembly of FIG. 9A.

With reference again to FIGS. 9A and 9B, another example of a urine collection assembly 100 including a bladder anchor device 134 is illustrated. The bladder anchor device 134 comprises a bladder catheter 116 defining a drainage lumen 140, an inflation lumen 146, and an anchor 136, namely, another example of an expandable balloon 144, configured to be seated in a lower portion of the bladder 10. Unlike in the previously-described examples, the ports 142 configured to receive the ureteral catheters 112, 114 are disposed proximal to and/or below the balloon 144. The ureteral catheters 112, 114 extend from the ports 142 and, as in previously-described examples, extend through the ureteral orifices or openings of the bladder and into the ureters. When the anchor 136 is deployed in the bladder, the ports 142 are disposed in a lower portion of the bladder adjacent to the urethral opening. The ureteral catheters 112, 114 extend from the ports 172 and between a lower portion of the balloon 144 and the bladder wall. In some examples, the catheters 112, 114 may be positioned to prevent the balloon 144 and/or bladder wall from occluding the ports 142 so that excess urine collected in the bladder can be drawn into the ports 142 to be removed from the body.

Figure 10A:
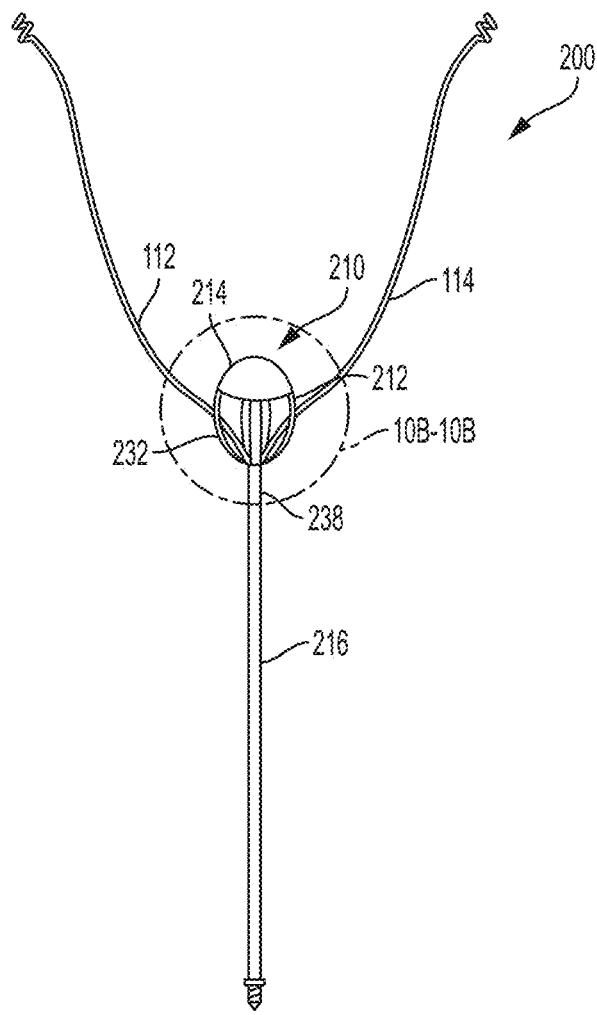
FIG. 10A is a schematic drawing of another example of a urine collection assembly according to an example of the present invention.
Figure 10B:
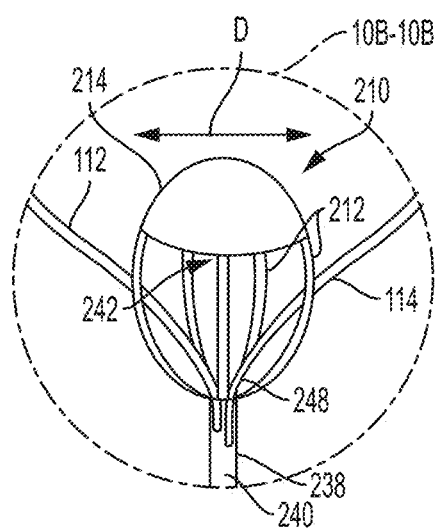
FIG. 10B is a schematic drawing taken along section 10B-10B of the bladder anchor portion of the assembly of FIG. 10A.

With reference again to FIGS. 10A and 10B, in another example of a urine collection assembly 200, an expandable cage 210 anchors the assembly 200 in the bladder. The expandable cage 210 comprises a plurality of flexible members 212 or tines extending longitudinally and radially outward from a catheter body 238 of a bladder catheter 216 which, in some examples, can be similar to those discussed above with respect to the retention portion of the ureteral catheter of FIG. 8. The members 212 can be formed from a suitable elastic and shape memory material such as nitinol. In a deployed position, the members 212 or tines are imparted with a sufficient curvature to define a spherical or ellipsoid central cavity 242. The cage 210 is attached to an open distal open end 248 of the catheter tube or body 238, to allow access to a drainage lumen 240 defined by the tube or body 238. The cage 210 is sized for positioning within the lower portion of the bladder and can define a diameter and length ranging from 1.0 cm to 2.3 cm, and preferably about 1.9 cm (0.75 in).

In some examples, the cage 210 further comprises a shield or cover 214 over distal portions of the cage 210 to prevent or reduce the likelihood that tissue, namely, the distal wall of the bladder, will be caught or pinched as a result of contact with the cage 210 or member 212. More specifically, as the bladder contracts, the inner distal wall of the bladder comes into contact with the distal side of the cage 210. The cover 214 prevents the tissue from being pinched or caught, may reduce patient discomfort, and protect the device during use. The cover 214 can be formed at least in part from a porous and/or permeable biocompatible material, such as a woven polymer mesh. In some examples, the cover 214 encloses all or substantially all of the cavity 242. In that case, the cover 214 defines openings suitable for receiving the ureteral catheters 112, 114. In some examples, the cover 214 covers only about the distal ⅔, about the distal half, or about the distal third portion or any amount, of the cage 210. In that case, the ureteral catheters 112, 114 pass through the uncovered portion of the cage 210.

The cage 210 and cover 214 are transitionable from a contracted position, in which the members 212 are contracted tightly together around a central portion and/or around the bladder catheter 116 to permit insertion through a catheter or sheath to the deployed position. For example, in the case of a cage 210 constructed from a shape memory material, the cage 210 can be configured to transition to the deployed position when it is warmed to a sufficient temperature, such as body temperature (e.g., 37° C.). In the deployed position, the cage 210 has a diameter D that is preferably wider than the urethral opening, such that the cage 210 provides support for the ureteral catheters 112, 114 and prevents patient motion from translating through the ureteral catheters 112, 114 to the ureters. When the assembly 200 is deployed in the urinary tract, the ureteral catheter(s) 112, 114 extend from the open distal end 248 of the bladder catheter 216, past the longitudinally extending members 212 of the cage 210, and into the bladder. Advantageously, the open (e.g., low profile) arrangement of the members 212 or tines facilitates manipulation of the ureteral catheters 112, 114 from the bladder catheter 116 and through the bladder. Particularly, the open arrangement of the members 212 or tines does not obstruct or occlude the distal opening 248 and/or drainage ports of the bladder catheter 216, making manipulation of the catheters 112, 114 easier to perform.

Figure 16:
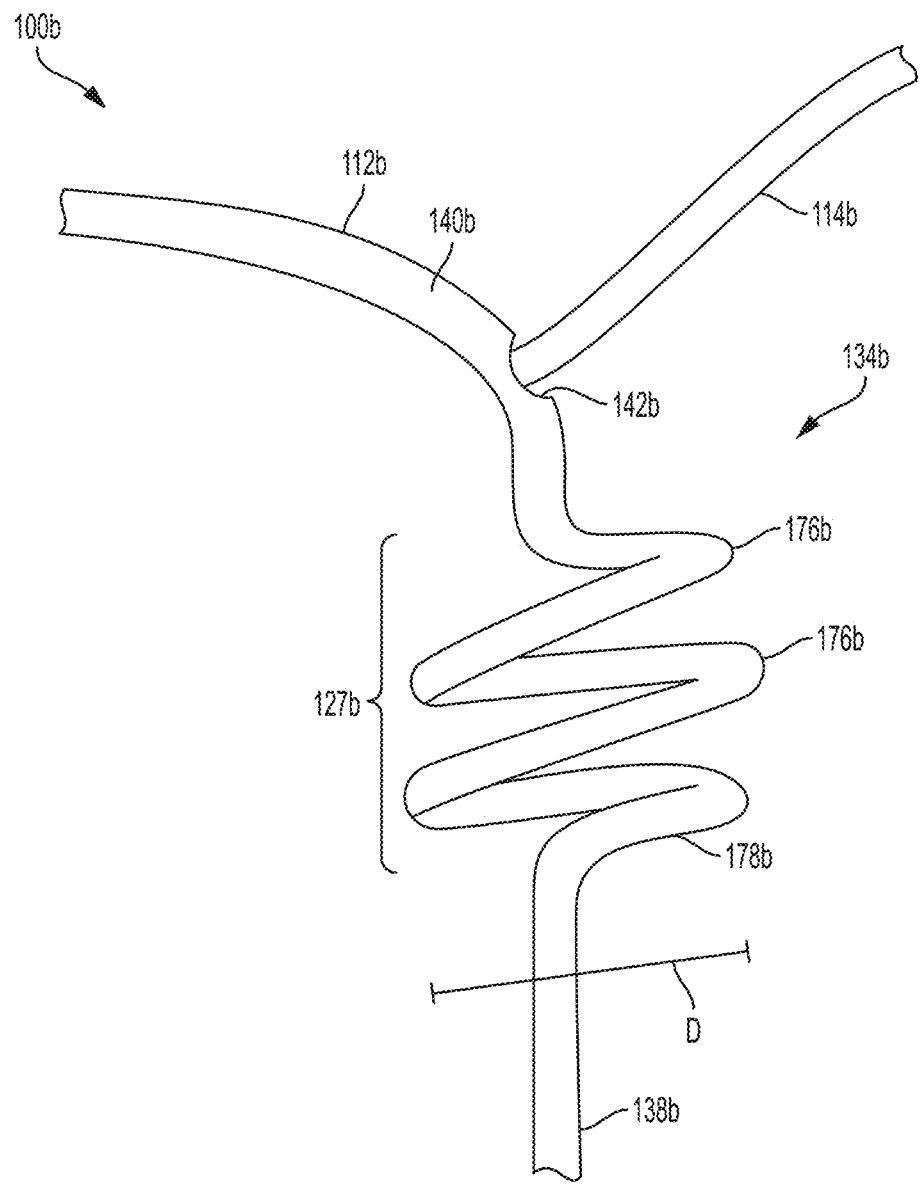
FIG. 16 is a schematic drawing of another example of a bladder anchor portion of a urine collection assembly according to an example of the present invention.

With reference to FIG. 16, a portion of another example of a urine collection assembly 100b is illustrated. The urine collection assembly 100b comprises a first ureteral catheter 112b and a second ureteral catheter 114b. The assembly 100b does not comprise a separate bladder drainage catheter as is provided in the previously-described examples. Instead, one of the ureteral catheters 112b comprises a helical portion 127b formed in the middle portion of the catheter 112b (e.g., the portion of the catheter configured to be positioned in a lower portion of the patient's bladder). The helical portion 127b comprises at least one and preferably two or more coils 176b. The coils 176b can be formed by bending a catheter tube 138b to impart a desired coil configuration. A lower coil 178b of the helical portion 127b is configured to be seated against and/or adjacent to the urethral opening. Desirably, the helical portion 127b has a diameter D that is larger than the urethral opening to prevent the helical portion 127b from being drawn into the urethra. In some examples, a port 142b or opening is disposed in the sidewall of the catheter tube 138b for connecting the first ureteral catheter 112b to the second ureteral catheter 114b. For example, the second catheter 114b can be inserted in the port 142b to form a fluid connection between the first ureteral catheter 112b and the second ureteral catheter 114b. In some examples, the second catheter 114b terminates at a position just inside a drainage lumen 140b of the first catheter 112b. In other examples, the second ureteral catheter 114b is threaded through and/or extends along the length of the drainage lumen 140b of the first catheter 112b, but is not in fluid communication with the drainage lumen 140b.

Figure 11B:
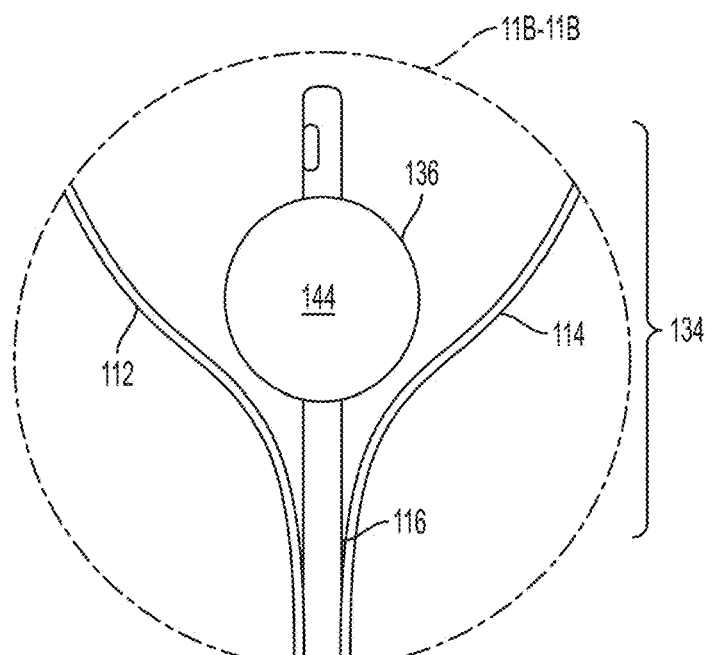
FIG. 11B is a schematic drawing taken along section 11B-11B of a bladder anchor portion of the assembly of FIG. 11A.

With reference again to FIGS. 11A and 11B, another exemplary urine collection assembly 100 comprising a bladder anchor device 134 is illustrated. The assembly 100 includes ureteral catheters 112, 114 and a separate bladder catheter 116. More specifically, as in previously-described examples, the assembly 100 includes the ureteral catheters 112, 114, each of which comprise a distal portion 118 positioned in or adjacent to the right kidney and the left kidney, respectively. The ureteral catheters 112, 114 comprise indwelling portions 118, 126, 128 extending through the ureters, bladder, and urethra. The ureteral catheters 112, 114 further comprise an external portion 170 extending from the patient's urethra 12 to a pump assembly for imparting negative pressure to the renal pelvis and/or kidneys. The assembly 100 also includes a bladder anchor device 134 comprising a bladder catheter 116 and an anchor 136 (e.g., a Foley catheter) deployed in the bladder to prevent or reduce effects of patient motion from being translated to the ureteral catheters 112, 114 and/or ureters. The bladder catheter 116 extends from the bladder 10, through the urethra, and to a fluid collection container for fluid collection by gravity or negative pressure drainage. In some examples, an external portion of the tubing extending between a collection vessel 712 and a pump 710 (shown in FIG. 19) can comprise one or more filters for preventing urine and/or particulates from entering the pump. As in previously-described examples, the bladder catheter 116 is provided to drain excess urine left in the patient's bladder during catheter placement.

Figure 17A:
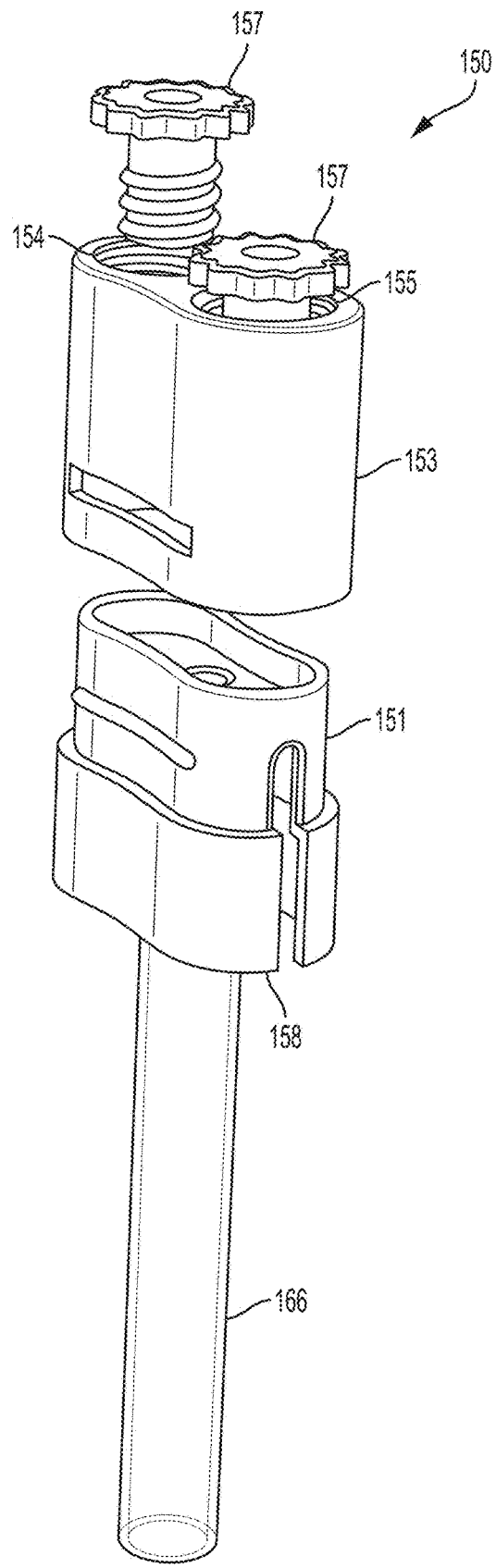
FIG. 17A is an exploded perspective view of a connector for a urine collection assembly according to an example of the disclosure.
Figure 17B:
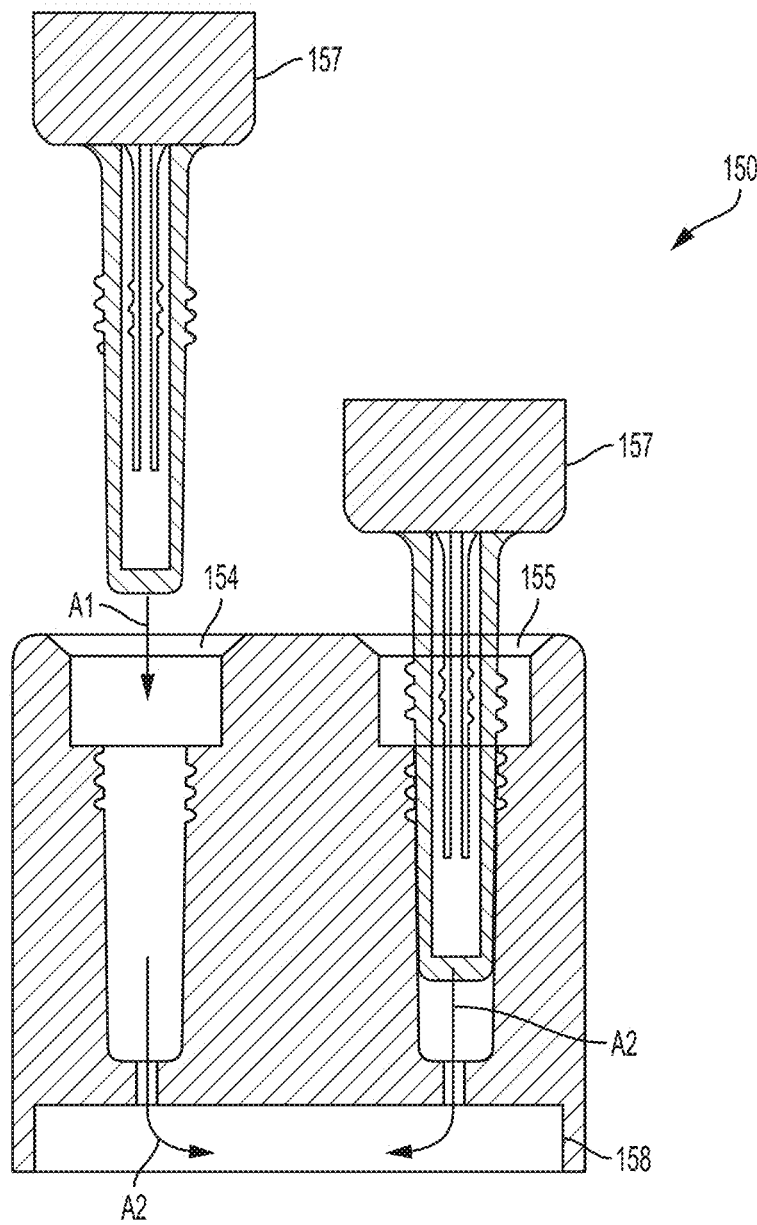
FIG. 17B is a cross-sectional view of a portion of the connector of FIG. 17A.

Exemplary Connectors and Clamps:

With reference to FIGS. 1, 11A, and 17A-17C, the assembly 100 further comprises a manifold or connector 150 for joining the two or more of the catheters 112, 114, 116 at a position outside the patient's body. In some examples, the connector 150 can be a clamp, manifold, valve, fastener, or other element of a fluid path set, as is known in the art, for joining a catheter to external flexible tubing. As shown in FIGS. 17A and 17B, the manifold or connector 150 comprises a two-piece body comprising an inner portion 151 mounted inside an outer housing 153. The inner portion 151 defines channels for conducting fluid between inflow ports 154, 155 and an outflow port 158. The inflow port(s) 154, 155 can comprise threaded sockets 157 configured to receive proximal portions of the catheters 112, 114. Desirably, the sockets 157 are a suitable size to securely receive and hold flexible tubing sized between 1 Fr and 9 Fr. Generally, a user cinches the sockets 157 around the respective catheter tubes 122 by spinning the socket 157 into the ports 154, 155 in the direction of arrow A1 (shown in FIG. 17B).

Once the catheters 112, 114 are mounted to the connector 150, urine entering the connector 150 through the vacuum inflow ports 154, 155 is directed through a fluid conduit in the direction of arrow A2 (shown in FIG. 17B) to the vacuum outflow port 158. The vacuum outflow port 158 can be connected to the fluid collection container 712 and/or pump assembly 710 (shown in FIG. 19) by, for example, flexible tubing 166 defining a fluid flow path.

Figure 17C:
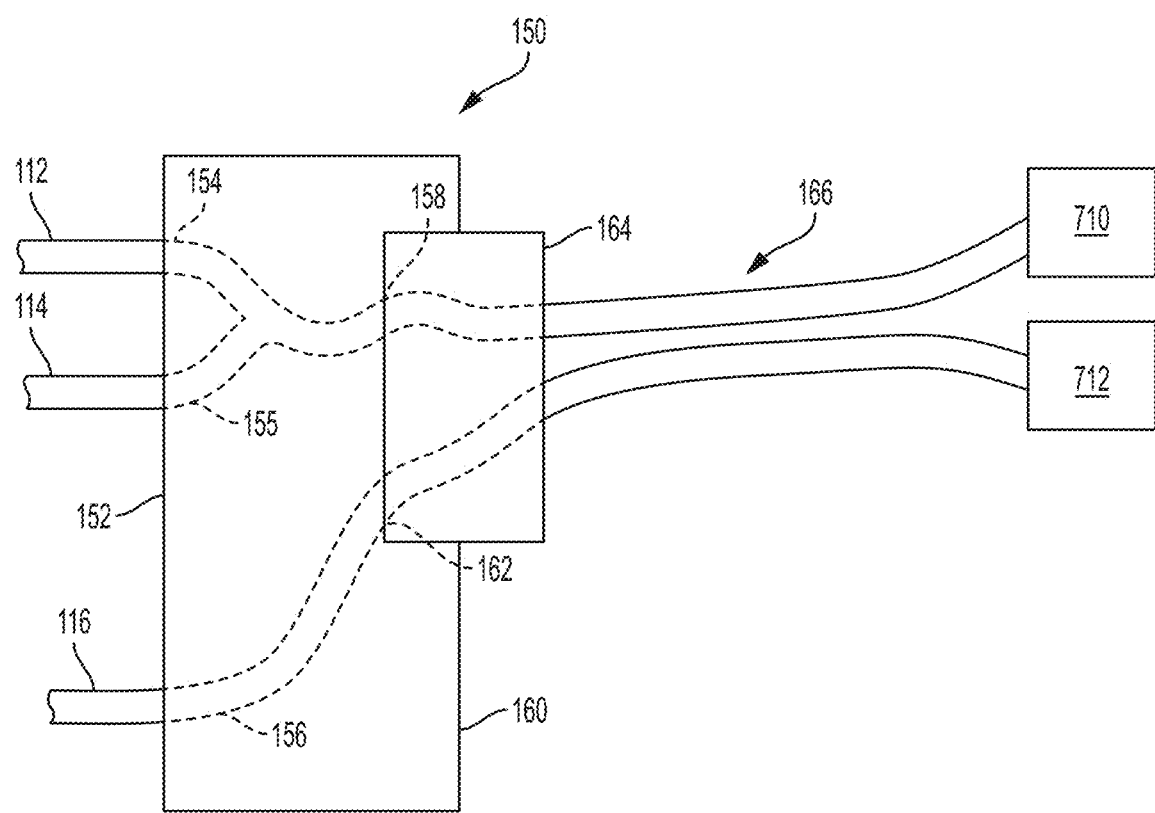
FIG. 17C is a schematic drawing of a connector for a urine collection assembly according to an example of the disclosure.

With specific reference to FIG. 17C, another exemplary connector 150 can be configured to connect three or more catheters 112, 114, 116 to outflow ports 158, 162. The connector 150 can comprise a structure or body having a distal side 152 comprising two or more vacuum inflow ports 154, 155 configured to be connected to proximal ends of the ureteral catheters 112, 114, and a separate gravity drainage port 156 configured to connect to the proximal end of the bladder catheter 116. The vacuum ports 154, 155 and/or proximal ends of the ureteral catheters 112, 114 can comprise a specific configuration to ensure that the ureteral catheters 112, 114 are connected to the vacuum source and not to some other fluid collection assembly. Similarly, the gravity drainage port 156 and/or proximal end of the bladder catheter 116 can comprise another connector configuration to ensure that the bladder catheter 116 and not one of the ureteral catheters 112, 114 is permitted to drain by gravity drainage. In other examples, the ports 154, 155, 156 and/or proximal ends of the catheters 112, 114, 116 can include visual indicia to assist in correctly setting up the fluid collection system.

In some examples, urine received in the vacuum ports 154, 155 can be directed through a Y-shaped conduit to a single vacuum outflow port 158 located on a proximal side 160 of the connector 150. As in previously-described examples, the vacuum outflow port 158 can be connected to the fluid collection container 712 and/or pump 710 by suitable flexible tubing or other conduits for drawing urine from the body and for inducing negative pressure in the ureters and/or kidneys. In some examples, the outflow port 156 and/or connector 150 can be configured to attach only to vacuum sources or pumps operating within a predetermined pressure range or power level to prevent exposing the ureteral catheters 112, 114 to elevated levels or intensity of negative pressure. The proximal side 160 of the connector 150 can also comprise a gravity outflow port 162 in fluid communication with the inflow port 156. The gravity outflow port 162 can be configured to be connected directly to the urine collection container 712 for urine collection by gravity drainage.

With continued reference to FIG. 17C, in some examples, in order to facilitate system setup and implementation, the vacuum outflow port 158 and the gravity outflow port 162 are disposed in close proximity so that a single socket 164, bracket, or connector can be coupled to the connector 150 to establish fluid communication with each port 158, 162. The single socket or connector can be coupled to a multi-conduit hose or tube (e.g., flexible tubing 166) having a first conduit in fluid communication with the pump 710 and a second conduit in fluid communication with the collection container 712. Accordingly, a user can easily set up the external fluid collection system by inserting the single socket 164 in the connector 150 and connecting the respective conduits to one of the fluid collection container 712 and pump 710 (shown in FIG. 19). In other examples, a length of flexible tubing 166 is connected between the urine collection container 712 and the gravity outflow port 162, and a separate length of flexible tubing is connected between the pump 710 and the vacuum outflow port 158.

Exemplary Fluid Sensors:

With reference again to FIG. 1, in some examples, the assembly 100 further comprises sensors 174 for monitoring fluid characteristics of urine being collected from the ureters 6, 8 and/or bladder 10. As discussed herein in connection with FIG. 19, information obtained from the sensors 174 can be transmitted to a central data collection module or processor and used, for example, to control operation of an external device, such as the pump 710 (shown in FIG. 19). The sensors 174 can be integrally formed with one or more of the catheters 112, 114, 116 such as, for example, embedded in a wall of the catheter body or tube and in fluid communication with drainage lumens 124, 140. In other examples, one or more of the sensors 174 can be positioned in a fluid collection container 712 (shown in FIG. 19) or in internal circuitry of an external device, such as the pump 710.

Exemplary sensors 174 that can be used with the urine collection assembly 100 can comprise one or more of the following sensor types. For example, the catheter assembly 100 can comprise a conductance sensor or electrode that samples conductivity of urine. The normal conductance of human urine is about 5-10 mS/m. Urine having a conductance outside of the expected range can indicate that the patient is experiencing a physiological problem, which requires further treatment or analysis. The catheter assembly 100 can also comprise a flow meter for measuring a flow rate of urine through the catheter(s) 112, 114, 116. Flow rate can be used to determine a total volume of fluid excreted from the body. The catheter(s) 112, 114, 116 can also comprise a thermometer for measuring urine temperature. Urine temperature can be used to collaborate the conductance sensor. Urine temperature can also be used for monitoring purposes, as urine temperature outside of a physiologically normal range can be indicative of certain physiological conditions. In some examples, the sensors 174 can be urine analyte sensors configured to measure a concentration of creatinine and/or proteins in urine. For example, various conductivity sensors and optical spectrometry sensors may be used for determining analyte concentration in urine. Sensors based on color change reagent test strips may also be used for this purpose.

Method of Insertion of a Urine Collection Assembly:

Having described the urine collection assembly 100 including the ureteral catheter retention portions and bladder anchor device (e.g., a standard or modified Foley-type catheter), methods for insertion and deployment of the assemblies will now be discussed in detail.

Figure 18A:
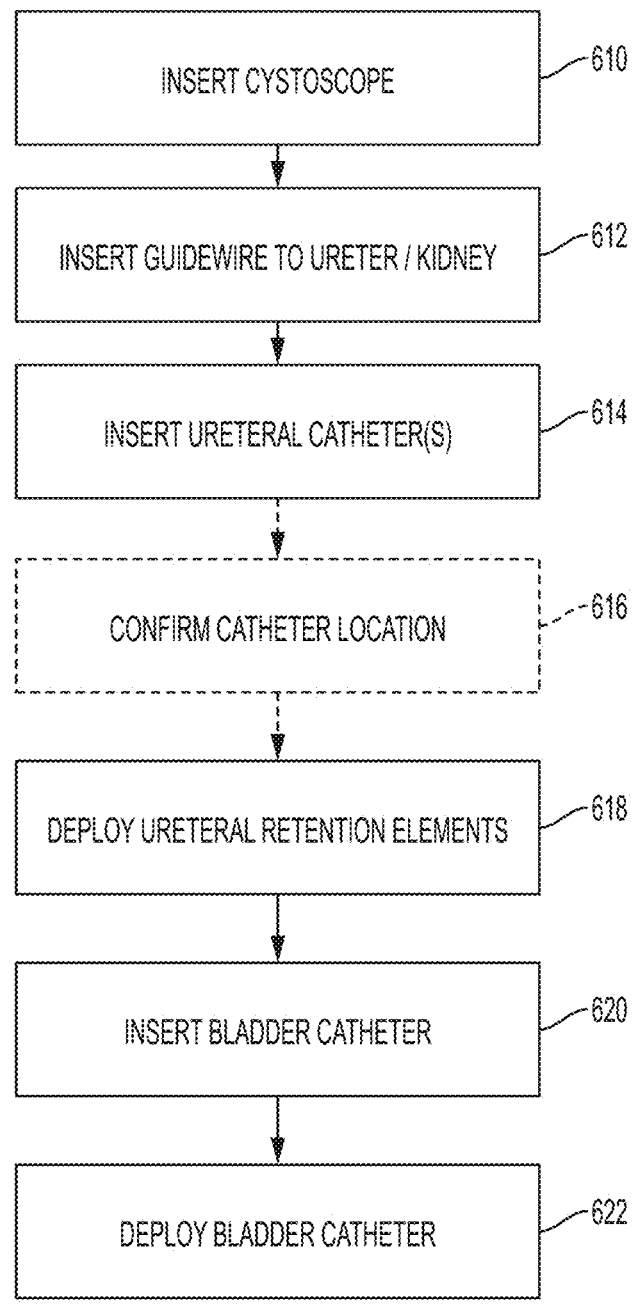
FIG. 18A is a flow chart illustrating a process for insertion and deployment of a ureteral catheter or urine collection assembly according to an example of the present invention.

With reference to FIG. 18A, steps for positioning a fluid collection assembly in a patient's body and, optionally, for inducing negative pressure in a patient's ureter and/or kidneys are illustrated. As shown at box 610, a medical professional or caregiver inserts a flexible or rigid cystoscope through the patient's urethra and into the bladder to obtain visualization of the ureteral orifices or openings. Once suitable visualization is obtained, as shown at box 612, a guidewire is advanced through the urethra, bladder, ureteral opening, ureter, and to a desired fluid collection position, such as the renal pelvis of the kidney. Once the guidewire is advanced to the desired fluid collection position, a ureteral catheter of the present invention (examples of which are discussed in detail above) is inserted over the guidewire to the fluid collection position, as shown at box 614. In some examples, the location of the ureteral catheter can be confirmed by fluoroscopy, as shown at box 616. Once the position of the distal end of the catheter is confirmed, as shown at box 618, the retention portion of the ureteral catheter can be deployed. For example, the guidewire can be removed from the catheter, thereby allowing the distal end and/or retention portion to transition to a deployed position. In some examples, the deployed distal end portion of the catheter does not entirely occlude the ureter and/or renal pelvis, such that urine is permitted to pass outside the catheter and through the ureters into the bladder. Since moving the catheter can exert forces against urinary tract tissues, avoiding complete blockage of the ureters avoids application of force to the ureter sidewalls, which may cause injury.

After the ureteral catheter is in place and deployed, the same guidewire can be used to position a second ureteral catheter in the other ureter and/or kidney using the same insertion and positioning methods described herein. For example, the cystoscope can be used to obtain visualization of the other ureteral opening in the bladder, and the guidewire can be advanced through the visualized ureteral opening to a fluid collection position in the other ureter. A catheter can be drawn alongside the guidewire and deployed in the manner described herein. Alternatively, the cystoscope and guidewire can be removed from the body. The cystoscope can be reinserted into the bladder over the first ureteral catheter. The cystoscope is used, in the manner described above, to obtain visualization of the ureteral opening and to assist in advancing a second guidewire to the second ureter and/or kidney for positioning of the second ureteral catheter. Once the ureteral catheters are in place, in some examples, the guidewire and cystoscope are removed. In other examples, the cystoscope and/or guidewire can remain in the bladder to assist with placement of the bladder catheter.

Optionally, a bladder catheter can also be used. Once the ureteral catheters are in place, as shown at box 620, the medical professional or caregiver can insert a distal end of a bladder catheter in a collapsed or contracted state through the urethra of the patient and into the bladder. The bladder catheter can be a conventional Foley bladder catheter or a bladder catheter of the present invention as discussed in detail above. Once inserted in the bladder, as shown at box 622, an anchor connected to and/or associated with the bladder catheter is expanded to a deployed position. For example, when an expandable or inflatable catheter is used, fluid may be directed through an inflation lumen of the bladder catheter to expand a balloon structure located in the patient's bladder. In some examples, the bladder catheter is inserted through the urethra and into the bladder without using a guidewire and/or cystoscope. In other examples, the bladder catheter is inserted over the same guidewire used to position the ureteral catheters. Accordingly, when inserted in this manner, the ureteral catheters can be arranged to extend from the distal end of the bladder catheter and, optionally, proximal ends of the ureteral catheters can be arranged to terminate in a drainage lumen of the bladder catheter.

In some examples, the urine is permitted to drain by gravity from the urethra. In other examples, a negative pressure is induced in the ureteral catheter and/or bladder catheter to facilitate drainage of the urine.

Figure 18B:
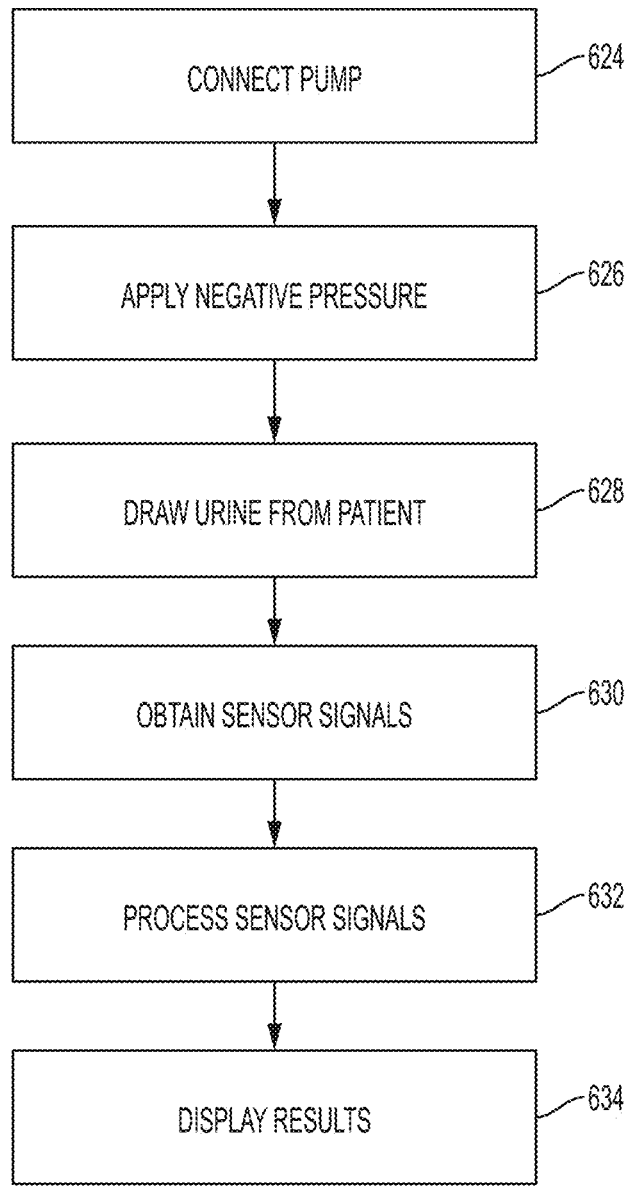
FIG. 18B is a flow chart illustrating a process for applying negative pressure using a ureteral catheter or urine collection assembly according to an example of the present invention.

With reference to FIG. 18B, steps for using the urine collection assembly for inducement of negative pressure in the ureter(s) and/or kidney(s) are illustrated. As shown at box 624, after the indwelling portions of the bladder and/or ureteral catheters are correctly positioned and anchoring/retention structures are deployed, the external proximal ends of the catheter(s) are connected to fluid collection or pump assemblies. For example, the ureteral catheter(s) can be connected to a pump for inducing negative pressure at the patient's renal pelvis and/or kidney. In a similar manner, the bladder catheter can be connected directly to a urine collection container for gravity drainage of urine from the bladder or connected to a pump for inducing negative pressure at the bladder.

Once the catheter(s) and pump assembly are connected, negative pressure is applied to the renal pelvis and/or kidney and/or bladder through the drainage lumens of the ureteral catheters and/or bladder catheter, as shown at box 626. The negative pressure is intended to counter congestion mediated interstitial hydrostatic pressures due to elevated intra-abdominal pressure and consequential or elevated renal venous pressure or renal lymphatic pressure. The applied negative pressure is therefore capable of increasing flow of filtrate through the medullary tubules and of decreasing water and sodium re-absorption.

In some examples, mechanical stimulation can be provided to portions of the ureters and/or renal pelvis to supplement or modify therapeutic affects obtained by application of negative pressure. For example, mechanical stimulation devices, such as linear actuators and other known devices for providing, for example, vibration waves, disposed in distal portions of the ureteral catheter(s) can be actuated. While not intending to be bound by theory, it is believed that such stimulation effects adjacent tissues by, for example, stimulating nerves and/or actuating peristaltic muscles associated with the ureter(s) and/or renal pelvis. Stimulation of nerves and activation of muscles may produce changes in pressure gradients or pressure levels in surrounding tissues and organs which may contribute to or, in some cases, enhance therapeutic benefits of negative pressure therapy. In some examples, the mechanical stimulation can comprise pulsating stimulation. In other examples, low levels of mechanical stimulation can be provided continuously as negative pressure is being provided through the ureteral catheter(s). In other examples, inflatable portions of the ureteral catheter could be inflated and deflated in a pulsating manner to stimulate adjacent nerve and muscle tissue, in a similar manner to actuation of the mechanical stimulation devices described herein.

As a result of the applied negative pressure, as shown at box 628, urine is drawn into the catheter at the plurality of drainage ports at the distal end thereof, through the drainage lumen of the catheter, and to a fluid collection container for disposal. As the urine is being drawn to the collection container, at box 630, sensors disposed in the fluid collection system provide a number of measurements about the urine that can be used to assess the volume of urine collected, as well as information about the physical condition of the patient and composition of the urine produced. In some examples, the information obtained by the sensors is processed, as shown at box 632, by a processor associated with the pump and/or with another patient monitoring device and, at box 634, is displayed to the user via a visual display of an associated feedback device.

Figure 19:
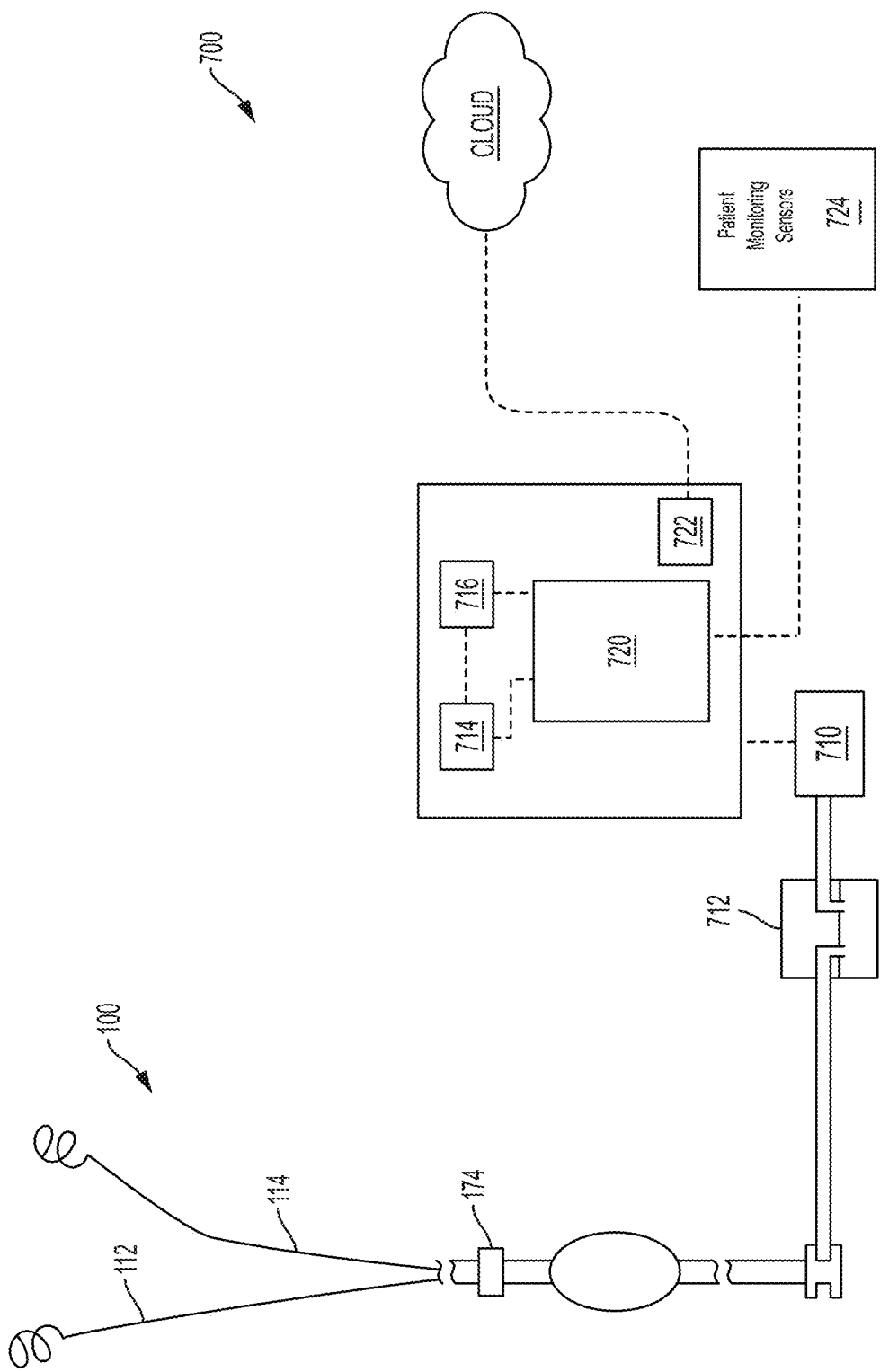
FIG. 19 is a schematic drawing of a system for inducing negative pressure to the urinary tract of a patient according to an example of the present invention.

Exemplary Fluid Collection System:

Having described an exemplary urine collection assembly and method of positioning such an assembly in the patient's body, with reference to FIG. 19, a system 700 for inducing negative pressure to a patient's ureter(s) and/or kidney(s) will now be described. The system 700 can comprise the ureteral catheter(s), bladder catheter or the urine collection assembly 100 described hereinabove. As shown in FIG. 19, ureteral catheters 112, 114 and/or the bladder catheter 116 of the assembly 100 are connected to one or more fluid collection containers 712 for collecting urine drawn from the renal pelvis and/or bladder. In some examples, the bladder catheter 116 and the ureteral catheters 112, 114 are connected to different fluid collection containers 712. The fluid collection container 712 connected to the ureteral catheter(s) 112, 114 can be in fluid communication with an external fluid pump 710 for generating negative pressure in the ureter(s) and kidney(s) through the ureteral catheter(s) 112, 114. As discussed herein, such negative pressure can be provided for overcoming interstitial pressure and forming urine in the kidney or nephron. In some examples, a connection between the fluid collection container 712 and pump 710 can comprise a fluid lock or fluid barrier to prevent air from entering the renal pelvis or kidney in case of incidental therapeutic or non-therapeutic pressure changes. For example, inflow and outflow ports of the fluid container can be positioned below a fluid level in the container. Accordingly, air is prevented from entering medical tubing or the catheter through either the inflow or outflow ports of the fluid container 712. As discussed previously, external portions of the tubing extending between the fluid collection container 712 and the pump 710 can include one or more filters to prevent urine and/or particulates from entering the pump 710.

As shown in FIG. 19, the system 700 further comprises a controller 714, such as a microprocessor, electronically coupled to the pump 710 and having or associated with computer readable memory 716. In some examples, the memory 716 comprises instructions that, when executed, cause the controller 714 to receive information from sensors 174 located on or associated with portions of the assembly 100. Information about a condition of the patient can be determined based on information from the sensors 174. Information from the sensors 174 can also be used to determine and implement operating parameters for the pump 710.

In some examples, the controller 714 is incorporated in a separate and remote electronic device in communication with the pump 710, such as a dedicated electronic device, computer, tablet PC, or smart phone. Alternatively, the controller 714 can be included in the pump 710 and, for example, can control both a user interface for manually operating the pump 710, as well as system functions such as receiving and processing information from the sensors 174.

The controller 714 is configured to receive information from the one or more sensors 174 and to store the information in the associated computer-readable memory 716. For example, the controller 714 can be configured to receive information from the sensor 174 at a predetermined rate, such as once every second, and to determine a conductance based on the received information. In some examples, the algorithm for calculating conductance can also include other sensor measurements, such as urine temperature, to obtain a more robust determination of conductance.

The controller 714 can also be configured to calculate patient physical statistics or diagnostic indicators that illustrate changes in the patient's condition over time. For example, the system 700 can be configured to identify an amount of total sodium excreted. The total sodium excreted may be based, for example, on a combination of flow rate and conductance over a period of time.

With continued reference to FIG. 19, the system 700 can further comprise a feedback device 720, such as a visual display or audio system, for providing information to the user. In some examples, the feedback device 720 can be integrally formed with the pump 710. Alternatively, the feedback device 720 can be a separate dedicated or a multipurpose electronic device, such as a computer, laptop computer, tablet PC, smart phone, or other handheld electronic devices. The feedback device 720 is configured to receive the calculated or determined measurements from the controller 714 and to present the received information to a user via the feedback device 720. For example, the feedback device 720 may be configured to display current negative pressure (in mmHg) being applied to the urinary tract. In other examples, the feedback device 720 is configured to display current flow rate of urine, temperature, current conductance in mS/m of urine, total urine produced during the session, total sodium excreted during the session, other physical parameters, or any combination thereof.

In some examples, the feedback device 720 further comprises a user interface module or component that allows the user to control operation of the pump 710. For example, the user can engage or turn off the pump 710 via the user interface. The user can also adjust pressure applied by the pump 710 to achieve a greater magnitude or rate of sodium excretion and fluid removal.

Optionally, the feedback device 720 and/or pump 710 further comprise a data transmitter 722 for sending information from the device 720 and/or pump 710 to other electronic devices or computer networks. The data transmitter 722 can utilize a short-range or long-range data communications protocol. An example of a short-range data transmission protocol is Bluetooth®. Long-range data transmission networks include, for example, Wi-Fi or cellular networks. The data transmitter 722 can send information to a patient's physician or caregiver to inform the physician or caregiver about the patient's current condition. Alternatively, or in addition, information can be sent from the data transmitter 722 to existing databases or information storage locations, such as, for example, to include the recorded information in a patient's electronic health record (EHR).

With continued reference to FIG. 19, in addition to the urine sensors 174, in some examples, the system 700 further comprises one or more patient monitoring sensors 724. Patient monitoring sensors 724 can include invasive and non-invasive sensors for measuring information about the patient's urine composition, as discussed in detail above, blood composition (e.g., hematocrit ratio, analyte concentration, protein concentration, creatinine concentration) and/or blood flow (e.g., blood pressure, blood flow velocity). Hematocrit is a ratio of the volume of red blood cells to the total volume of blood. Normal hematocrit is about 25% to 40%, and preferably about 35% and 40% (e.g., 35% to 40% red blood cells by volume and 60% to 65% plasma).

Non-invasive patient monitoring sensors 724 can include pulse oximetry sensors, blood pressure sensors, heart rate sensors, and respiration sensors (e.g., a capnography sensor). Invasive patient monitoring sensors 724 can include invasive blood pressure sensors, glucose sensors, blood velocity sensors, hemoglobin sensors, hematocrit sensors, protein sensors, creatinine sensors, and others. In still other examples, sensors may be associated with an extracorporeal blood system or circuit and configured to measure parameters of blood passing through tubing of the extracorporeal system. For example, analyte sensors, such as capacitance sensors or optical spectroscopy sensors, may be associated with tubing of the extracorporeal blood system to measure parameter values of the patient's blood as it passes through the tubing. The patient monitoring sensors 724 can be in wired or wireless communication with the pump 710 and/or controller 714.

In some examples, the controller 714 is configured to cause the pump 710 to provide treatment for a patient based information obtained from the urine analyte sensor 174 and/or patient monitoring sensors 724, such as blood monitoring sensors. For example, pump 710 operating parameters can be adjusted based on changes in the patient's blood hematocrit ratio, blood protein concertation, creatinine concentration, urine output volume, urine protein concentration (e.g., albumin), and other parameters. For example, the controller 714 can be configured to receive information about a blood hematocrit ratio or creatinine concentration of the patient from the patient monitoring sensors 724 and/or analyte sensors 174. The controller 714 can be configured to adjust operating parameters of the pump 710 based on the blood and/or urine measurements. In other examples, hematocrit ratio may be measured from blood samples periodically obtained from the patient. Results of the tests can be manually or automatically provided to the controller 714 for processing and analysis.

As discussed herein, measured hematocrit values for the patient can be compared to predetermined threshold or clinically acceptable values for the general population. Generally, hematocrit levels for females are lower than for males. In other examples, measured hematocrit values can be compared to patient baseline values obtained prior to a surgical procedure. When the measured hematocrit value is increased to within the acceptable range, the pump 710 may be turned off ceasing application of negative pressure to the ureter or kidneys. In a similar manner, the intensity of negative pressure can be adjusted based on measured parameter values. For example, as the patient's measured parameters begin to approach the acceptable range, intensity of negative pressure being applied to the ureter and kidneys can be reduced. In contrast, if an undesirable trend (e.g., a decrease in hematocrit value, urine output rate, and/or creatinine clearance) is identified, the intensity of negative pressure can be increased in order to produce a positive physiological result. For example, the pump 710 may be configured to begin by providing a low level of negative pressure (e.g., between about 0.1 mmHg and 10 mmHg). The negative pressure may be incrementally increased until a positive trend in patient creatinine level is observed. However, generally, negative pressure provided by the pump 710 will not exceed about 50 mmHg.

Figure 20A:
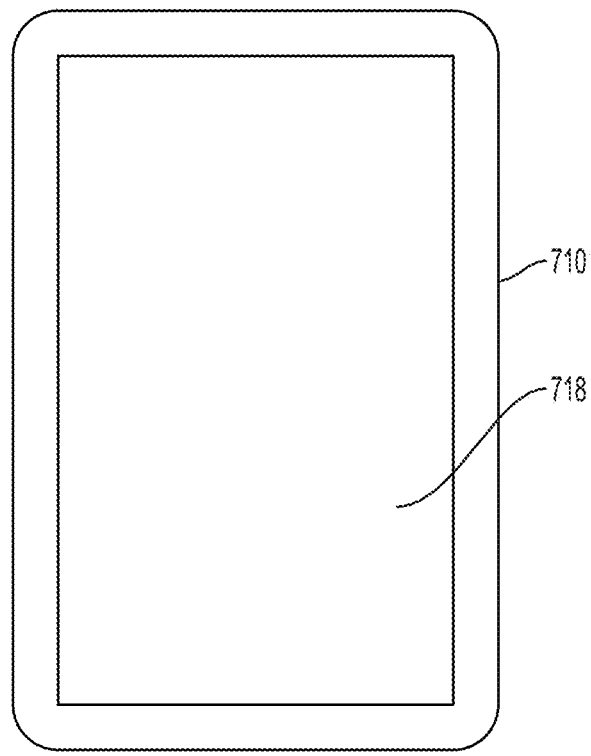
FIG. 20A is a plan view of a pump for use with the system of FIG. 19 according to an example of the present invention.
Figure 20B:
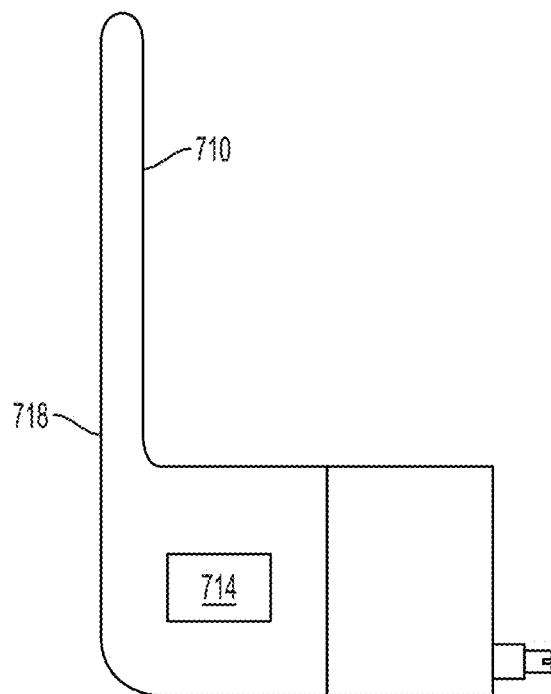
FIG. 20B is a side elevation view of the pump of FIG. 20A.

With reference to FIGS. 20A and 20B, an exemplary pump 710 for use with the system is illustrated. In some examples, the pump 710 is a micro-pump configured to draw fluid from the catheter(s) 112, 114 (shown, for example, in FIG. 1) and having a sensitivity or accuracy of about 10 mmHg or less. Desirably, the pump 710 is capable of providing a range of flow of urine between 0.05 ml/min and 3 ml/min for extended periods of time, for example, for about 8 hours to about 24 hours per day, for one (1) to about 30 days or longer. At 0.2 ml/min, it is anticipated that about 300 mL of urine per day is collected by the system 700. The pump 710 can be configured to provide a negative pressure to the bladder of the patient, the negative pressure ranging between about 0.1 mmHg and 50 mmHg or about 5 mmHg to about 20 mmHg (gauge pressure at the pump 710). For example, a micro-pump manufactured by Langer Inc. (Model BT100-2J) can be used with the presently disclosed system 700. Diaphragm aspirator pumps, as well as other types of commercially available pumps, can also be used for this purpose. Peristaltic pumps can also be used with the system 700. In other examples, a piston pump, vacuum bottle, or manual vacuum source can be used for providing negative pressure. In other examples, the system can be connected to a wall suction source, as is available in a hospital, through a vacuum regulator for reducing negative pressure to therapeutically appropriate levels.

In some examples, the pump 710 is configured for extended use and, thus, is capable of maintaining precise suction for extended periods of time, for example, for about 8 hours to about 24 hours per day, for 1 to about 30 days or longer. Further, in some examples, the pump 710 is configured to be manually operated and, in that case, includes a control panel 718 that allows a user to set a desired suction value. The pump 710 can also include a controller or processor, which can be the same controller that operates the system 700 or can be a separate processor dedicated for operation of the pump 710. In either case, the processor is configured for both receiving instructions for manual operation of the pump and for automatically operating the pump 710 according to predetermined operating parameters. Alternatively, or in addition, operation of the pump 710 can be controlled by the processor based on feedback received from the plurality of sensors associated with the catheter.

In some examples, the processor is configured to cause the pump 710 to operate intermittently. For example, the pump 710 may be configured to emit pulses of negative pressure followed by periods in which no negative pressure is provided. In other examples, the pump 710 can be configured to alternate between providing negative pressure and positive pressure to produce an alternating flush and pump effect. For example, a positive pressure of about 0.1 mmHg to 20 mmHg, and preferably about 5 mmHg to 20 mmHg can be provided followed by a negative pressure ranging from about 0.1 mmHg to 50 mmHg.

Treatment for Removing Excess Fluid from a Patient with Hemodilution

According to another aspect of the disclosure, a method for removing excess fluid from a patient with hemodilution is provided. In some examples, hemodilution can refer to an increase in a volume of plasma in relation to red blood cells and/or a reduced concentration of red blood cells in circulation, as may occur when a patient is provided with an excessive amount of fluid. The method can involve measuring and/or monitoring patient hematocrit levels to determine when hemodilution has been adequately addressed. Low hematocrit levels are a common post-surgical or post-trauma condition that can lead to undesirable therapeutic outcomes. As such, management of hemodilution and confirming that hematocrit levels return to normal ranges is a desirable therapeutic result for surgical and post-surgical patient care.

Figure 24:
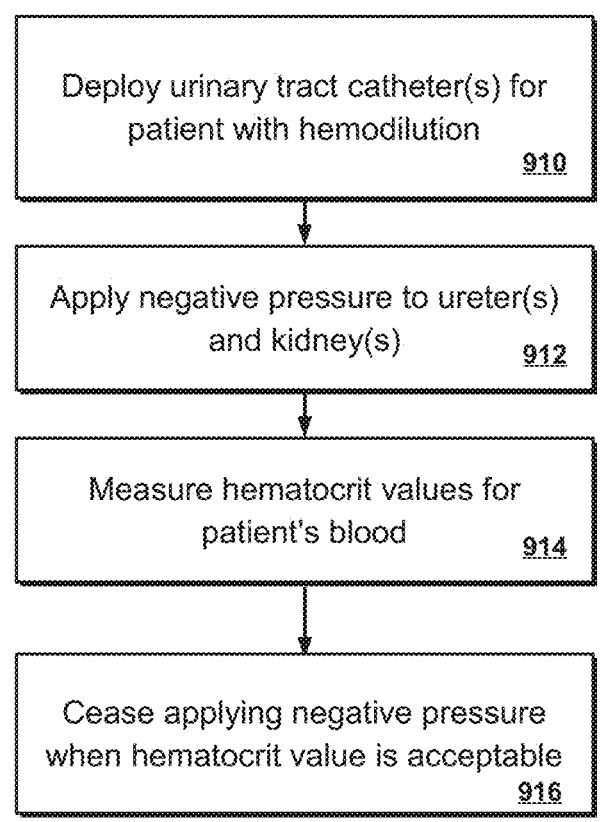
FIG. 24 is a flow chart illustrating a process for reducing creatinine and/or protein levels of a patient according to an example of the disclosure.

Steps for removing excess fluid from a patient using the devices and systems described herein are illustrated in FIG. 24. As shown in FIG. 24, the treatment method comprises deploying a urinary tract catheter, such as a ureteral catheter, in the ureter and/or kidney of a patient such that flow of urine from the ureter and/or kidney, as shown at box 910. The catheter may be placed to avoid occluding the ureter and/or kidney. In some examples, a fluid collecting portion of the catheter may be positioned in the renal pelvis of the patient's kidney. In some examples, a ureter catheter may be positioned in each of the patient's kidneys. In other examples, a urine collection catheter may be deployed in the bladder or ureter. In some examples, the ureteral catheter comprises one or more of any of the retention portions described herein. For example, the ureteral catheter can comprise a tube defining a drainage lumen comprising a helical retention portion and a plurality of drainage ports. In other examples, the catheter can include an inflatable retention portion (e.g., a balloon catheter), funnel-shaped fluid collection and retention portion, or a pigtail coil.

As shown at box 912, the method further comprises applying negative pressure to the ureter and/or kidney through the catheter to induce production of urine in the kidney(s) and to extract urine from the patient. Desirably, negative pressure is applied for a period of time sufficient to reduce the patient's blood creatinine levels by a clinically significant amount.

Negative pressure may continue to be applied for a predetermined period of time. For example, a user may be instructed to operate the pump for the duration of a surgical procedure or for a time period selected based on physiological characteristics of the patient. In other examples, patient condition may be monitored to determine when sufficient treatment has been provided. For example, as shown at box 914, the method may further comprise monitoring the patient to determine when to cease applying negative pressure to the patient's ureter and/or kidneys. In a preferred and non-limiting example, a patient's hematocrit level is measured. For example, patient monitoring devices may be used to periodically obtain hematocrit values. In other examples, blood samples may be drawn periodically to directly measure hematocrit. In some examples, concentration and/or volume of urine expelled from the body through the catheter may also be monitored to determine a rate at which urine is being produced by the kidneys. In a similar manner, expelled urine output may be monitored to determine protein concentration and/or creatinine clearance rate for the patient. Reduced creatinine and protein concentration in urine may be indicative of over-dilution and/or depressed renal function. Measured values can be compared to the predetermined threshold values to assess whether negative pressure therapy is improving patient condition, and should be modified or discontinued. For example, as discussed herein, a desirable range for patient hematocrit may be between 25% and 40%. In other preferred and non-limiting examples, as described herein, patient body weight may be measured and compared to a dry body weight. Changes in measured patient body weight demonstrate that fluid is being removed from the body. As such, a return to dry body weight represents that hemodilution has been appropriately managed and the patient is not over-diluted.

As shown at box 916, a user may cause the pump to cease providing negative pressure therapy when a positive result is identified. In a similar manner, patient blood parameters may be monitored to assess effectiveness of the negative pressure being applied to the patient's kidneys. For example, a capacitance or analyte sensor may be placed in fluid communication with tubing of an extracorporeal blood management system. The sensor may be used to measure information representative of blood protein, oxygen, creatinine, and/or hematocrit levels. Measured blood parameter values may be measured continuously or periodically and compared to various threshold or clinically acceptable values. Negative pressure may continue to be applied to the patient's kidney or ureter until a measured parameter value falls within a clinically acceptable range. Once a measured values fails within the threshold or clinically acceptable range, as shown at box 916, application of negative pressure may cease.

Treatment of Patients Undergoing a Fluid Resuscitation Procedure

According to another aspect of the disclosure, a method for removing excess fluid for a patient undergoing a fluid resuscitation procedure, such as coronary graft bypass surgery, by removing excess fluid from the patient is provided. During fluid resuscitation, solutions such as saline solutions and/or starch solutions, are introduced to the patient's bloodstream by a suitable fluid delivery process, such as an intravenous drip. For example, in some surgical procedures, a patient may be supplied with between 5 and 10 times a normal daily intake of fluid. Fluid replacement or fluid resuscitation can be provided to replace bodily fluids lost through sweating, bleeding, dehydration, and similar processes. In the case of a surgical procedure such as coronary graft bypass, fluid resuscitation is provided to help maintain a patient's fluid balance and blood pressure within an appropriate rate. Acute kidney injury (AKI) is a known complication of coronary artery graft bypass surgery. AKI is associated with a prolonged hospital stay and increased morbidity and mortality, even for patients who do not progress to renal failure. See Kim, et al., *Relationship between a perioperative intravenous fluid administration strategy and acute kidney injury following off-pump coronary artery bypass surgery: an observational study*, Critical Care 19:350 (1995). Introducing fluid to blood also reduces hematocrit levels which has been shown to further increase mortality and morbidity. Research has also demonstrated that introducing saline solution to a patient may depress renal functional and/or inhibit natural fluid management processes. As such, appropriate monitoring and control of renal function may produce improved outcomes and, in particular, may reduce post-operative instances of AKI.

Figure 25:
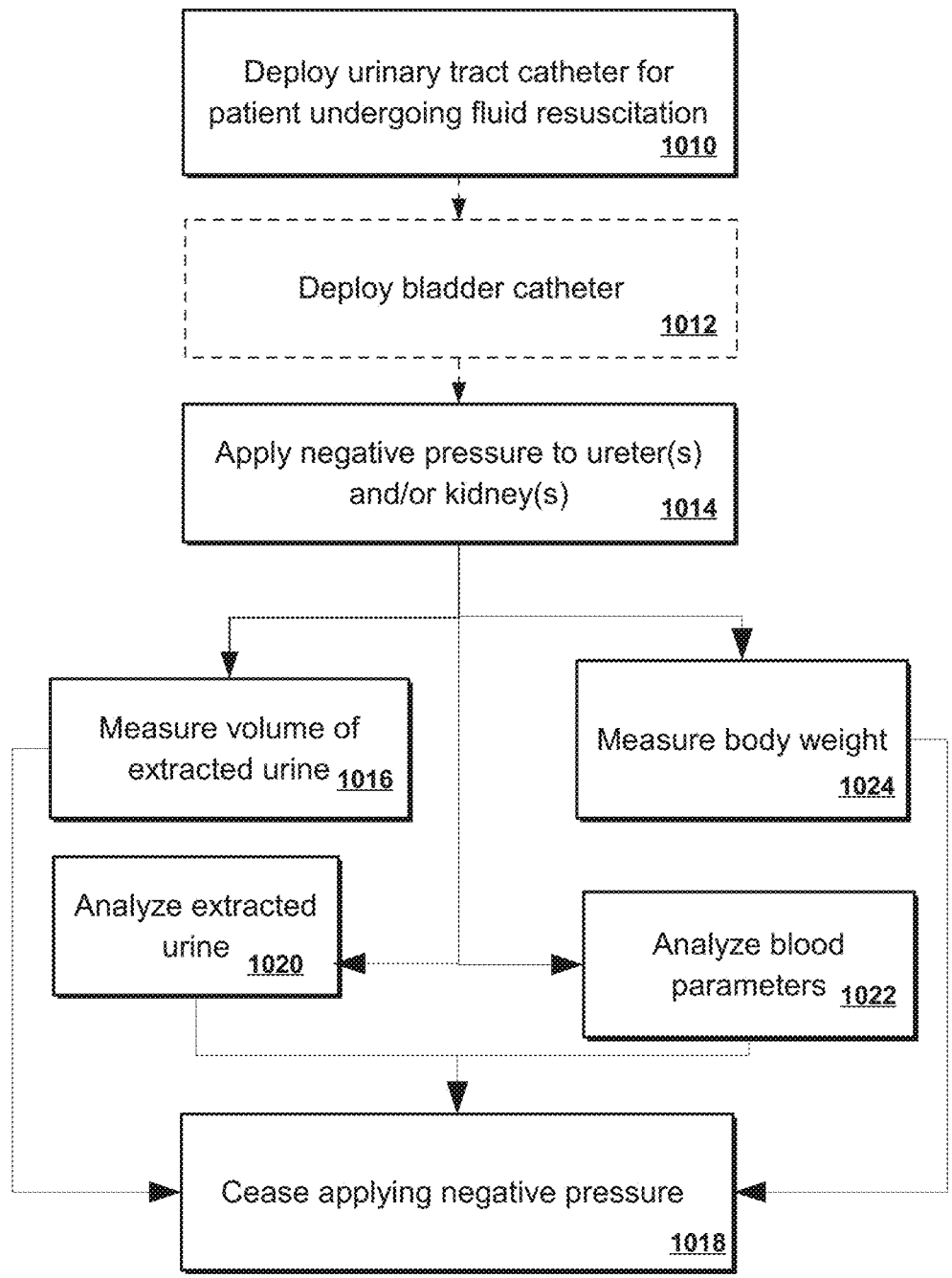
FIG. 25 is a flow chart illustrating a process for treating a patient undergoing fluid resuscitation according to an example of the disclosure.

A method of treating a patient undergoing fluid resuscitation is illustrated in FIG. 25. As shown at box 1010, the method comprises deploying a ureteral catheter in the ureter and/or kidney of a patient such that flow of urine from the ureter and/or kidney is not prevented by occlusion of the ureter and/or kidney. For example, a fluid collecting portion of the catheter may be positioned in the renal pelvis. In other examples, the catheter may be deployed in the bladder or ureter. The catheter can comprise one or more of the ureter catheters described herein. For example, the catheter can comprise a tube defining a drainage lumen and comprising a helical retention portion and a plurality of drainage ports. In other examples, the catheter can include an inflatable retention portion (e.g., a balloon catheter) or a pigtail coil.

As shown at box 1012, optionally, a bladder catheter may also be deployed in the patient's bladder. For example, the bladder catheter may be positioned to seal the urethra opening to prevent passage of urine from the body through the urethra. The bladder catheter can include an inflatable anchor (e.g., a Foley catheter) for maintaining the distal end of the catheter in the bladder. As described herein, other arrangements of coils and helices may also be used to obtain proper positioning of the bladder catheter. The bladder catheter can be configured to collect urine which entered the patient's bladder prior to placement of the ureteral catheter(s). The bladder catheter may also collect urine which flows past the fluid collection portion(s) of the ureteral catheter and enters the bladder. In some examples, a proximal portion of the ureteral catheter may be positioned in a drainage lumen of the bladder catheter. In a similar manner, the bladder catheter may be advanced into the bladder using the same guidewire used for positioning of the ureteral catheter(s). In some examples, negative pressure may be provided to the bladder through the drainage lumen of the bladder catheter. In other examples, negative pressure may only be applied to the ureteral catheter(s). In that case, the bladder catheter drains by gravity.

As shown at box 1014, following deployment of the ureteral catheter(s), negative pressure is applied to the ureter and/or kidney through the ureteral catheter(s). For example, negative pressure can be applied for a period of time sufficient to extract urine comprising a portion of the fluid provided to the patient during the fluid resuscitation procedure. As described herein, negative pressure can be provided by an external pump connected to a proximal end or port of the catheter. The pump can be operated continually or periodically dependent on therapeutic requirements of the patient. In some cases, the pump may alternate between applying negative pressure and positive pressure.

Negative pressure may continue to be applied for a predetermined period of time. For example, a user may be instructed to operate the pump for the duration of a surgical procedure or for a time period selected based on physiological characteristics of the patient. In other examples, patient condition may be monitored to determine when a sufficient amount of fluid has been drawn from the patient. For example, as shown at box 1016, fluid expelled from the body may be collected and a total volume of obtained fluid may be monitored. In that case, the pump can continue to operate until a predetermined fluid volume has been collected from the ureteral and/or bladder catheters. The predetermined fluid volume may be based, for example, on a volume of fluid provided to the patient prior to and during the surgical procedure. As shown at box 1018, application of negative pressure to the ureter and/or kidneys is stopped when the collected total volume of fluid exceeds the predetermined fluid volume.

In other examples, operation of the pump can be determined based on measured physiological parameters of the patient, such as measured creatinine clearance, blood creatinine level, or hematocrit ratio. For example, as shown at box 1020, urine collected form the patient may be analyzed by one or more sensors associated with the catheter and/or pump. The sensor can be a capacitance sensor, analyte sensor, optical sensor, or similar device configured to measure urine analyte concentration. In a similar manner, as shown at box 1022, a patient's blood creatinine or hematocrit level could be analyzed based on information obtain from the patient monitoring sensors discussed hereinabove. For example, a capacitance sensor may be placed in an existing extracorporeal blood system. Information obtained by the capacitance sensor may be analyzed to determine a patient's hematocrit ratio. The measured hematocrit ratio may be compared to certain expected or therapeutically acceptable values. The pump may continue to apply negative pressure to the patient's ureter and/or kidney until measured values within the therapeutically acceptable range are obtained. Once a therapeutically acceptable value is obtained, application of negative pressure may be stopped as shown at box 1018.

In other examples, as shown at box 2024, patient body weight may be measured to assess whether fluid is being removed from the patient by the applied negative pressure therapy. For example, a patient's measured bodyweight (including fluid introduced during a fluid resuscitation procedure) can be compared to a patient's dry body weight. As used herein, dry weights is defined as normal body weight measured when a patient is not over-diluted. For example, a patient who is not experiencing one or more of: elevated blood pressure, lightheadedness or cramping, swelling of legs, feet, arms, hands, or around the eyes, and who is breathing comfortably, likely does not have excess fluid. A weight measured when the patient is not experiencing such symptoms can be a dry body weight. Patient weight can be measured periodically until the measured weight approaches the dry body weight. When the measured weight approaches (e.g., is within between 5% and 10% of dry body weight), as shown at box 1018, application of negative pressure can be stopped.

EXPERIMENTAL EXAMPLES

Inducement of negative pressure within the renal pelvis of farm swine was performed for the purpose of evaluating effects of negative pressure therapy on renal congestion in the kidney. An objective of these studies was to demonstrate whether a negative pressure delivered into the renal pelvis significantly increases urine output in a swine model of renal congestion. In Example 1, a pediatric Fogarty catheter, normally used in embolectomy or bronchoscopy applications, was used in the swine model solely for proof of principle for inducement of negative pressure in the renal pelvis. It is not suggested that a Fogarty catheter be used in humans in clinical settings to avoid injury of urinary tract tissues. In Example 2, the ureteral catheter 112 shown in FIGS. 2A and 2B, and including a helical retention portion for mounting or maintaining a distal portion of the catheter in the renal pelvis or kidney, was used.

Example 1

Method

Figure 21:
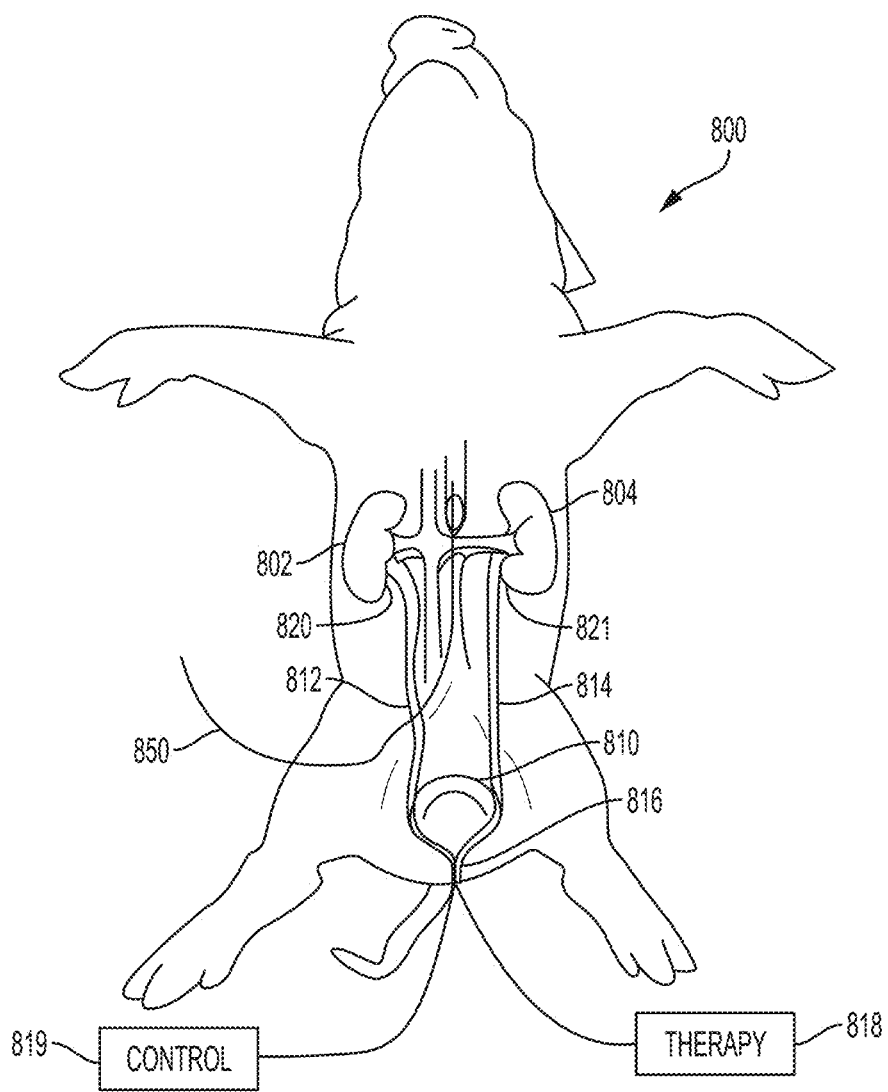
FIG. 21 is a schematic drawing of an experimental set-up for evaluating negative pressure therapy in a swine model.

Four farm swine 800 were used for purposes of evaluating effects of negative pressure therapy on renal congestion in the kidney. As shown in FIG. 21, pediatric Fogarty catheters 812, 814 were inserted to the renal pelvis region 820, 821 of each kidney 802, 804 of the four swine 800. The catheters 812, 814 were deployed within the renal pelvis region by inflating an expandable balloon to a size sufficient to seal the renal pelvis and to maintain the position of the balloon within the renal pelvis. The catheters 812, 814 extend from the renal pelvis 802, 804, through a bladder 810 and urethra 816, and to fluid collection containers external to the swine.

Urine output of two animals was collected for a 15 minute period to establish a baseline for urine output volume and rate. Urine output of the right kidney 802 and the left kidney 804 were measured individually and found to vary considerably. Creatinine clearance values were also determined.

Renal congestion (e.g., congestion or reduced blood flow in the veins of the kidney) was induced in the right kidney 802 and the left kidney 804 of the animal 800 by partially occluding the inferior vena cava (IVC) with an inflatable balloon catheter 850 just above to the renal vein outflow. Pressure sensors were used to measure IVC pressure. Normal IVC pressures were 1-4 mmHg. By inflating the balloon of the catheter 850 to approximately three quarters of the IVC diameter, the IVC pressures were elevated to between 15-25 mmHg. Inflation of the balloon to approximately three quarters of IVC diameter resulted in a 50-85% reduction in urine output. Full occlusion generated IVC pressures above 28 mmHg and was associated with at least a 95% reduction in urine output.

One kidney of each animal 800 was not treated and served as a control ("the control kidney 802"). The ureteral catheter 812 extending from the control kidney was connected to a fluid collection container 819 for determining fluid levels. One kidney ("the treated kidney 804") of each animal was treated with negative pressure from a negative pressure source (e.g., a therapy pump 818 in combination with a regulator designed to more accurately control the low magnitude of negative pressures) connected to the ureteral catheter 814. The pump 818 was an Air Cadet Vacuum Pump from Cole-Parmer Instrument Company (Model No. EW-07530-85). The pump 818 was connected in series to the regulator. The regulator was a V-800 Series Miniature Precision Vacuum Regulator—⅛ NPT Ports (Model No. V-800-10-W/K), manufactured by Airtrol Components Inc.

The pump 818 was actuated to induce negative pressure within the renal pelvis 820, 821 of the treated kidney according to the following protocol. First, the effect of negative pressure was investigated in the normal state (e.g., without inflating the IVC balloon). Four different pressure levels (−2, −10, −15, and −20 mmHg) were applied for 15 minutes each and the rate of urine produced and creatinine clearance were determined. Pressure levels were controlled and determined at the regulator. Following the −20 mmHg therapy, the IVC balloon was inflated to increase the pressure by 15-20 mmHg. The same four negative pressure levels were applied. Urine output rate and creatinine clearance rate for the congested control kidney 802 and treated kidney 804 were obtained. The animals 800 were subject to congestion by partial occlusion of the IVC for 90 minutes. Treatment was provided for 60 minutes of the 90 minute congestion period.

Following collection of urine output and creatinine clearance data, kidneys from one animal were subjected to gross examination then fixed in a 10% neutral buffered formalin. Following gross examination, histological sections were obtained, examined, and magnified images of the sections were captured. The sections were examined using an upright Olympus BX41 light microscope and images were captured using an Olympus DP25 digital camera. Specifically, photomicrograph images of the sampled tissues were obtained at low magnification (20× original magnification) and high magnification (100× original magnification). The obtained images were subjected to histological evaluation. The purpose of the evaluation was to examine the tissue histologically and to qualitatively characterize congestion and tubular degeneration for the obtained samples.

Surface mapping analysis was also performed on obtained slides of the kidney tissue. Specifically, the samples were stained and analyzed to evaluate differences in size of tubules for treated and untreated kidneys. Image processing techniques calculated a number and/or relative percentage of pixels with different coloration in the stained images. Calculated measurement data was used to determine volumes of different anatomical structures.

Results

Urine Output and Creatinine Clearance

Urine output rates were highly variable. Three sources of variation in urine output rate were observed during the study. The inter-individual and hemodynamic variability were anticipated sources of variability known in the art. A third source of variation in urine output, upon information and belief believed to be previously unknown, was identified in the experiments discussed herein, namely, contralateral intra-individual variability in urine output.

Baseline urine output rates were 0.79 ml/min for one kidney and 1.07 ml/min for the other kidney (e.g., a 26% difference). The urine output rate is a mean rate calculated from urine output rates for each animal.

When congestion was provided by inflating the IVC balloon, the treated kidney urine output dropped from 0.79 ml/min to 0.12 ml/min (15.2% of baseline). In comparison, the control kidney urine output rate during congestion dropped from 1.07 ml/min to 0.09 ml/min (8.4% of baseline). Based on urine output rates, a relative increase in treated kidney urine output compared to control kidney urine output was calculated, according to the following equation:

$$(\text{Therapy Treated}/\text{Baseline Treated})/(\text{Therapy Control}/\text{Baseline Control}) = \text{Relative increase}$$

$$(0.12 \text{ ml/min}/0.79 \text{ ml/min})/(0.09 \text{ ml/min}/1.07 \text{ ml/min}) = 180.6\%$$

Thus, the relative increase in treated kidney urine output rate was 180.6% compared to control. This result shows a greater magnitude of decrease in urine production caused by congestion on the control side when compared to the treatment side. Presenting results as a relative percentage difference in urine output adjusts for differences in urine output between kidneys.

Figure 22:
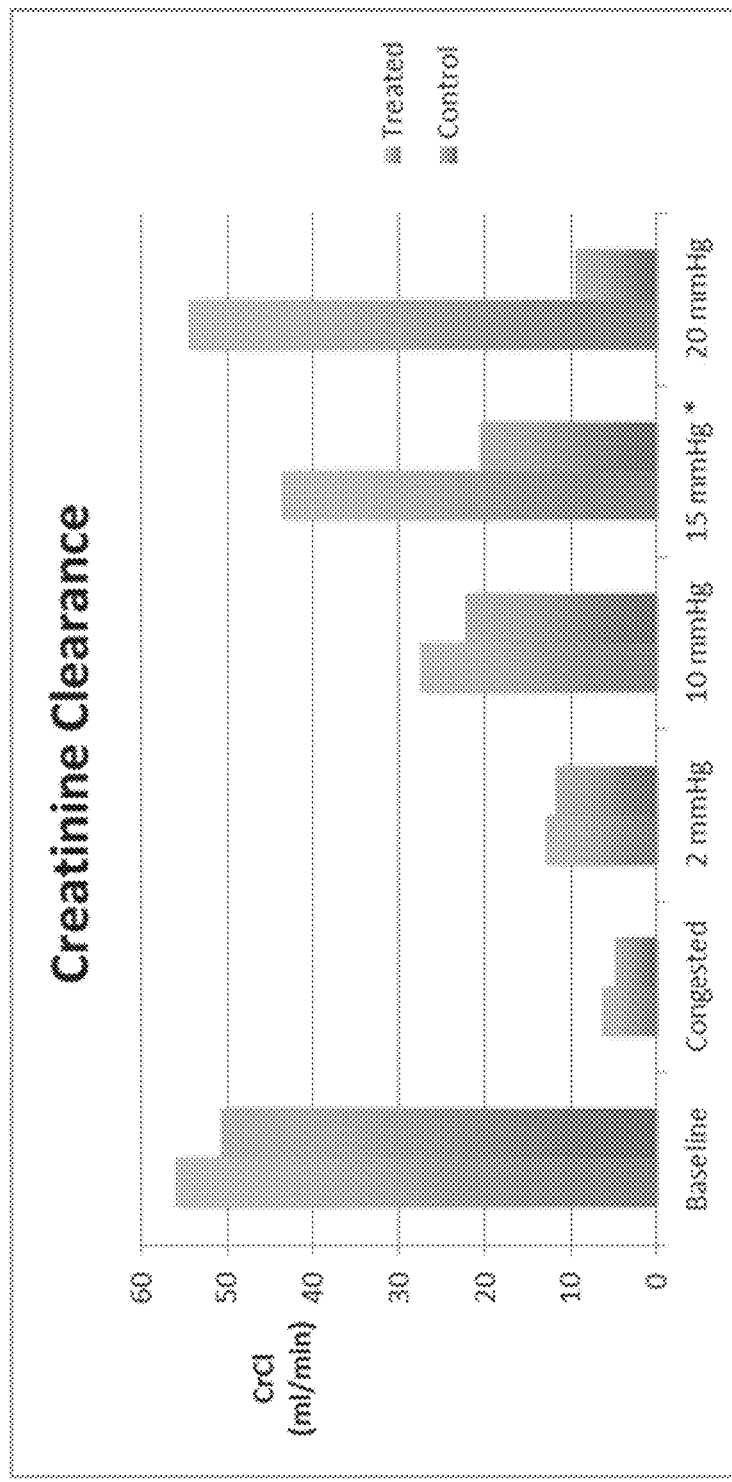
FIG. 22 is a graph of creatinine clearance rates for tests conducted using the experimental set-up shown in FIG. 21.

Creatinine clearance measurements for baseline, congested, and treated portions for one of the animals are shown in FIG. 22.

Gross Examination and Histological Evaluation

Based on gross examination of the control kidney (right kidney) and treated kidney (left kidney), it was determined that the control kidney had a uniformly dark red-brown color, which corresponds with more congestion in the control kidney compared to the treated kidney. Qualitative evaluation of the magnified section images also noted increased congestion in the control kidney compared to the treated kidney. Specifically, as shown in Table 1, the treated kidney exhibited lower levels of congestion and tubular degeneration compared to the control kidney. The following qualitative scale was used for evaluation of the obtained slides.

Congestion

| Lesion | Score |
| --- | --- |
| None: | 0 |
| Mild: | 1 |
| Moderate: | 2 |
| Marked: | 3 |
| Severe: | 4 |

Tubular Degeneration

| Lesion | Score |
| --- | --- |
| None: | 0 |
| Mild: | 1 |
| Moderate: | 2 |
| Marked: | 3 |
| Severe: | 4 |

TABLE 1

TABULATED RESULTS

| | | Histologic lesions | | |
| --- | --- | --- | --- | --- |
| Animal ID/Organ/Gross lesion | Slide number | Congestion | Tubular hyaline casts | Granulomas |
| 6343/Left Kidney/Normal | R16-513-1 | 1 | 1 | 0 |
| 6343/Left Kidney/Normal with hemorrhagic streak | R16-513-2 | 1 | 1 | 0 |

TABLE 1-continued

TABULATED RESULTS

| | | Histologic lesions | | |
|---|---|---|---|---|
| Animal ID/Organ/Gross lesion | Slide number | Congestion | Tubular hyaline casts | Granulomas |
| 6343/Right Kidney/Congestion | R16-513-3 | 2 | 2 | 1 |
| 6343/Right Kidney/Congestion | R16-513-4 | 2 | 1 | 1 |

As shown in Table 1, the treated kidney (left kidney) exhibited only mild congestion and tubular degeneration. In contrast, the control kidney (right kidney) exhibited moderate congestion and tubular degeneration. These results were obtained by analysis of the slides discussed below.

Figure 23A:
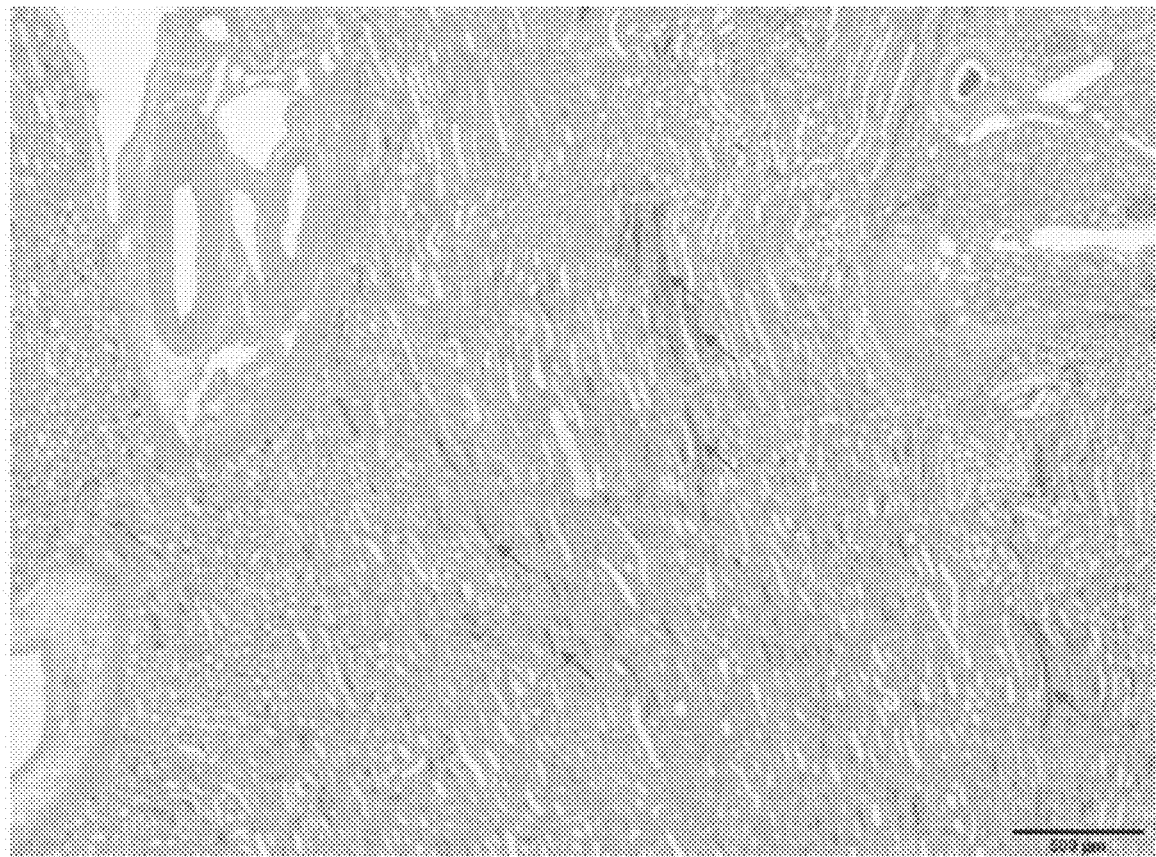
FIG. 23A is a low magnification photomicrograph of kidney tissue from a congested kidney treated with negative pressure therapy.
Figure 23B:
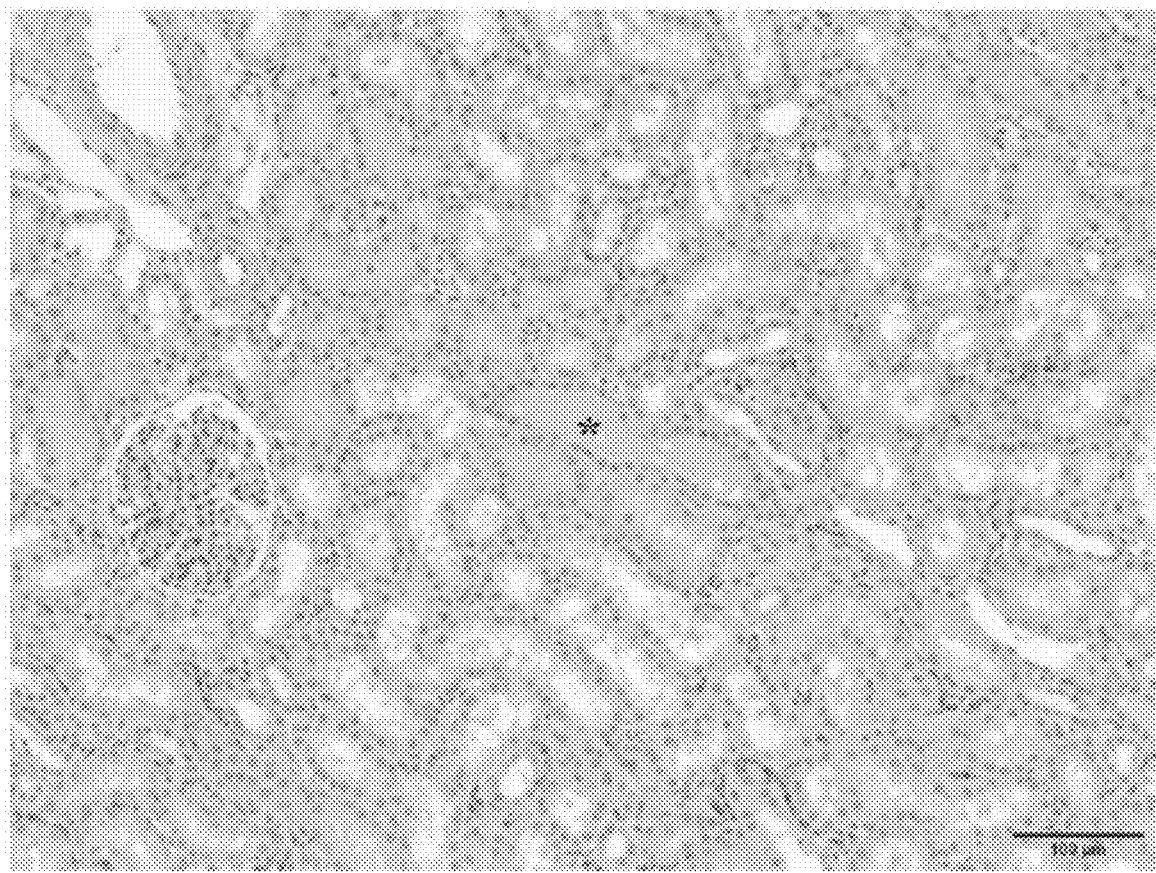
FIG. 23B is a high magnification photomicrograph of the kidney tissue shown in FIG. 23A.

FIGS. 23A and 23B are low and high magnification photomicrographs of the left kidney (treated with negative pressure) of the animal. Based on the histological review, mild congestion in the blood vessels at the corticomedullary junction was identified, as indicated by the arrows. As shown in FIG. 23B, a single tubule with a hyaline cast (as identified by the asterisk) was identified.

Figure 23C:
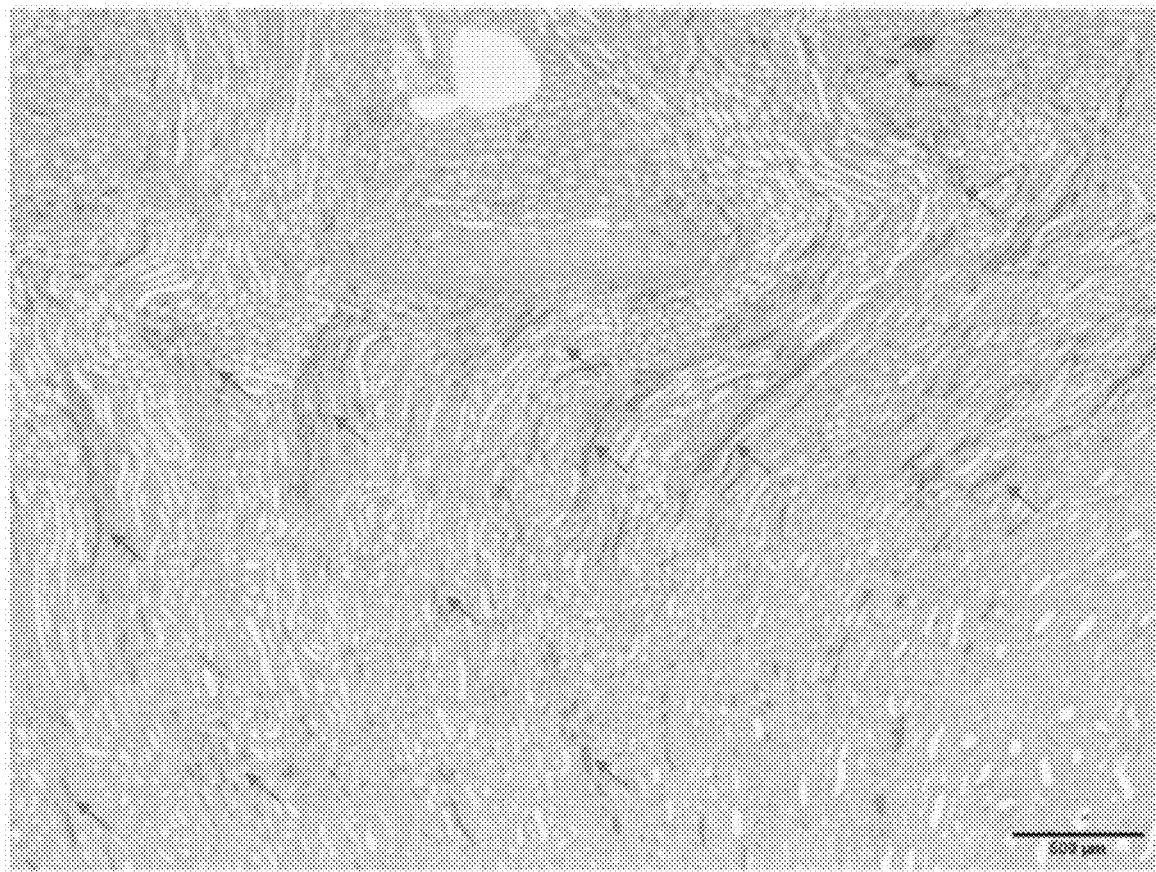
FIG. 23C is a low magnification photomicrograph of kidney tissue from a congested and untreated (e.g., control) kidney.
Figure 23D:
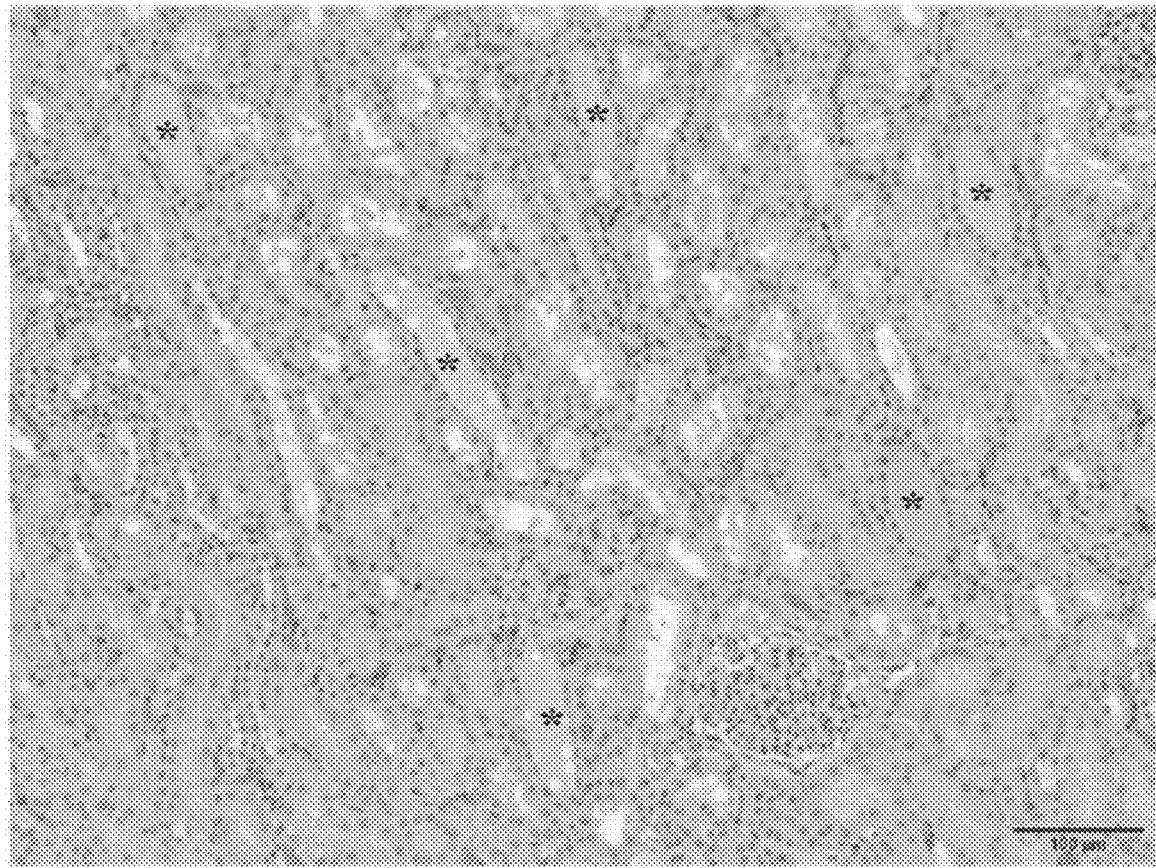
FIG. 23D is a high magnification photomicrograph of the kidney tissue shown in FIG. 23C

FIGS. 23C and 23D are low and high resolution photomicrographs of the control kidney (right kidney). Based on the histological review, moderate congestion in the blood vessel at the corticomedullary junction was identified, as shown by the arrows in FIG. 23C. As shown in FIG. 23D, several tubules with hyaline casts were present in the tissue sample (as identified by asterisks in the image). Presence of a substantial number of hyaline casts is evidence of hypoxia.

Surface mapping analysis provided the following results. The treated kidney was determined to have 1.5 times greater fluid volume in Bowman's space and 2 times greater fluid volume in tubule lumen. Increased fluid volume in Bowman's space and the tubule lumen corresponds to increased urine output. In addition, the treated kidney was determined to have 5 times less blood volume in capillaries compared to the control kidney. The increased volume in the treated kidney appears to be a result of (1) a decrease in individual capillary size compared to the control and (2) an increase in the number of capillaries without visible red blood cells in the treated kidney compared to the control kidney, an indicator of less congestion in the treated organ.

Summary

These results indicate that the control kidney had more congestion and more tubules with intraluminal hyaline casts, which represent protein-rich intraluminal material, compared to the treated kidney. Accordingly, the treated kidney exhibits a lower degree of loss of renal function. While not intending to be bound by theory, it is believed that as severe congestion develops in the kidney, hypoxemia of the organ follows. Hypoxemia interferes with oxidative phosphorylation within the organ (e.g., ATP production). Loss of ATP and/or a decrease in ATP production inhibits the active transport of proteins causing intraluminal protein content to increase, which manifests as hyaline casts. The number of renal tubules with intraluminal hyaline casts correlates with the degree of loss of renal function. Accordingly, the reduced number of tubules in the treated left kidney is believed to be physiologically significant. While not intending to be bound by theory, it is believed that these results show that damage to the kidney can be prevented or inhibited by applying negative pressure to a catheter inserted into the renal pelvis to facilitate urine output.

Example 2

Method

Four (4) farm swine (A, B, C, D) were sedated and anesthetized. Vitals for each of the swine were monitored throughout the experiment and cardiac output was measured at the end of each 30-minute phase of the study. Ureteral catheters, such as the ureteral catheter 112 shown in FIGS. 2A and 2B, were deployed in the renal pelvis region of the kidneys of each of the swine. The deployed catheters were a 6 Fr catheter having an outer diameter of 2.0±0.1 mm. The catheters were 54±2 cm in length, not including the distal retention portion. The retention portion was 16±2 mm in length. As shown in the catheter 112 in FIGS. 2A and 2B, the retention portion included two full coils and one proximal half coil. The outer diameter of the full coils, shown by line D1 in FIGS. 2A and 2B, was 18±2 mm. The half coil diameter D2 was about 14 mm. The retention portion of the deployed ureteral catheters included six drainage holes, plus an additional hole at the distal end of the catheter tube. The diameter of each of the drainage holes was 0.83±0.01 mm. The distance between adjacent drainage holes 132, specifically the linear distance between drainage holes when the coils were straightened, was 22.5±2.5 mm.

The ureteral catheters were positioned to extend from the renal pelvis of the swine, through the bladder, and urethra, and to fluid collection containers external to each swine. Following placement of the ureteral catheters, pressure sensors for measuring IVC pressure were placed in the IVC at a position distal to the renal veins. An inflatable balloon catheter, specifically a PTS® percutaneous balloon catheter (30 mm diameter by 5 cm length), manufactured by NuMED Inc. of Hopkinton, N.Y., was expanded in the IVC at a position proximal to the renal veins. A thermodilution catheter, specifically a Swan-Ganz thermodilution pulmonary artery catheter manufactured by Edwards Lifesciences Corp. of Irvine, Calif., was then placed in the pulmonary artery for the purpose of measuring cardiac output.

Initially, baseline urine output was measured for 30 minutes, and blood and urine samples were collected for biochemical analysis. Following the 30-minute baseline period, the balloon catheter was inflated to increase IVC pressure from a baseline pressure of 1-4 mmHg to an elevated congested pressure of about 20 mmHg (+/−5 mmHg). A congestion baseline was then collected for 30 minutes with corresponding blood and urine analysis.

At the end of the congestion period, the elevated congested IVC pressure was maintained and negative pressure diuresis treatment was provided for swine A and swine C. Specifically, the swine (A, C) were treated by applying a negative pressure of −25 mmHg through the ureteral catheters with a pump. As in previously-discussed examples, the pump was an Air Cadet Vacuum Pump from Cole-Parmer Instrument Company (Model No. EW-07530-85). The pump was connected in series to a regulator. The regulator was a V-800 Series Miniature Precision Vacuum Regulator—⅛ NPT Ports (Model No. V-800-10-W/K), manufactured by Airtrol Components Inc. The swine were observed for 120 minutes, as treatment was provided. Blood and urine collection were performed every 30 minutes, during the treatment period. Two of the swine (B, D) were treated as congested controls (e.g., negative pressure was not applied to the renal pelvis through the ureteral catheters), meaning that the two swine (B, D) did not receive negative pressure diuresis therapy.

Following collection of urine output and creatinine clearance data for the 120-minute treatment period, the animals were sacrificed and kidneys from each animal were subjected to gross examination. Following gross examination, histological sections were obtained and examined, and magnified images of the sections were captured.

Results

Measurements collected during the Baseline, Congestion, and Treatment periods are provided in Table 2. Specifically, urine output, serum creatinine, and urinary creatinine measurements were obtained for each time period. These values allow for the calculation of a measured creatinine clearance as follows:

$$\text{Creatinine Clearance: } CrCl = \text{Urine Output (ml/min)} * \frac{\text{Urinary Creatinine (mg/dl)}}{\text{Serum Creatinine (mg/dl)}}$$

In addition, Neutrophil gelatinase-associated lipocalin (NGAL) values were measured from serum samples obtained for each time period and Kidney Injury Molecule 1 (KIM-1) values were measured from the urine samples obtained for each time period. Qualitative histological findings determined from review of the obtained histological sections are also included in Table 2.

Animal A: The animal weighed 50.6 kg and had a baseline urine output rate of 3.01 ml/min, a baseline serum creatinine of 0.8 mg/dl, and a measured CrCl of 261 ml/min. It is noted that these measurements, aside from serum creatinine, were uncharacteristically high relative to other animals studied. Congestion was associated with a 98% reduction in urine output rate (0.06 ml/min) and a >99% reduction in CrCl (1.0 ml/min). Treatment with negative pressure applied through the ureteral catheters was associated with urine output and CrCl of 17% and 12%, respectively, of baseline values, and 9× and >10×, respectively, of congestion values. Levels of NGAL changed throughout the experiment, ranging from 68% of baseline during congestion to 258% of baseline after 90 minutes of therapy. The final value was 130% of baseline. Levels of KIM-1 were 6 times and 4 times of baseline for the first two 30-minute windows after baseline assessment, before increasing to 68×, 52×, and 63× of baseline values, respectively, for the last three collection periods. The 2-hour serum creatinine was 1.3 mg/dl. Histological examination revealed an overall congestion level, measured by blood volume in capillary space, of 2.4%. Histological examination also noted several tubules with intraluminal hyaline casts and some degree of tubular epithelial degeneration, a finding consistent with cellular damage.

Animal B: The animal weighed 50.2 kg and had a baseline urine output rate of 2.62 ml/min and a measured CrCl of 172 ml/min (also higher than anticipated). Congestion was associated with an 80% reduction in urine output rate (0.5 ml/min) and an 83% reduction in CrCl (30 ml/min). At 50 minutes into the congestion (20 minutes after the congestion baseline period), the animal experienced an abrupt drop in mean arterial pressure and respiration rate, followed by tachycardia. The anesthesiologist administered a dose of phenylephrine (75 mg) to avert cardiogenic shock. Phenylephrine is indicated for intravenous administration when blood pressure drops below safe levels during anesthesia.

TABLE 2

| Animal<br>Treatment assignment | A<br>Treatment | B<br>Control | C<br>Treatment | D<br>Control |
|---|---|---|---|---|
| Baseline: | | | | |
| Urine output (ml/min) | 3.01 | 2.63 | 0.47 | 0.98 |
| Serum creatinine (mg/dl) | 0.8 | 0.9 | 3.2 | 1.0 |
| Creatinine clearance (ml/min) | 261 | 172 | 5.4 | 46.8 |
| Serum NGAL (ng/ml) | 169 | * | 963 | 99 |
| Urinary KIM-1 (ng/ml) | 4.11 | * | 3.59 | 1.16 |
| Congestion: | | | | |
| Urine output (ml/min) | 0.06 (2%) | 0.53 (20%) | 0.12 (25%) | 0.24 (25%) |
| Serum creatinine (mg/dl) | 1.2 (150%) | 1.1 (122%) | 3.1 (97%) | 1.2 (120%) |
| Creatinine clearance (ml/min) | 1.0 (0.4%) | 30.8 (18%) | 1.6 (21%) | 16.2 (35%) |
| Serum NGAL (ng/ml) | 102 (60%) | * | 809 (84%) | 126 (127%) |
| Urinary KIM-1 (ng/ml) | 24.3 (591%) | * | 2.2 (61%) | 1.39 (120%) |
| Treatment: | | | | |
| Urine output (ml/min) | 0.54 (17%) | ** | 0.47 (101%) | 0.35 (36%) |
| Serum creatinine (mg/dl) | 1.3 (163%) | | 3.1 (97%) | 1.7 (170%) |
| Creatinine clearance (ml/min) | 30.6 (12%) | | 18.3 (341%) | 13.6 (29%) |
| Serum NGAL (ng/ml) | 197 (117%) | | 1104 (115%) | 208 (209%) |
| Urinary KIM-1 (ng/ml) | 260 (6326%) | | 28.7 (799%) | 233 (20000%) |
| Histological findings: | | | | |
| Blood volume in capillary space | 2.4% | ** | 0.9% | 4.0% |
| Hyaline casts | Mild/Mod | | None | Mod |
| Degranulation | Mild/Mod | | None | Mod |

Data are raw values (% baseline)
* not measured
** confounded by phenylephrine

However, since the experiment was testing the impact of congestion on renal physiology, administration of phenylephrine confounded the remainder of the experiment.

Animal C: The animal weighed 39.8 kg and had a baseline urine output rate of 0.47 ml/min, a baseline serum creatinine of 3.2 mg/dl, and a measured CrCl of 5.4 ml/min. Congestion was associated with a 75% reduction in urine output (0.12 ml/min) and a 79% reduction in CrCl (1.6 ml/min). It was determined that baseline NGAL levels were >5× the upper limit of normal (ULN). Treatment with negative pressure applied to the renal pelvis through the ureteral catheters was associated with a normalization of urine output (101% of baseline) and a 341% improvement in CrCl (18.2 ml/min). Levels of NGAL changed throughout the experiment, ranging from 84% of baseline during congestion to 47% to 84% of baseline between 30 and 90 minutes. The final value was 115% of baseline. Levels of KIM-1 decreased 40% from baseline within the first 30 minutes of congestion, before increasing to 8.7×, 6.7×, 6.6×, and 8× of baseline values, respectively, for the remaining 30-minute windows. Serum creatinine level at 2 hours was 3.1 mg/dl. Histological examination revealed an overall congestion level, measured by blood volume in capillary space, of 0.9%. The tubules were noted to be histologically normal.

Animal D: The animal weighed 38.2 kg and had a baseline urine output of 0.98 ml/min, a baseline serum creatinine of 1.0 mg/dl, and a measured CrCl of 46.8 ml/min. Congestion was associated with a 75% reduction in urine output rate (0.24 ml/min) and a 65% reduction in Cr Cl (16.2 ml/min). Continued congestion was associated with a 66% to 91% reduction of urine output and 89% to 71% reduction in CrCl. Levels of NGAL changed throughout the experiment, ranging from 127% of baseline during congestion to a final value of 209% of baseline. Levels of KIM-1 remained between 1× and 2× of baseline for the first two 30-minute windows after baseline assessment, before increasing to 190×, 219×, and 201× of baseline values for the last three 30-minute periods. The 2-hour serum creatinine level was 1.7 mg/dl. Histological examination revealed an overall congestion level 2.44× greater than that observed in tissue samples for the treated animals (A, C) with an average capillary size 2.33 times greater than that observed in either of the treated animals. The histological evaluation also noted several tubules with intraluminal hyaline casts as well as tubular epithelial degeneration, indicating substantial cellular damage.

Summary

While not intending to be bound by theory, it is believed that the collected data supports the hypothesis that venous congestion creates a physiologically significant impact on renal function. In particular, it was observed that elevation of the renal vein pressure reduced urine output by 75% to 98% within seconds. The association between elevations in biomarkers of tubular injury and histological damage is consistent with the degree of venous congestion generated, both in terms of magnitude and duration of the injury.

The data also appears to support the hypothesis that venous congestion decreases the filtration gradients in the medullary nephrons by altering the interstitial pressures. The change appears to directly contribute to the hypoxia and cellular injury within medullary nephrons. While this model does not mimic the clinical condition of AKI, it does provide insight into the mechanical sustaining injury.

The data also appears to support the hypothesis that applying negative pressure to the renal pelvis through ureteral catheters can increase urine output in a venous congestion model. In particular, negative pressure treatment was associated with increases in urine output and creatinine clearance that would be clinically significant. Physiologically meaningful decreases in medullary capillary volume and smaller elevations in biomarkers of tubular injury were also observed. Thus, it appears that by increasing urine output rate and decreasing interstitial pressures in medullary nephrons, negative pressure therapy may directly decrease congestion. While not intending to be bound by theory, by decreasing congestion, it may be concluded that negative pressure therapy reduces hypoxia and its downstream effects within the kidney in a venous congestion mediated AKI.

The experimental results appear to support the hypothesis that the degree of congestion, both in terms of the magnitude of pressure and duration, is associated with the degree of cellular injury observed. Specifically, an association between the degree of urine output reduction and the histological damage was observed. For example, treated Swine A, which had a 98% reduction in urine output, experienced more damage than treated Swine C, which had a 75% reduction in urine output. As would be expected, control Swine D, which was subjected to a 75% reduction in urine output without benefit of therapy for two and a half hours, exhibited the most histological damage. These findings are broadly consistent with human data demonstrating an increased risk for AKI onset with greater venous congestion. See e.g., Legrand, M. et al., *Association between systemic hemodynamics and septic acute kidney injury in critically ill patients: a retrospective observational study*. Critical Care 17:R278-86, 2013.

Example 3

Method

Inducement of negative pressure within the renal pelvis of farm swine was performed for the purpose of evaluating effects of negative pressure therapy on hemodilution of the blood. An objective of these studies was to demonstrate whether a negative pressure delivered into the renal pelvis significantly increases urine output in a swine model of fluid resuscitation.

Two pigs were sedated and anesthetized using ketamine, midazolam, isoflurane and propofol. One animal (#6543) was treated with a ureteral catheter and negative pressure therapy as described herein. The other, which received a Foley type bladder catheter, served as a control (#6566). Following placement of the catheters, the animals were transferred to a sling and monitored for 24 hours.

Fluid overload was induced in both animals with a constant infusion of saline (125 mL/hour) during the 24 hour follow-up. Urine output volume was measured at 15 minute increments for 24 hours. Blood and urine samples were collected at 4 hour increments. As shown in FIG. 21, a therapy pump 818 was set to induce negative pressure within the renal pelvis 820, 821 (shown in FIG. 21) of both kidneys using a pressure of −45 mmHg (+/−2 mmHg).

Results

Figure 26:
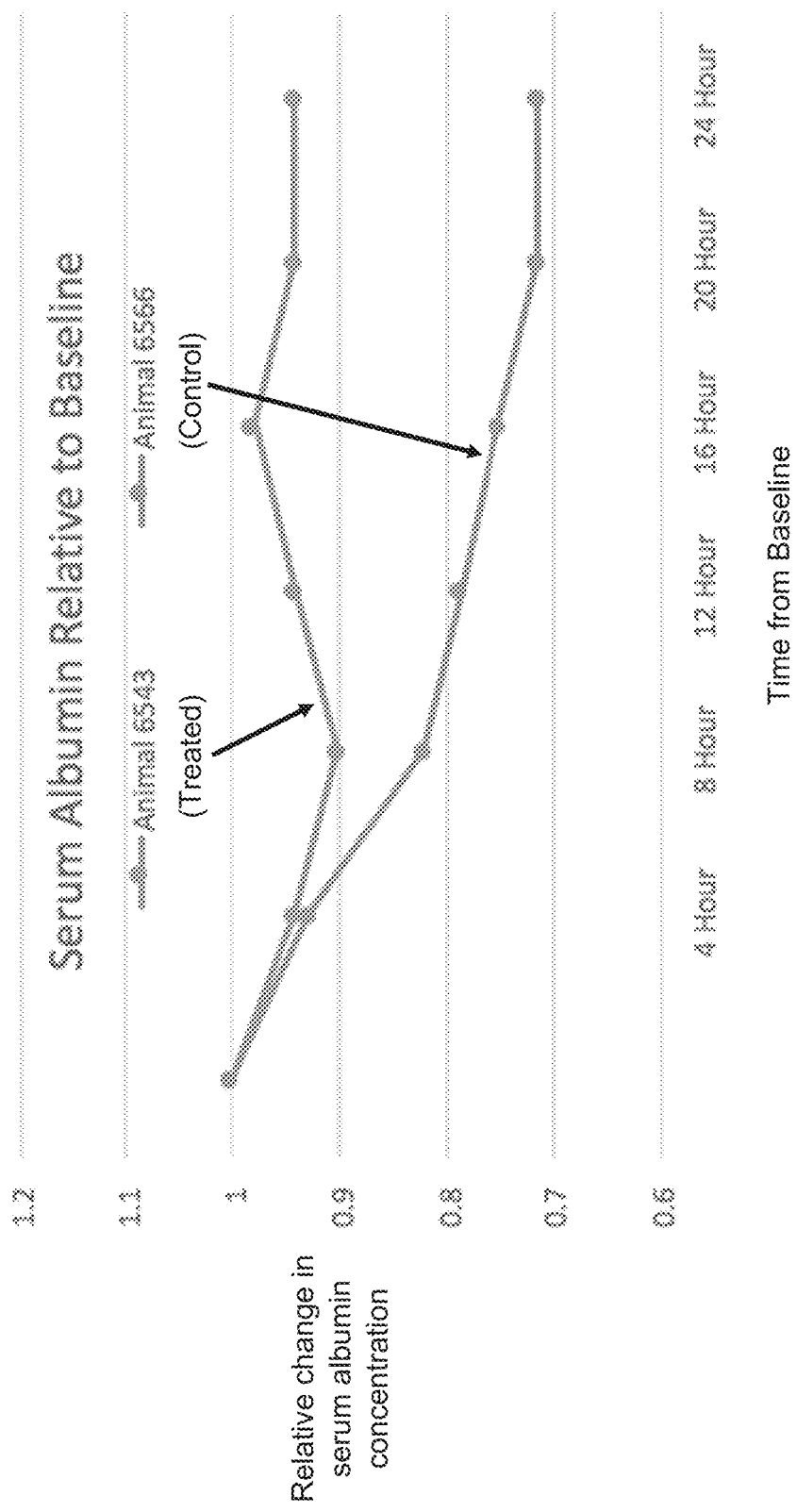
FIG. 26 is a graph of serum albumin relative to baseline for tests conduct on swine using the experimental method described herein.

Both animals received 7 L of saline over the 24 hour period. The treated animal produced 4.22 L of urine while the control produced 2.11 L. At the end of 24 hours, the control had retained 4.94 L of the 7 L administered, while the treated animal retained 2.81 L of the 7 L administered. FIG. 26 illustrates the change in serum albumin. The treated animal had a 6% drop in the serum albumin concentration over 24 hours, while the control animal had a 29% drop.

Summary

While not intending to be bound by theory, it is believed that the collected data supports the hypothesis that fluid overload induces clinically significant impact on renal function and, consequently induces hemodilution. In particular, it was observed that administration of large quantities of intravenous saline cannot be effectively removed by even healthy kidneys. The resulting fluid accumulation leads to hemodilution. The data also appears to support the hypothesis that applying negative pressure diuresis therapy to fluid overloaded animals can increase urine output, improve net fluid balance and decrease the impact of fluid resuscitation on development of hemodilution.

The preceding examples and embodiments of the invention have been described with reference to various examples. Modifications and alterations will occur to others upon reading and understanding the foregoing examples. Accordingly, the foregoing examples are not to be construed as limiting the disclosure.

What is claimed is:

1. A ureteral catheter, comprising:
a drainage lumen comprising a proximal portion and a distal portion configured to be positioned in a patient's kidney, renal pelvis, and/or in the ureter adjacent to the renal pelvis, the distal portion comprising a retention portion for maintaining positioning of the distal portion of the drainage lumen, the retention portion comprising at least two openings on a sidewall of the retention portion for permitting fluid flow into the drainage lumen,
wherein a total area of a proximal most opening of the at least two openings is less than a total area of more distal opening(s) nearer to the distal end of the drainage lumen, and wherein when negative pressure is applied through the ureteral catheter, fluid is drawn into the ureteral catheter through the at least two openings.

2. The ureteral catheter of claim 1, wherein the proximal portion of the drainage lumen is essentially free of or free of openings.

3. The ureteral catheter of claim 1, wherein the proximal portion of the drainage lumen is configured to extend outside of the patient's body.

4. The ureteral catheter of claim 1, further comprising a plurality of distance markings on the sidewall of the proximal portion of the drainage lumen to indicate how far the catheter is inserted into a urinary tract of a body of the patient.

5. The ureteral catheter of claim 4, further comprising a radiopaque band on the sidewall of the drainage lumen which is adjacent to a proximal end of the retention portion for identifying a location of the retention portion using fluoroscopic imaging, the radiopaque band having a different appearance than the distance markings when viewed by fluoroscopic imaging.

6. The ureteral catheter of claim 1, wherein the drainage lumen is formed, at least in part, from one or more of copper, silver, gold, nickel-titanium alloy, stainless steel, titanium, polyurethane, polyvinyl chloride, polytetrafluoroethylene (PTFE), latex, and silicone.

7. The ureteral catheter of claim 1, wherein the retention portion is biased in a coiled configuration, such that the retention portion comprises:
at least a first coil having a first diameter; and
at least a second coil having a second diameter, the first diameter being less than the second diameter, the second coil being closer to the distal end of the drainage lumen than the first coil.

8. The ureteral catheter of claim 7, wherein a gap between the sidewall of the first coil and an adjacent sidewall of the drainage lumen of the second coil is less than 3.0 mm.

9. The ureteral catheter of claim 7, wherein the first coil is a half coil extending from 0 degrees to 180 degrees and is free from openings, wherein the second coil is a full coil extending from 180 degrees to 540 degrees.

10. The ureteral catheter of claim 7, wherein the sidewall of the retention portion comprises a radially inwardly facing side and a radially outwardly facing side, and wherein a total area of the openings on the radially inwardly facing side is greater than a total area of the openings on the radially outwardly facing side.

11. The ureteral catheter of claim 7, wherein the sidewall of the retention portion comprises a radially inwardly facing side and a radially outwardly facing side, and wherein one or more openings are disposed on the radially inwardly facing side, and wherein the radially outwardly facing side is essentially free of openings.

12. The ureteral catheter of claim 7, wherein a distal-most portion of the retention portion is bent inwardly relative to a curvature of a distal-most coil, such that a central axis of the distal-most portion extends from the distal end of the drainage lumen toward the axis of the retention portion.

13. The ureteral catheter of claim 7, wherein the first diameter of the first coil is about 8 mm to 10 mm and the second diameter of the second coil is about 16 mm to 20 mm.

14. The ureteral catheter of claim 7, wherein the retention portion further comprises a third coil having a diameter greater than or equal to either the first diameter or the second diameter, the third coil being closer to an end of the distal portion of the drainage lumen than the second coil.

15. The ureteral catheter of claim 7, wherein the drainage lumen is transitionable between an uncoiled configuration for insertion from the patient's bladder into the patient's ureter and the coiled configuration for deployment within the patient's kidney, renal pelvis, and/or in the ureter adjacent to the renal pelvis.

16. The ureteral catheter of claim 15, wherein the drainage lumen is naturally biased to the coiled configuration.

17. The ureteral catheter of claim 1, wherein a total area of a first opening of the at least two openings closer to a distal end of the retention portion is greater than a total area of a second opening of the at least two openings that is closer to a proximal end of the retention portion.

18. The ureteral catheter of claim 1, wherein the drainage lumen has an inner diameter of about 0.5 mm to about 1.5 mm, and wherein a total area of openings closer to a proximal end of the retention portion is about 0.002 $mm^2$ to about 1.0 $mm^2$ and a total area of openings closer to a distal end of the retention portion is greater than about 0.5 $mm^2$.

19. The ureteral catheter of claim 1, wherein the drainage lumen has an uncoiled longitudinal length of about 30 cm to about 120 cm.

20. The ureteral catheter of claim 1, wherein one or more of the openings have a cross-sectional area of about 0.002 $mm^2$ to about 0.25 $mm^2$.

21. The ureteral catheter of claim 1, wherein the drainage lumen comprises an open distal end having an inner diameter of about 0.5 mm to about 1.5 mm.

22. The ureteral catheter of claim 1, wherein the openings are circles, each having a diameter of about 0.05 mm to about 1.5 mm.

23. The ureteral catheter of claim 1, wherein a spacing between adjacent openings of the at least two openings is about 0.1 mm to about 255 mm.

24. The ureteral catheter of claim 1, wherein the openings are circular and each have a diameter of about 0.05 mm to about 1.0 mm.

25. The ureteral catheter of claim 1, further comprising an opening at the distal end of the drainage lumen.

26. The ureteral catheter of claim 1, wherein each of the openings has the same area, and wherein more openings are present near the distal end of the retention portion than are near the proximal end of the retention portion.

27. The ureteral catheter of claim 1, wherein each opening of the at least two openings is independently selected from one or more of circles, triangles, rectangles, ellipses, ovals, and squares.

28. A system for inducing negative pressure in a portion of a urinary tract of a patient, the system comprising:
at least one ureteral catheter according to claim 1; and
a pump in fluid communication with the drainage lumen of the at least one ureteral catheter, the pump being configured for inducing a positive and/or a negative pressure in a portion of the urinary tract of the patient to draw fluid into the drainage lumen through the openings of the retention portion.

29. The system of claim 28, wherein the pump is configured to generate the positive and/or negative pressure in a proximal end of the drainage lumen.

30. The system of claim 28, wherein the pump applies a negative pressure of 100 mmHg or less to a proximal end of the drainage lumen.

31. The system of claim 30, wherein the pump is configured to operate at one of three pressure levels selected by a user, the pressure levels generating a negative pressure of 15 mmHg, 30 mmHg, and 45 mmHg.

32. The system of claim 28, wherein the pump is configured to alternate between generating negative pressure and generating positive pressure.

33. The system of claim 28, wherein the pump is configured to alternate between providing negative pressure and equalizing pressure to atmosphere.

34. The system of claim 28, further comprising:
one or more sensors in fluid communication with the drainage lumen, the one or more sensors being configured to determine information comprising at least one of capacitance, analyte concentration, and temperature of urine within the drainage lumen; and
a controller comprising computer readable memory including programming instructions that, when executed, cause the controller to:
receive the information from the one or more sensors and adjust an operating parameter of the pump based, at least in part, on the information received from the one or more sensors to increase or decrease vacuum pressure in the drainage lumen of the at least one ureteral catheter to adjust flow of urine through the drainage lumen.

35. The system of claim 28, comprising a first ureteral catheter of claim 1 configured to be placed in a first kidney, renal pelvis, and/or in the ureter adjacent to the renal pelvis of the patient and a second ureteral catheter of claim 1 configured to be placed in a second kidney, renal pelvis, and/or in the ureter adjacent to the renal pelvis of the patient,
wherein the pump is configured to apply negative pressure independently to the first ureteral catheter and the second ureteral catheter such that the pressure in each catheter can be the same or different from the other catheter.

36. The system of claim 28, wherein the pump has an accuracy of 10 mmHg or less.

37. The ureteral catheter of claim 1, wherein the at least two openings are disposed on an inwardly facing side of the retention portion.

38. The ureteral catheter of claim 1, wherein the retention portion comprises an outwardly facing side and an inwardly facing side, the inwardly facing side comprising at least one of the at least two openings, the outwardly facing side being configured to establish an outer periphery that contacts and inhibits mucosal tissue from occluding the at least one of the at least two openings upon application of negative pressure through the catheter.

* * * * *